United States Patent [19]

Kawai et al.

[11] Patent Number: 5,223,485
[45] Date of Patent: Jun. 29, 1993

[54] ANAPHYLATOXIN-RECEPTOR LIGANDS

[75] Inventors: Megumi Kawai; Yat S. Or; Paul E. Wiedeman; Jay R. Luly, all of Libertyville, Ill.; Mikel P. Moyer, Clinton, Conn.

[73] Assignee: Abbott Laboratories, Abbott Park, Ill.

[21] Appl. No.: 691,039

[22] PCT Filed: Jan. 16, 1990

[86] PCT No.: PCT/US90/00296

§ 371 Date: Jun. 19, 1991

§ 102(e) Date: Jun. 19, 1991

[87] PCT Pub. No.: WO90/09162

PCT Pub. Date: Aug. 23, 1990

Related U.S. Application Data

[63] Continuation-in-part of Ser. No. 304,693, Jan. 31, 1989, abandoned.

[51] Int. Cl.$^5$ .................... A61K 37/02; A61K 37/00; C07K 5/00; C07K 7/00

[52] U.S. Cl. .................... 514/16; 530/329; 514/17

[58] Field of Search .................... 514/16, 17; 530/329, 530/328

[56] References Cited

PUBLICATIONS

Köhl et al., vol. 20, Eur. J. Immunology, pp. 1463–1468, 1990.
Hartung et al. vol. 130, No. 3, J. of Immunology, pp. 1345–1349, Mar. 1983.
Hugli et al., Springer Seminars Immunopathology, 1984, pp. 193–219.

*Primary Examiner*—F. T. Moezie
*Assistant Examiner*—A. M. Davenport
*Attorney, Agent, or Firm*—Jerry F. Janssen

[57] ABSTRACT

Oligopeptide compounds or oligopeptide analogue compounds of the formula A-B-D-E-G-J-L-M-Q-T are ligands for the anaphylatoxin receptor and are useful in the treatment of inflammatory disease states. Also disclosed are anaphylatoxin receptor ligand compositions and a method for modulating anaphylatoxin activity.

6 Claims, No Drawings

ANAPHYLATOXIN-RECEPTOR LIGANDS

CROSS-REFERENCE TO RELATED APPLICATIONS

This application is a continuation-in-part of copending patent application Ser. No. 304,693 filed Jan. 31, 1989 and now abandoned.

TECHNICAL FIELD

This invention relates to organic compounds that modulate anaphylatoxin activity. It also relates to methods and compositions for modulating anaphylatoxin activity in human and animal hosts in need of such treatment.

BACKGROUND OF THE INVENTION

A wide variety of conditions including infection by bacteria, viruses or fungi, infiltration by cancer cells, allergic or autoimmune disorders and physically- or chemically-induced trauma causes an inflammatory response in humans. In all of these diseases and conditions in man and in most mammals, activation of the complement system (a set of proteins, regulatory factors and proteolytic enzymes) via either the classical or the alternative pathway results in the generation of biologically active peptides which serve to amplify and exacerbate the resulting inflammation. The most active peptide, anaphylatoxin C5a, a 74-amino acid polypeptide, is generated by cleavage of the alpha-chain of native C5 at a specific site by convertases (proteolytic enzymes) of the blood complement system as well as by enzymes of the coagulation system. C5a exists in vivo in two biologically active forms. Once it is liberated from C5, the carboxyl terminal arginine of C5a is rapidly removed by carboxypeptidase-N, leaving the des-Arg derivative. Although C5a des-Arg is less active than C5a, both are potent inflammatory mediators at concentrations likely to be generated in vivo (Fernandez, H. N.; Henson, P. M.; Otani, A.; Hugli, T. E. *J. Immunol.* 1978, 120, 109.). Together, these peptides along with C3a, C4a, and their des-Arg degradation products, collectively described herein as anaphylatoxin, are capable of triggering diverse inflammatory reactions.

Among the various cell types, the neutrophil response to C5a is the best defined. Cell surface receptors specific for C5a have been demonstrated on the neutrophil (Chenoweth, D. E.; Hugli, T. E. *Proc. Natl. Acad. Sci. U.S.A.* 1978, 75, 3943-3947. Huey, R.; Hugli, T. E. *J. Immunol.* 1985, 135, 2063-2068. Rollins, T. E.; Springer, M. S. *J. Biol. Chem.* 1985, 260, 7157-7160.), and the ligand-receptor interaction promotes human polymorpho-nuclear leukocyte (PMN) migration in a directed fashion (chemotaxis), adherence, oxidative burst, and granular enzyme release from these cells (Hugli, T. E. *Springer Semin. Immunopathol.* 1984, 7, 193-219.). The interaction of C5a with PMN and other target cells and tissues results in increased histamine release, vascular permeability, smooth muscle contraction, and an influx into tissues of inflammatory cells, including neutrophils, eosinophils, and basophils (Hugli, T. E. *Springer Semin. Immunopathol.* 1984, 7, 193-219.). C5a may also be important in mediating inflammatory effects of phagocytic mononuclear cells that accumulate at sites of chronic inflammation (Allison, A. C.; Ferluga, J.; Prydz, H.; Scherlemmer, H. U. *Agents and Actions* 1978, 8, 27.). C5a and C5a des-Arg can induce chemotaxis in monocytes (Ward, P. A. *J. Exp. Med.* 1968, 128, 1201. Snyderman, R.; Shin, H. S.; Dannenberg, A. C. *J. Immunol.* 1972, 109, 896.) and cause them to release lysosomal enzymes (McCarthy, K.; Henson, P. S. *J. Immunol.* 1979, 123, 2511.) in a manner analogous to the neutrophil responses elicited by these agents Recent studies suggest that C5a may have an immunoregulatory role by enhancing antibody particularly at sites of inflammation (Morgan, E. L.; Weigle, W. O.; Hugli, T. E. *J. Exp. Med.* 1982, 155, 1412. Weigle, W. O.; Morgan, E. L.; Goodman, M. G.; Chenoweth, D. E.; Hugli, T. E. *Federation Proc.* 1982, 41, 3099. Morgan, E. L.; Weigle, W. O.; Hugli, T. E. *Federation Proc.* 1984, 43, 2543.).

C5a and C5a des-Arg play important roles in host defenses against bacterial infections and possibly in the mediation of some pathologic lesions such as the leukocyte infiltration seen in the lungs during acute respiratory distress syndrome. This mechanism seems to play a role in different pathological situations like pulmonary distress during hemodialysis, leukophoresis, cardiopulmonary bypass, and in acute myocardial infarction Complement activation has been postulated to play an important pathological role in rheumatoid arthritis, serum sickness, systemic lupus erythematosus, ulcerative colitis, and forms of hepatic cirrhosis, chronic hepatitis, and glomerulonephritis, in certain shock states, during hemodialysis, and cardiopulmonary bypass, acute pancreatitis, myocardial infarction (which may be worsened by C5a-induced leukoembolization following the interaction of complement with atheromatous plaques), asthma, bronchoconstriction, some auto-allergic diseases, transplant rejection, and post-viral encephalopathies.

By serving as antagonists by binding to and blocking the anaphylatoxin receptor, certain compounds of the present invention can reduce or prevent anaphylatoxin-mediated inflammation. Other compounds of the present invention are agonists that mimic anaphylatoxin activity, and assist the body in building its defense mechanism against invasion by infectious agents and malignancy. Additionally, these compounds may influence the immunoregulatory effects of anaphylatoxin. The possible involvement of anaphylatoxin in a wide range of diseases, as indicated by these examples, suggests that anaphylatoxin receptor ligands could have clinical applications for the treatment and prevention of the above-mentioned pathological conditions.

SUMMARY OF THE INVENTION

In accordance with the principal embodiment of the present invention, there are provided anaphylotoxin activity modifying compounds of the formula A-B-D-E-G-J-L-M-Q-T and the pharmaceutically acceptable salts, esters, or amides thereof.

In the generic formula given above, the groups A through T have the following values:

A is $R_1$-$R_2$-$R_3$;

B is selected from $R_4$-$R_5$-$R_6$, $R_{31}$, $R_{32}$, $R_{35}$ and $R_{37}$;

D is selected from $R_7$-$R_8$-$R_9$, $R_{31}$, $R_{32}$, $R_{35}$ and $R_{37}$;

E is selected from $R_{10}$-$R_{11}$-$R_{12}$, $R_{31}$, $R_{32}$, $R_{35}$ and $R_{37}$;

G is selected from $R_{13}$-$R_{14}$-$R_{15}$, $R_{31}$, $R_{32}$, $R_{35}$ and $R_{37}$;

J is selected from $R_{16}$-$R_{17}$-$R_{18}$, $R_{31}$, $R_{32}$, $R_{35}$ and $R_{37}$;

L is selected from $R_{19}$-$R_{20}$-$R_{21}$, $R_{31}$, $R_{32}$, $R_{35}$ and $R_{37}$;

M is selected from $R_{22}$-$R_{23}$-$R_{24}$, $R_{31}$, $R_{32}$, $R_{35}$ and $R_{37}$;

Q is selected from $R_{25}$-$R_{26}$-$R_{27}$, $R_{31}$, $R_{32}$, $R_{35}$ and $R_{37}$;

T is $R_{28}$-$R_{29}$-$R_{30}$;

B and D, taken together, optionally represent a group selected from $R_{33}$, $R_{34}$, $R_{38}$, $R_{39}$, $R_{40}$, $R_{41}$, $R_{42}$, and $R_{43}$;

D and E, taken together, optionally represent a group selected from $R_{33}$, $R_{34}$, $R_{38}$, $R_{39}$, $R_{40}$, $R_{41}$, $R_{42}$, and $R_{43}$;

E and G, taken together, optionally represent a group selected from $R_{33}$, $R_{34}$, $R_{38}$, $R_{39}$, $R_{40}$, $R_{41}$, $R_{42}$, and $R_{43}$;

G and J, taken together, optionally represent a group selected from $R_{33}$, $R_{34}$, $R_{38}$, $R_{39}$, $R_{40}$, $R_{41}$, $R_{42}$, and $R_{43}$;

J and L, taken together, optionally represent a group selected from $R_{33}$, $R_{34}$, $R_{38}$, $R_{39}$, $R_{40}$, $R_{41}$, $R_{42}$, and $R_{43}$;

L and M, taken together, optionally represent a group selected from $R_{33}$, $R_{34}$, $R_{38}$, $R_{39}$, $R_{40}$, $R_{41}$, $R_{42}$, and $R_{43}$; and M and Q, taken together, optionally represent a group selected from $R_{33}$, $R_{34}$, $R_{38}$, $R_{39}$, $R_{40}$, $R_{41}$, $R_{42}$, and $R_{43}$, and one or more of the groups $R_5$-$R_6$-$R_7$; $R_8$-$R_9$-$R_{10}$; $R_{11}$-$R_{12}$-$R_{13}$; $R_{14}$-$R_{15}$-$R_{16}$; $R_{17}$-$R_{18}$-$R_{19}$; $R_{20}$-$R_{21}$-$R_{22}$; $R_{23}$-$R_{24}$-$R_{25}$; or $R_{26}$-$R_{27}$-$R_{28}$, independently optionally represent $R_{36}$.

The group $R_1$ is selected from the group consisting of amino, (lower alkyl)amino, dialkylamino, (arylalkyl)amino, hydroxy, alkoxy, aryloxy, arylalkoxy, acetamido, thioalkoxy, halogen, aryl, lower alkyl, arylalkyl, (heterocyclic)alkyl, heterocyclic, arylamino, and hydrogen.

$R_2$ is selected from the group consisting of $>CR_{99}R_{100}$, $>C=CR_{95}R_{96}$, existing in either the Z- or E-configuration, oxygen, amino, and alkylamino, with the proviso that when $R_2$ is oxygen, amino or alkylamino, $R_1$ is aryl, lower alkyl, arylalkyl or (heterocyclic)alkyl.

$R_3$ is selected from the group consisting of $>C=O$, $>CH_2$, $>C=S$, and $>SO_2$, with the proviso that when $R_3$ is $>CH_2$ or $>SO_2$ then $R_2$ cannot be oxygen, amino or alkylamino.

$R_4$ is selected from the group consisting of $>CH_2$, $>O$, $>S$, and $>NR_{101}$ where $R_{101}$ is hydrogen, lower alkyl, arylalkyl, alkenyl, hydroxy or alkoxy, with the proviso that when $R_4$ is $>O$ or $>S$ then $R_1$, $R_2$ and $R_3$ taken together represent a group selected from lower alkyl, arylalkyl, aryl or hydrogen.

$R_5$ is selected from the group consisting of $>CR_{201}R_{202}$, $>NR_{203}$, $>C=CR_{205}R_{206}$, existing in either the Z- or E-configuration, and substituted cyclopropyl of the formula

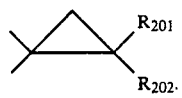

$R_6$, $R_9$, $R_{12}$, $R_{15}$, $R_{18}$, $R_{21}$, and $R_{24}$ are independently selected from the group consisting of $>C=O$, $>CH_2$, $-CH_2C(O)-$, $-NHC(O)-$, $>C=S$, $>SO_2$, and $>P(O)X$ where X is selected from hydroxy, alkoxy, amino, alkylamino and dialkylamino.

$R_7$, $R_{10}$, $R_{13}$, $R_{16}$, $R_{19}$, $R_{22}$, $R_{25}$ are independently selected from $>CH_2$ and $>NR_{50}$ where $R_{50}$ is selected from the group consisting of hydrogen, lower alkyl, arylalkyl, aryl, hydroxy and alkoxy.

$R_8$ is selected from the group consisting of $>CR_{210}R_{211}$, $>NR_{213}$, $>C=CR_{215}R_{216}$, existing in either the Z- or E-configuration, and substituted cyclopropyl of the formula

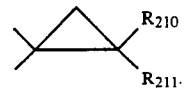

$R_{11}$ is selected from the group consisting of $>CR_{220}R_{221}$, $>NR_{223}$, $>C=CR_{225}R_{226}$, existing in either the Z- or E-configuration, and substituted cyclopropyl of the formula

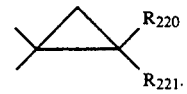

$R_{14}$ is selected from the group consisting of $>CR_{230}R_{231}$, $>NR_{233}$, $>C=CR_{235}R_{236}$, existing in either the Z- or E-configuration, and substituted cyclopropyl of the formula

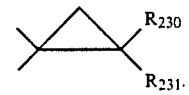

$R_{17}$ is selected from the group consisting of $>CR_{301}R_{302}$, $>NR_{303}$, $>C=CR_{305}R_{306}$, existing in either the Z- or E-configuration, and substituted cyclopropyl of the formula

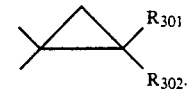

$R_{20}$ is selected from the group consisting of $>CR_{310}R_{311}$, $>NR_{313}$, $>C=CR_{315}R_{316}$, existing in either the Z- or E-configuration, and substituted cyclopropyl of the formula

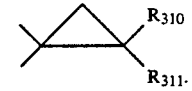

$R_{23}$ is selected from the group consisting of $>CR_{320}R_{321}$, $>NR_{323}$, $>C=CR_{325}R_{326}$, existing in either the Z- or E-configuration, and substituted cyclopropyl of the formula

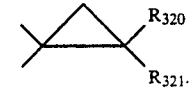

$R_{26}$ is selected from the group consisting of $>CR_{330}R_{331}$, $>C=CR_{335}R_{336}$, existing in either the Z- or E-configuration, and substituted cyclopropyl of the formula

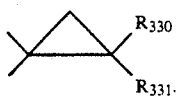

$R_{27}$ is selected from the group consisting of >C=O, >CH$_2$, —CH$_2$C(O)—, >C=S, >SO$_2$, and >P(O)X where X is selected from hydroxy, alkoxy, amino, alkylamino and dialkylamino.

$R_{28}$ is selected from the group consisting of >O, >S, >CH$_2$, and >NR$_{109}$ where R$_{109}$ is selected from hydrogen, lower alkyl, (heterocyclic)alkyl, and arylalkyl, with the proviso that when $R_{27}$ is >SO$_2$ or >P(O)X, then $R_{28}$ is >O or >NR$_{109}$.

$R_{29}$ is selected from the group consisting of hydrogen, lower alkyl, arylalkyl, and >NR$_{110}$ where R$_{110}$ is selected from hydrogen, lower alkyl, aryl, and arylalkyl, with the provisos that (i) when R$_8$ is >O or >S then $R_{29}$ is lower alkyl or arylalkyl, and (ii) when $R_{29}$ is hydrogen, lower alkyl, or arylalkyl then R$_3$ is absent.

$R_{30}$ is selected from the group consisting of hydrogen, aryl, lower alkyl, and arylalkyl.

$R_{31}$ is a group having the structure

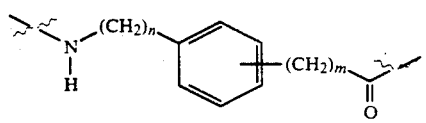

where m and n are integers independently selected from 0, 1 and 2.

$R_{32}$ is a group having the structure

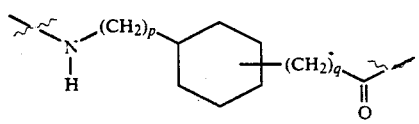

where p and q are integers independently selected from 0, 1 and 2.

$R_{33}$ is a group having the structure

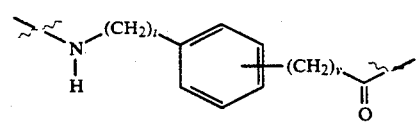

where t and v are integers independently selected from 0, 1, 2 and 3.

$R_{34}$ is a group having the structure

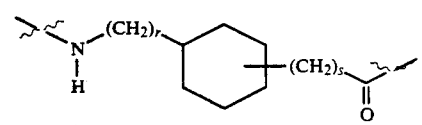

where r and s are integers independently selected from 0, 1, 2 and 3.

$R_{35}$ is a group having the structure

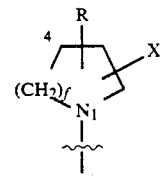

where f is and integer of 0 to 3, X is selected from >C=O and —CH$_2$—. R is selected from hydrogen and lower alkyl, with the provisos that (i) when f is 0, X is at C-2 and R is at C-3 or C-4; (ii) when f is 1, X is at C-2 and R is at C-3, C-4 or C-5 and C-3,4 are saturated or unsaturated; (iii) when f is 2, X is at C-2, C-3 or C-4 and R is at C-2, C-3, C-4, C-5 or C-6 when the position is unoccupied by X and C-3,4 or C-4,5 are saturated or unsaturated; and (iv) when f is 3, X is at C-2, C-3 or C-4 and R is at C-2, C-3, C-4, C-5, C-6 or C-7 when the position is unoccupied by X and C-3,4 or C-4,5 or C-5,6 are saturated or unsaturated.

$R_{36}$ is a group having the structure

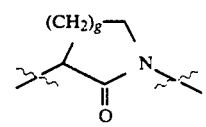

where g is an integer of from 0 to 3.

$R_{37}$ is a group having the structure

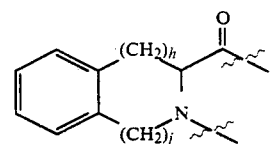

where h is 0 or 1 and j is 0 or 1 with the proviso that either h or j must be 1.

$R_{38}$ is a group having the structure

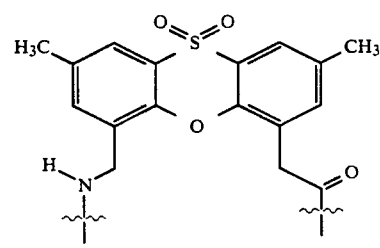

$R_{39}$ is a group having the structure

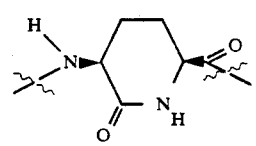

$R_{40}$ is a divalent group having the structure

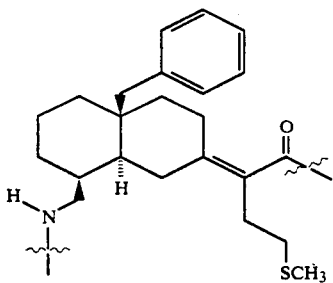

$R_{41}$ is a divalent group having the structure

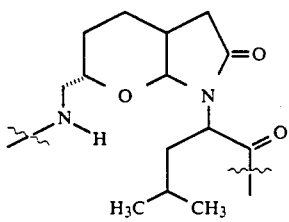

$R_{42}$ is a divalent group having the structure

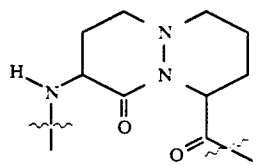

$R_{43}$ is a divalent group having the structure

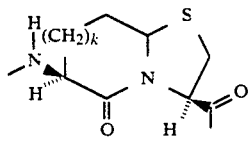

where k is an integer of from zero to two.

$R_1$ and $R_2$, taken together, optionally may represent a group selected from aryl, heterocyclic, or hydrogen.

$R_6$ and $R_7$; $R_9$ and $R_{10}$; $R_{12}$ and $R_{13}$; $R_{15}$ and $R_{16}$; $R_{18}$ and $R_{19}$; $R_{21}$ and $R_{22}$; and $R_{24}$ and $R_{25}$; each pair taken together, may optionally and independently represent a group selected from $>CH_2$, $-(CH_2)_3-$, $-CH=CH-$, $-C\equiv C-$, $-C(=CH_2)CH_2-$, $-CH(OH)CH_2-$, $-C(O)O-$, $-C(O)S-$, $-CH_2C(O)O-$, $-CH_2C(O)S-$, $-CH_2O-$, $-CH_2S-$, and $-NHC(O)-$; with the provisos that (i) when $R_5$ is $>NR_{203}$ or $>C=CR_{205}R_{206}$, $R_6$ and $R_7$, taken together, represent $-C(O)NH-$ or $-C(O)NCH_3-$; (ii) when $R_8$ is $>NR_{213}$ or $>C=CR_{215}R_{216}$, $R_9$ and $R_{10}$, taken together, represent $-C(O)NH-$ or $-C(O)NCH_3-$; (iii) when $R_{11}$ is $>NR_{223}$ or $>C=CR_{225}R_{226}$, $R_{12}$ and $R_{13}$, taken together represent $-CONH-$ or $-CONCH_3-$; (iv) when $R_{14}$ is $>NR_{233}$ or $>C=CR_{235}R_{236}$, $R_{15}$ and $R_{16}$, taken together, represent $-C(O)NH-$ or $-C(O)NCH_3-$; (v) when $R_{17}$ is $>NR_{303}$ or $>C=CR_{305}R_{306}$, $R_{18}$ and $R_{19}$, taken together, represent $-C(O)NH-$ or $-C(O)NCH_3-$; (vi) when $R_{20}$ is $>NR_{313}$ or $>C=CR_{315}R_{316}$, $R_{21}$ and $R_{22}$, taken together, represent $-CONH-$ or $-CONCH_3-$; (vii) when $R_{23}$ is $>NR_{323}$ or $>C=CR_{325}R_{326}$, $R_{24}$ and $R_{25}$, taken together, represent $-C(O)NH-$ or $-C(O)NCH_3-$.

$R_{29}$ and $R_{30}$, taken together, optionally represent a group selected from hydrogen, hydroxy, or alkoxy, with the proviso that when $R_{28}$ is $>O$ or $>S$ then $R_{29}$ and $R_{30}$, taken together, represent hydrogen.

$R_1$, $R_2$ and $R_3$, taken together, optionally represent a group selected from lower alkyl, arylalkyl, alkenyl, aryl, hydroxy, alkoxy, hydrogen, an N-terminal protecting group or peptide fragment of 1-8 residues similarly protected wherein each of the amino acids comprising the peptide fragment is independently selected from the 20 naturally occuring amino acids.

$R_1$, $R_2$, $R_3$ and $R_4$, taken together, optionally represent a group selected from hydrogen, lower alkyl, arylalkyl, aryl, heterocyclic, or $H_2NC(O)-$, with the proviso that when $R_5$ is $>CH_2$ then $R_1$, $R_2$, $R_3$ and $R_4$, taken together, may not be hydrogen.

$R_{27}$, $R_{28}$, $R_{29}$ and $R_{30}$, taken together, optionally represent a group selected from hydrogen, lower alkyl, aryl, or arylalkyl.

$R_1$, $R_2$, $R_3$, $R_4$ and $R_5$, taken together, optionally represent an aryl or heterocyclic group.

$R_{95}$, $R_{96}$, $R_{205}$, $R_{206}$, $R_{215}$, $R_{216}$, $R_{225}$, $R_{226}$, $R_{235}$, $R_{236}$, $R_{305}$, $R_{306}$, $R_{315}$, $R_{316}$, $R_{335}$ and $R_{336}$ are independently selected from the group consisting of hydrogen, lower alkyl, aryl, arylalkyl, (cycloalkyl)alkyl, amidoalkyl, (carboxyamido)alkyl, ureidoalkyl, (heterocyclic)alkyl, and halosubstituted alkyl.

$R_{99}$, $R_{202}$, $R_{211}$, $R_{231}$, $R_{302}$, $R_{311}$, $R_{321}$ and $R_{331}$ are independently selected from hydrogen and lower alkyl.

$R_{100}$ is selected from the group consisting of hydrogen, lower alkyl, arylalkyl, (cycloalkyl)alkyl, aminoalkyl, (alkylamino)alkyl, hydroxyalkyl, guanidinoalkyl, carboxyalkyl, (heterocyclic)alkyl, (thioalkoxy)alkyl, arylalkoxy, and sulfhydrylalkyl.

$R_{201}$ is selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, sulfhydrylalkyl, (aminothioalkoxy)alkyl, (thioarylalkoxy)alkyl, protected sulfhydrylalkyl, and halosubstituted alkyl.

$R_{203}$, $R_{213}$, $R_{223}$, $R_{303}$, and $R_{313}$ are independently selected from the group consisting of hydrogen, lower alkyl, alkenyl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, sulfhydrylalkyl, (aminothioalkoxy)alkyl, (thioarylalkoxy)alkyl, or protected sulfhydrylalkyl with the proviso that none of the groups $R_{203}$, $R_{213}$, $R_{223}$, $R_{233}$, $R_{303}$, or $R_{313}$ may be a vinyl group or have a heteroatom directly attached to the nitrogen or separated from it by one methylene unit.

$R_{210}$ is hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, ureidoalkyl, (carboxyhydrazino)alkyl, (heterocyclic)alkyl, (thioalkoxy)alkyl, sulfhydrylalkyl, (aminothioalkoxy)alkyl, (thioarylalkoxy)alkyl, protected sulfhydrylalkyl, or halosubstituted alkyl.

$R_{220}$, $R_{230}$, $R_{301}$, $R_{310}$, and $R_{330}$ are independently selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, sulfhydrylalkyl, (aminothioalkoxy)alkyl, (thioarylalkoxy)alkyl, protected sulfhydrylalkyl, or halosubstituted alkyl.

$R_{320}$ and $R_{323}$ are selected from the group consisting of hydrogen, lower alkyl, alkenyl, aryl, benzyl, (cycloalkyl)alkyl, -(alkylene)-C(O)NR$_{340}$R$_{341}$, -(alkylene)-NR$_{342}$R$_{343}$, -(alkylene)-NR$_{344}$C(O)R$_{345}$, hydroxyalkyl, -(alkylene)-NR$_{342}$R$_{343}$, -(alkylene)-NR$_{344}$C(O)R$_{345}$, hydroxyalkyl, guanidinoalkyl, carboxyalkyl, (carboxyhydrazino)alkyl, ureidoalkyl, heterocyclic substituted methyl, (thioalkoxy)alkyl, sulfhydrylalkyl, (aminothioalkoxy)alkyl, protected sulfhydrylalkyl, and halosubstituted alkyl, where $R_{340}$, $R_{341}$, $R_{342}$, and $R_{343}$ are independently selected from hydrogen and lower alkyl, and $R_{344}$ and $R_{345}$ are independently selected from hydrogen, lower alkyl, and halosubstituted lower alkyl, with the proviso that $R_{323}$ may not be a vinyl group or have a heteroatom directly attached to the nitrogen or separated from it by one methylene unit.

$R_{325}$ and $R_{326}$ are independently selected from the group consisting of hydrogen, lower alkyl, aryl, (cycloalkyl)alkyl, -(alkylene)-NR$_{344}$C(O)R$_{345}$, (carboxyamido)alkyl, ureidoalkyl, (heterocyclic)alkyl, and halosubstituted alkyl, where $R_{344}$ and $R_{345}$ are as defined above.

$R_{201}$ and $R_{202}$, $R_{210}$ and $R_{211}$, $R_{220}$ and $R_{221}$, $R_{230}$ and $R_{231}$, $R_{301}$ and $R_{302}$, $R_{310}$ and $R_{311}$, $R_{320}$ and $R_{321}$, and $R_{330}$ and $R_{331}$, each pair taken together, independently may optionally represent —(CH$_2$)$_z$— where z is an integer of from 2 to 6.

All of the foregoing definitions are with the provisos that, in the compounds of the present invention, (i) when more than one sulfhydrylalkyl is present in the compound, the compound exists in the oxidized disulfide form producing a cyclic molecule, or the two sulfhydryl moieties are connected by a C$_2$ to C$_8$ alkylene chain and (ii) when the compound contains a free amino group and carboxyl group, they can be cyclized to give the corresponding lactam.

DETAILED DESCRIPTION

As discussed above, C5a is the most active of a class of biologically active peptides which serves to amplify and exacerbate inflammation. While C5a contains 74 amino acid residues, it has been found in accordance with the present invention that oligopeptides containing as few as eight amino acid residues are also actively bound by C5a receptors. Moreover, it has been found that peptidomimetic compounds (i.e. compounds which mimic the activity of peptides) in which certain groups replace the α-carbon, carbonyl group, and amide-nitrogen group of the individual amino acids in oligopeptides are also actively bound by C5a receptors.

The chemical structures of the compounds of the present invention are best understood by reference to the following structural formula in which it is understood that the segments are joined serially at the free valence bonds to form the compound A-B-D-E-G-J-L-M-Q-T.

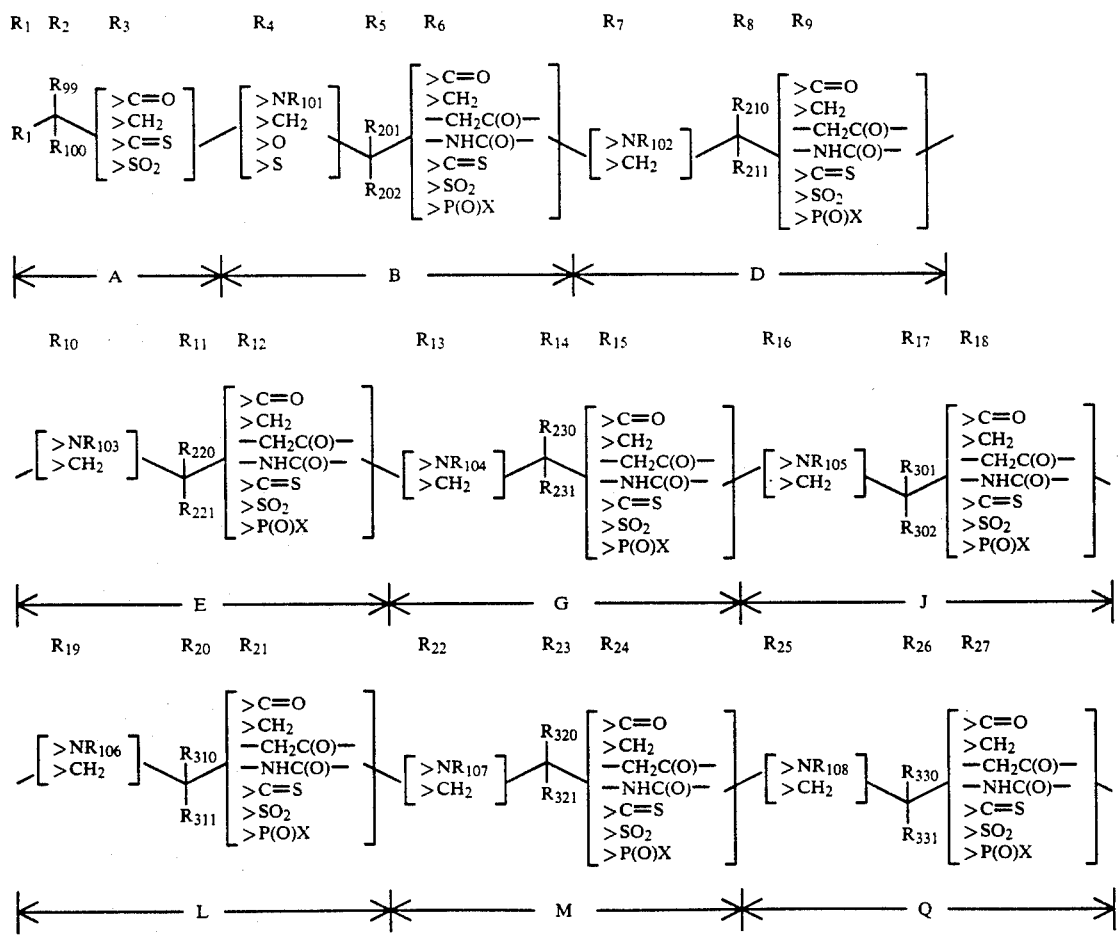

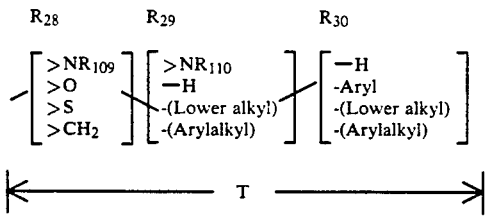

As used throughout this specification and the appended claims, the following terms have the meanings specified.

The term "alkyl" as used herein refers to monovalent straight chain or branched chain groups of 1 to 12 to carbon atoms, including, but not limited to methyl, ethyl, n-propyl, isopropyl, n-butyl, sec-butyl, isobutyl, tert-butyl, and the like.

The term "lower alkyl" as used herein refers to straight or branched chain alkyl groups containing from 1 to 8 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "alkylene" as used herein refers to divalent groups of from one to twelve carbon atoms derived by the removal of two hydrogen atoms from straight or branched saturated hydrocarbons. Examples include —CH$_2$—, —CH(CH$_3$)—, —C(CH$_3$)$_2$—, —CH(C$_2$H$_5$)—, —CH$_2$CH$_2$—, —CH$_2$CH(CH$_3$)—, —C(CH$_3$)$_2$C(CH$_3$)$_2$—, —CH$_2$CH$_2$CH$_2$— and the like.

The term "alkenyl" as used herein refers to straight or branched chain groups of 2 to 12 carbon atoms containing a carbon-carbon double bond, including, but not limited to ethenyl, 1-propenyl, 2-propenyl, 2-methyl-1-propenyl, 1-butenyl, 2-butenyl, and the like.

The term "halosubstituted alkyl" refers to an alkyl group as described above substituted with one or more halogens, including, but not limited to chloromethyl, trifluoromethyl, 2,2,2-trichloroethyl, and the like. The terms "halo" and "halogen" are used herein to mean groups derived from the elements fluorine, chlorine, bromine, or iodine.

The term "cycloalkyl" as used herein refers to cyclic groups, of 3 to 8 carbons, including, but not limited to cyclopropyl, cyclobutyl, cyclopentyl, cyclohexyl, and the like.

The term "(cycloalkyl)alkyl" as used herein refers to a cycloalkyl group appended to a lower alkyl group, including, but not limited to cyclohexylmethyl and cyclohexylethyl.

The term "alkoxy" as used herein refers to an alkyl group as defined above, attached to the remainder of the molecule through an oxygen atom. Alkoxy groups include, for example, methoxy, ethoxy, isopropoxy, n-butoxy, sec-butoxy, isobutoxy, tert-butoxy, and the like.

The term "sulfhydrylalkyl" as used herein refers to a —SH group appended to a lower alkyl group, as previously defined.

The term "protected sulfhydrylalkyl" refers to a sulfhydrylalkyl group, as previously defined, which has been transformed to the corresponding S-acetamidomethyl (S-Acm) or other similar protecting group, including, but not limited to S-phenacetamidomethyl.

The term "thioalkoxy" as used herein refers to an alkyl group, as previously defined, attached to the remainder of the molecule through a sulfur atom. Examples of thioalkoxy groups include, but are not limited to, thiomethoxy, thioethoxy, thioisopropoxy, n-thiobutoxy, sec-thiobutoxy, isothiobutoxy, tert-thiobutoxy and the like.

The term "(thioalkoxy)alkyl" as used herein refers to a thioalkoxy group, as just defined, appended to a lower alkyl group.

The term "(thioarylalkoxy)alkyl" as used herein refers to a group of the structure R$_{420}$—S— appended to a lower alkyl where R$_{420}$ is an arylalkyl group as defined below.

The term "aryl" as used herein refers to substituted and unsubstituted carbocyclic aromatic groups including, but not limited to phenyl, 1- or 2-naphthyl, fluorenyl, (1,2)-dihydronaphthyl, (1,2,3,4)-tetrahydronaphthyl, indenyl, indanyl, and the like, wherein the aryl group may be substituted with 1, 2, or 3 substituents independently selected from halo, nitro, cyano, C$_1$ to C$_{12}$ alkyl, alkoxy aroyl and halosubstituted alkyl.

The term "arylalkyl" as used herein refers to an aryl group, as previously defined, appended to an alkyl group, including, but not limited to benzyl, 1- and 2-naphthylmethyl, halobenzyl, alkoxybenzyl, hydroxybenzyl, aminobenzyl, nitrobenzyl, guanidinobenzyl, phenylmethyl(benzyl), 1-phenylethyl, 2-phenylethyl, 1-naphthylethyl, and the like.

The term "benzyl" as used herein refers specifically to to phenyl substituted methyl in which the phenyl group may be substituted with 1, 2, or 3 substituents independently selected from halo, nitro, cyano, alkyl of from one to twelve carbon atoms, alkoxy, aroyl, and halosubstituted alkyl, and the like.

The term "aryloxy" as used herein refers to an aryl group as previously defined, attached to the parent molecular moiety through an oxygen atom. Aryloxy includes, but is not limited to phenoxy, 1-naphthoxy, 2-naphthoxy and the like.

The term "arylalkoxy" as used herein refers to an arylalkyl group as previously defined, attached to the parent molecular moiety through an oxygen atom. Arylalkoxy includes, but is not limited to benzyloxy, 2-phenethyloxy, 1-naphthylmethyloxy and the like.

The term "aroyl" as used herein refers to an aryl group as defined above, attached to the parent molecule through a carbonyl group. Examples include benzoyl and substituted benzoyl.

The term "alkylamino" as used herein refers to a group having the structure —NH(alkyl) where the alkyl portion is as defined above. Alkylamino groups include, for example, methylamino, ethylamino, isopropylamino and the like.

The term "dialkylamino" as used herein refers to a group having the structure —N(alkyl)(alkyl) where the two alkyl groups may be the same or different and are as previously defined.

The term "aminoalkyl" as used herein refers to a group having the structure $-NR_{342}R_{343}$ appended to a lower alkyl group, as previously defined. The groups $R_{342}$ and $R_{343}$ are independently selected from hydrogen, lower alkyl, aryl and arylalkyl. Additionally, $R_{342}$ and $R_{343}$ taken together, may optionally be $-(CH_2)_{mm}-$ where mm is an integer of from 2 to 6.

The term "amidoalkyl" as used herein refers to a group having the structure $-NR_{344}C(O)R_{345}$ appended to a lower alkyl group, as previously defined. The groups $R_{344}$ and $R_{345}$ are independently selected from hydrogen, lower alkyl, aryl, arylalkyl, and halosubstituted alkyl. Additionally, $R_{344}$ and $R_{345}$ taken together may optionally be $-(CH_2)_{kk}-$ where kk is an integer of from 2 to 6.

The term "(aminothioalkoxy)alkyl" as used herein refers to $H_2N-R_x-S-R_y-$ where Rx and Ry are alkylene groups, as previously defined, and may be the same or different.

The term "carboxyalkyl" as used herein refers to a carboxyl group, $-CO_2H$, appended to a lower alkyl group, as previously defined.

The term "(carboxyamido)alkyl" as used herein refers to a group of the formula $-C(O)NR_{340}R_{341}$, appended to a lower alkyl group, as previously defined. The groups $R_{340}$ and $R_{341}$ are independently selected from hydrogen, lower alkyl, aryl and arylalkyl. Alternatively, $R_{340}$ and $R_{341}$ taken together may optionally be $-(CH_2)_{pp}-$ wherein pp is an integer of from 2 to 6.

The term "(carboxyhydrazino)alkyl" as used herein refers to a group having the structure $-C(O)NR_{425}NHR_{430}$ appended to a lower alkyl group, as previously defined. The groups $R_{425}$ and $R_{430}$ are independently selected from hydrogen, lower alkyl, aryl and arylalkyl.

The term "guanidinoalkyl" as used herein refers to a group of the structure $-NR_{346}C(=NR_{347})NHR_{348}$ appended to a lower alkyl group, as previously defined. $R_{346}$, $R_{347}$, and $R_{348}$ are independently selected from hydrogen, lower alkyl, and aryl.

The term "ureidoalkyl" as used herein refers to a group having the structure $-NHC(O)NH_2$ appended to a lower alkyl group, as previously defined.

The term "heterocyclic" as used herein refers to any 5- or 6-membered ring containing from one to three heteroatoms independently selected from the group consisting of nitrogen, oxygen, and sulfur, wherein the 5-membered ring has 0 to 2 double bonds and the 6-membered ring has 0 to 3 double bonds, wherein the nitrogen and sulfur heteroatoms may optionally be oxidized, wherein the nitrogen heteroatom may optionally be quaternized, and including any bicyclic group in which any of the above heterocyclic rings is fused to a benzene ring. Representative heterocycles include, but are not limited to pyrrolyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazoyl, oxazolidinyl, isoxazolyl, isoxazolidinyl, morpholinyl, indolyl, quinolinyl, thiazolyl, thiazolidinyl, isothiazolyl, isothiazolidinyl, isoquinolinyl, benzimidazolyl, benzothiazolyl, benzoxazolyl, furyl, thienyl, and benzothienyl.

The term "(heterocyclic)alkyl" as used herein refers to a heterocyclic group, as previously defined, appended to an alkyl group as previously defined.

The term "hydroxyalkyl" as used herein refers to —OH appended to a lower alkyl group.

The term "naturally occuring amino acid" refers to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The term "N-terminal protecting group" refers to those groups intended to protect the N-terminus against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), carbobenzyloxycarbonyl (Cbz), benzoyl groups or an L- or D-aminoacyl residue, which may itself be N-protected similarly.

The term "anaphylatoxin" is used herein to mean C5a, C4a, C3a, or the corresponding des-Arg degradation products.

The term "pharmaceutically acceptable salt" refers to non-toxic acid addition salts such as salts formed with inorganic acids such as hydrochloric acid, hydrobromic acid, phosphoric acid, sulfuric acid and perchloric acid or with organic acids such as acetic acid, oxalic acid, maleic acid, malic acid, tartaric acid, citric acid, succinic acid or malonic acid. Other pharmaceutically acceptable salts include inorganic nitrate, sulfate, acetate, malate, formate, lactate, tartrate, succinate, citrate, p-toluenesulfonate, and the like, including, but not limited to cations based on the alkali and alkaline earth metals, such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Examples of pharmaceutically acceptable, non-toxic esters of the compounds of this invention include $C_1$ to $C_6$ alkyl esters wherein the alkyl group is straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compound of formula I may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compound of formula I may be prepared according to conventional methods.

Numerous asymmetric centers may exist in the compounds of the present invention. The present invention contemplates the various stereoisomers and mixtures thereof. In particular, chiral centers Can exist at $R_2$, $R_5$, $R_8$, $R_{11}$, $R_{14}$, $R_{17}$, $R_{20}$, $R_{23}$ and $R_{26}$. When these groups comprise the α-carbon atom of an α-amino acid, the natural configuration is preferred. However, compounds of the present invention containing up to three α-amino acid residues of non-natural configuration have also been found to be effective as modulators of anaphylotoxin activity.

Particular stereoisomers are prepared by selecting the starting amino acids or amino acid analogs having the desired stereochemistry and reacting these starting materials by the methods detailed below. Starting compounds of particular stereochemistry are either commercially available or are made by the methods detailed below and resolved by techniques well known in the organic chemical arts.

One class of preferred compounds of the present invention are those in which the groups $R_4$, $R_7$, $R_{10}$, $R_{13}$, $R_{16}$, $R_{19}$, $R_{22}$, and $R_{25}$ are independently selected from >NH and >N—(lower alkyl).

In another class of preferred compounds of the present invention, the groups $R_6$, $R_9$, $R_{12}$, $R_{15}$, $R_{18}$, $R_{21}$, $R_{24}$, and $R_{27}$ are independently selected from >C=O and >CH$_2$.

The group $R_5$ is preferably selected from >CR$_{201}$R$_{202}$; >NR$_{203}$; >C=CR$_{205}$R$_{206}$, existing in the Z- or E-configuration; and substituted cyclopropyl of the formula

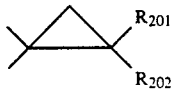

where $R_{201}$ is selected from lower alkyl, alkenyl, aryl, arylalkyl, (cycloalkyl)alkyl, amidoalkyl, (carboxyamido)alkyl, (heterocyclic)alkyl, (thioalkoxy)alkyl, (thioarylalkoxy)alkyl, protected sulfhydrylalkyl, and halosubstituted alkyl. $R_{202}$ and $R_{205}$ are selected from the group consisting of hydrogen and lower alkyl; $R_{203}$ is selected from the group consisting of lower alkyl, alkenyl, arylalkyl, (cycloalkyl)alkyl, amidoalkyl, (carboxyamido)alkyl, (heterocyclic)alkyl, (thioalkoxy)alkyl, (thioarylalkoxy)alkyl, and protected sulfhydrylalkyl, with the proviso that $R_{203}$ may not be a vinyl group or have a heteroatom directly attached to the nitrogen or separated from it by one methylene group. $R_{206}$ is selected from the group consisting of lower alkyl; aryl; arylalkyl; (cycloalkyl)alkyl; amidoalkyl; (carboxyamido)alkyl; (heterocyclic)alkyl; and halosubstituted alkyl.

$R_8$ is preferebly selected from the group consisting of >CR$_{210}$R$_{211}$; >NR$_{213}$; >C=CR$_{215}$R$_{216}$; and substituted cyclopropyl of the formula

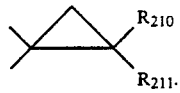

$R_{210}$ is selected from the group consisting of arylalkyl; aminoalkyl; guanidinoalkyl; (heterocyclic)alkyl; (aminothioalkoxy)alkyl. $R_{211}$ and $R_{215}$ selected from hydrogen and lower alkyl; $R_{213}$ is selected from the group consisting of arylalkyl; aminoalkyl; guanidinoalkyl; (heterocyclic)alkyl; and (aminothioalkoxy)alkyl; with the proviso that $R_{213}$ may not have a herteroatom directly attached to the nitrogen or separated from it by one methylene unit; and $R_{216}$ is selected from arylalkyl and (heterocyclic)alkyl.

$R_{26}$ is preferably selected from the group consisting of >CR$_{330}$R$_{331}$; >C=CR$_{335}$R$_{336}$, existing in either the Z- or E-configuration; and substituted cyclopropyl of the formula

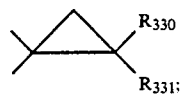

where $R_{335}$ is selected from hydrogen and lower alkyl. $R_{336}$ is selected from arylalkyl and (heterocyclic)alkyl; $R_{330}$ is selected from the group consisting of arylalkyl, aminoalkyl, guanidinoalkyl, (heterocyclic)alkyl and (aminothioalkoxy)alkyl; and $R_{331}$ is hydrogen or lower alkyl.

METHOD OF TREATMENT

The compounds of the present invention serve to modulate the activity of anaphylatoxin. Certain compounds of the present invention function as anaphylatoxin antagonists, while others function as agonists. The antagonist compounds of the present invention block the anaphylatoxin receptor and prevent anaphylatoxin activity, which makes those compounds useful in the treatment and prevention of injurious conditions or diseases in which anaphylatoxin may be involved. Disease states in which anaphylatoxin is involved include asthma, bronchial allergy, chronic inflammation, systemic lupus erythematosus, vasculitis, serum sickness, angioedema, rheumatoid arthritis, osteoarthritis, gout, bullous skin diseases, hypersensitivity pneumonitis, idiopathic pulmonary fibrosis, immune complex-mediated glomerulonephritis, psoriasis, allergic rhinitis, adult respiratory distress syndrome, acute pulmonary disorders, endotoxin shock, hepatic cirrhosis, pancreatitis, inflammatory bowel diseases (including Crohn's disease and ulcerative colitis), thermal injury, Gram-negative sepsis, necrosis in myocardial infarction, leukophoresis, exposure to medical devices (including but not limited to hemodialyzer membranes and extracorpeal blood circulation equipment), chronic hepatitis, transplant rejection, post-viral encephalopathies, and/or ischemia induced myocardial or brain injury. These compounds may also be used as prophylactics for such conditions as shock accompanying Dengue fever. In addition, a combination of antibiotic and anti-inflammatory agent such as corticosteroids (e.g., methylprednisolone) and one or more of the above mentioned compounds may be employed.

Certain compounds of the invention are useful therapeutic agents because of their ability to mimic or promote anaphylatoxin activity and are therefore useful in stimulating the inflammatory response and immune response in mammals who are deficient in this regard. These agonist compounds may be used to assist the body in building its defense mechanism against invasion by infectious microorganisms or other stress. Interaction by these agonists at the anaphylatoxin receptor makes them useful in treating conditions or diseases including, but not limited to cancers (including but not limited lung carcinoma), immunodeficiency diseases, and severe infections.

In some cases this will involve preventing the underlying cause of the disease state and in other cases, while the underlying disease will not be affected, the compounds of this invention will have the benefit of ameliorating the symptoms or preventing the manifestations of the disease.

The compounds of the present invention may be administered orally, parenterally, by inhalation spray, rectally, or topically in dosage unit formulations containing conventional nontoxic pharmaceutically acceptable carriers, adjuvants and vehicles as desired.

The term "parenteral" as used herein includes subcutaneous, intravenous, intramuscular, intrasternal, intraarterial injection or infusion techniques, without limitation. The term "topically" encompasses administration rectally and by inhalation spray, as well as by the more common routes of the skin and the mucous membranes of the mouth and nose.

Actual dosage levels of active ingredients in the pharmaceutical compositions of this invention may be varied so as to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 mg to about 100 mg, more typically from about 0.1 mg to about 20 mg, of active compound per kilogram of body weight per day are administered daily to a mammalian host. If desired, the effective daily dose may be divided into multiple doses for purposes of administration, e.g. two to four separate doses per day.

FORMULATION OF PHARMACEUTICAL COMPOSITION

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous cariers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents such as sugars, sodium chloride, and the like, Prolonged absorption of the injectable pharmaceutical form may be brought about by the inclusion of agents which delay abdorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

ANAPHYLATOXIN RECEPTOR BINDING KI DETERMINATION

Specific inhibition of C5a binding activity of representative compounds of the present invention was measured using 0.03-1 nM $^{125}$I-C5a with 2.5-25 μg/mL of purified PMNL membrane fragments (Borregaard, N.; Heiple, J. M.; Simons, E. R.; and Clark, R. A. *J. Cell. Biol.* 1983, 97, 52-61.). Free and membrane-bound ligand were separated by filtration. Binding potencies for representative examples of compounds of this invention are listed in Table 1.

TABLE 1

In vitro C5a Receptor Binding Potency of Compounds of this Invention.

| Example | Ki μM | Example | Ki μM |
|---------|-------|---------|-------|
| 2 | 0.098 | 249 | 0.11 |
| 13 | 0.85 | 279 | 4.0 |
| 23 | 2.4 | 282 | 0.029 |
| 31 | 0.09 | 295 | 3.3 |
| 91 | 0.485 | 296 | 0.012 |
| 106 | 0.042 | 305 | 0.17 |
| 111 | 0.65 | 316 | 0.17 |
| 117 | 0.55 | 338 | 0.5 |
| 131 | 0.17 | 348 | 0.14 |
| 150 | 0.11 | 377 | 1.8 |
| 165 | 0.042 | 402 | 0.011 |
| 182 | 0.3 | 404 | 0.13 |
| 188 | 0.21 | 409 | 3.8 |
| 202 | 0.87 | 421 | 3.2 |
| 213 | 0.33 | 424 | 0.48 |
| 220 | 0.22 | 432 | 0.03 |
| 229 | 0.033 | 445 | 0.26 |
| 245 | 0.052 | 455 | 0.017 |
| 247 | 0.33 | 460 | 0.021 |

SYNTHESIS OF THE COMPOUNDS

The novel compounds and salts thereof of the invention can be utilized effectively as therapeutic agents. Accordingly, the present invention further relates to therapeutic compositions comprising a novel compound having the general formula I or salts thereof as an active component.

The compounds of the invention may be prepared by a synthetic method of elongation of a peptide chain through condensation of one amino acid by one, or by a method of coupling fragments consisting of two or several amino acids, or by a combination of these methods in accordance with conventional peptide synthesis methods.

The condensation of two amino acids, the condensation of an amino acid with a peptide or the condensation of one peptide with another peptide may be effected in accordance with conventional condensation methods such as azide method, mixed acid anhydride method, symmetrical anhydride method, DCC (dicyclohexylcarbodiimide) method, active ester method (p-nitrophenyl ester method, N-hydroxysuccinimide ester method, cyanomethyl ester method and the like), Woodward reagent K method, DCC-HOBT(1-hydroxy-benzotriazole) method and the like. These condensation reactions may be done by either solution methods or solid phase synthetic methods. When the peptide chain is elongated by the solid phase method, the C-terminal amino acid is linked to an insoluble carrier. As the insoluble carrier, any that can produce a detachable bond by reacting with a carboxyl group in a C-terminal amino acid may be used, and the examples thereof involve, for example, halomethyl resins such as chloromethyl resin, bromomethyl resin and the like, hydroxy-methyl resin, benzhydrylamine resin, and t-alkyloxycarbonyl hydrazide resin.

As conventional polypeptide synthesis, branched chain amino and carboxyl groups at alpha and omega positions in amino acids may be protected/deprotected if necessary. The protecting groups for amino groups which can be used involve, for example, benzyloxycarbonyl (Z), o-chlorobenzyloxycarbonyl ((2-Cl)Z), p-nitrobenzyloxycarbonyl (Z(NO$_2$)), p-methoxybenzyloxycarbonyl (Z(OMe)), t-butoxycarbonyl (Boc), t-amyloxycarbonyl (Aoc), isobornyloxycarbonyl, admantyloxycarbonyl, 2-(4-biphenyl)-2-propyloxycarbonyl (Bpoc), 9-fluorenyl-methoxycarbonyl (Fmoc), methylsulfonylethoxycarbonyl (Msc), trifluoroacetyl, phthalyl, formyl, 2-nitrophenylsulfenyl (Nps), diphenylphosphinothioyl (Ppt), and dimethylphosphinothioyl (Mpt).

The examples of protecting groups for carboxyl groups involve, for example, benzyl ester (OBn), cyclohexyl ester, 4-nitrobenzyl ester (OBnNO$_2$), t-butyl ester (OtBu), 4-picolyl ester (OPic) and the like.

In the course of the synthesis of the present novel compounds, specific amino acids having functional groups other than amino and carboxyl groups in the branched chain such as arginine, cysteine, serine, and the like may be protected, if necessary, with suitable protecting group. It is preferable that for example, the guanidino group (N$^G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mds), 1,3,5-trimethylphenylsulfonyl (Mts) and the like, and the thiol group in cysteine may be protected with benzyl, p-methoxybenzyl, triphenylmethyl, acetamidomethyl, ethylcarbamyl, 4-methylbenzyl (4-MeBn), 2,4,6-trimethylbenzyl (Tmb) and the like, and the hydroxyl group in serine may be protected with benzyl (Bn), t-butyl, acetyl, tetrahydropyranyl and the like.

N-Acetylated peptides were prepared in analogy to Example 99. The following literature procedures were used to prepare N-alkyl- or N,N-dialkyl-amino acid derivatives. Lovett, J. A.; Portoghese, P. *J. Med. Chem.* 1987, 30, 1144-1149. Borch, R. F.; Hassid, A. I. *J. Org. Chem.* 1972, 37, 1673-1674. Hansen, D. W.; Pilipauskas, D. *J. Org. Chem.* 1985, 50, 945-950. Grieco, P. A.; Bashas, A. *J. Org. Chem.* 1987, 52, 5746-5749. Shuman, R. T.; Smithwick, E. L.; Smiley, D. L.; Brooke, G. S.; Gesellchen, P. D. "Peptide: Structure and Function", Proceedings of the Eighth American Peptide Symposium, 1984; p 143-146. Cheung, S. T.; Benoiton, N. L. *Can. J. Chem.* 1977, 55, 906-910. These reactions were carried out either on the elongated peptide-resin or on amino acid derivatives and then incorporated into the peptide-resin.

The following literature procedures were used to prepare (2'S,3S)-3-amino-2-oxo-1-pyrrolidine-(2'-(4'-methyl)}-pentanoic acid, (2'R,3S)-3-amino-2-oxo-1-pyrrolidine-(2'-(4'-methyl)}-pentanoic acid, and (2'R/S,3S)-3-amino-2-oxo-1-azepine-2'-pentanoic acid: Freidinger, R. M.; Perlow, D. S.; Veber, D. F. *J. Org. Chem.* 1982, 47, 104–109. The preparation of (2R,S)-2-amino-5-phenylpentanoic acid is described in: Greenstein, J. P.; Winitz, M. "Chemistry of the Amino Acids"; John Wiley and Sons, Inc.: New York, 1961; vol III, p.2387. Perhydroindolecarboxylic acid was synthesized according to the following procedure: Vincent, M.; Remond, G.; Portevin, B.; Serkiz, B.; Laubie, M. *Tetrahedron Lett.* 1982, 23, 1677–1682.

(2S)-2-Amino-4-cyclohexylbutanoic acid: A solution of (2S)-2-amino-4-phenylbutanoic acid (5 g) in 10% HOAc-H$_2$O (50 mL) was hydrogenated at room temperature at 5 atms with platinum oxide (0.1 g). Removal of catalyst by filtration and evaporation yielded 4.9 g of product. 3-(2'-Perhydronaphthyl)alanine and 3-(1'-perhydronaphthyl)alanine were prepared similarly from L-3-(2'-naphthyl)alanine and L-3-(1'-naphthyl)alanine, respectively.

The following literature procedures were used to prepare N-guanidino substituted arginine derivatives: Mathias, L. J., *Synthesis* 1979, 561–576; Maryanoff, C. A.; Stanzione, R. C.; Plampin; J. M.; Mills, J. E. *J. Org. Chem.* 1986, 51, 1882–1884; Nestor, J. J.; Ho, T. L.;Simpson, R. A.; Horner, B. L.; Jones, G. H.; McRae, G. I.; Vickery, B. H. *J. Med. Chem.* 1982, 25, 795–801. The obtained arginine derivatives were attached to Merrifield resin as described in: Stewart, J. M.; Young, J. D."Solid Phase Peptide Synthesis", 2nd edition; Pierce Chemical Co.: Rockford, Ill., 1984; p 71–72. The amino acid resin obtained was used to construct the peptide, followed by cleavage and purification to yield the desired peptide analog.

The following fragments are prepared as described in the literature:

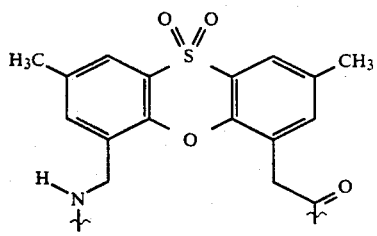
Fragment-1

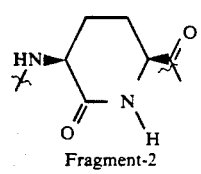
Fragment-2

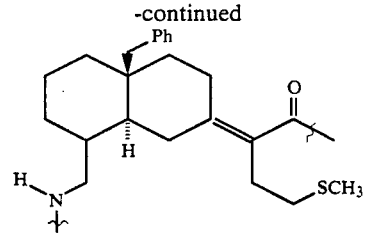
Fragment-3

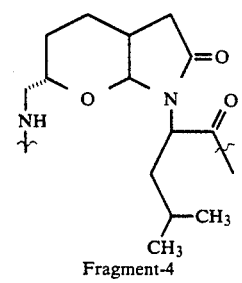
Fragment-4

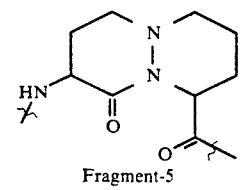
Fragment-5

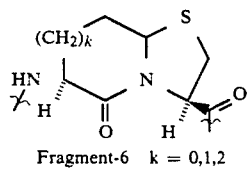
Fragment-6  k = 0,1,2

References

1. Fiegel, M. *J. Am. Chem. Soc.* 1986, 108, 191.
2. Kemp, D. S.; McNamara, P. E. *J. Org. Chem.* 1985, 50, 5834.
3. Belanger, P. C.; Dufresne, C.; Scheigetz, J.; Yang, R. N.; Springer, J. P.; Dmitrienko, G. I. *Can. J. Chem.* 1982, 60, 1019.
4. Krstenansky, J. L.; Baranowdki, R. L.; Currie, B. L. *Biochem. Biophys. Res. Commun.* 1982, 109, 1368.
5. Attwood, M. R.; Francis, R. J.; Hassall, C. H.; Krohn, A.; Lawton, G.; Natoff, I. L.; Nixon, J. S.; Redshaw, S.; Thomas, W. A. *FEBS Lett.* 1984, 165, 201.
6. (a)Nagai, U.; Sato, K. *Tetrahedron Lett.* 1985, 647. (b)Baldwin, J.; Lee, E. *Tetrahedron Lett.* 1986,42, 6551.

The compounds of the invention were prepared by standard solid phase peptide synthesis conditions as described in "Solid Phase Peptide Synthesis" by J. M. Stewart and J. D. Young, Second Edition (1984) and illustrated in Examples 1 and 2 in the experimental section.

The compounds of the invention may also be prepared by partial solid phase synthesis, fragment condensation methods and classical solution methods as exemplified by the methods described in "Peptide Synthesis", Second Edition, M. Bodanszky, Y. S. Klausner, and M. A. Ondetti (1976).

The standard chirality descriptors "R" and "S" are used to indicate an isomerically pure center, "RS" to indicate a mixture, and "R/S" to indicate a single pure isomer of undetermined configuration. The descriptor "±" refers to a d,l mixture of amino acids at the indicated residue. The descriptor Ψ{X} indicates the group, X, that is a replacement for the standard peptide bond, —C(O)NH—. The descriptor "*" or "**" when written in a chemical name indicates the site of a disulfide or amide linkage, respectively.

The foregoing may be better understood by reference to the following examples which are provided for illustration and not limitation of the practice of the invention. Unless otherwise indicated, the standard peptide methods described above and in examples 1 and 2 were used to assemble the different products, using the precursors indicated by the specific peptide sequence. The product was at least 95% pure, and gave NMR and mass spectra consistent with the proposed structure.

EXAMPLE 1

H-Phenylalanyl-Lysyl(N-epsilon-Cbz)-Alanyl-{(2S)-2-Amino-3-cyclohexylpropanoyl}-{(2S)-2-Amino-3-cyclohexylpropanoyl)-Leucyl-D-Alanyl-Arginyl(N-guanidino-Tos)-Merrifield Resin Boc-Arg(N-guanidino-Tos)-Merrifield resin (0.4–1.0 g) was placed in a solid phase peptide synthesis vessel and amino acids were attached to the resin sequentially in the following order: Boc-D-Alanine, Boc-Leucine, Boc-(2S)-2-Amino-3-cyclohexylpropanoic acid, Boc-(2S)-2-Amino-3-cyclohexylpropanoic acid, Boc-Alanine, (N-alpha-Boc-N-epsilon-Cbz)Lysine, Boc-Phenylalanine, according to the protocol outlined in Agenda A to yield the protected peptide resin: H-Phenylalanyl-Lysyl(N-epsilon-Cbz)-Alanyl-{(2S)-2-Amino-3-cyclohexylpropanoyl}-{(2S)-2-Amino-3-cyclohexylpropanoyl}-Leucyl-D-Alanyl-Arginyl(N-guanidino-Tos)-Merrifield resin. Following the synthesis, the protected peptide resin was removed from the reaction vessel by washing the resin three times with 20 mL DMF into a 30–60 mL sintered glass funnel, followed by washing the resin three times with 20 mL methylene chloride. The resin was dried at least five hours, then weighed.

Agenda A

1. Deblock : 45% trifluoroacetic acid (TFA) in methylene chloride containing 2.5% anisole (v/v/v).
2. Neutralization : 10% diisopropylethylamine (DIEA) in methylene chloride (v/v)
3. Single Coupling : 0.2–0.4M Boc-amino acid derivative in N,N-dimethylformamide (DMF), 0.2–0.4M diisopropylcarbodiimide (DIC) in methylene chloride, reaction time, 60 minutes.
4. Resin base washing : 10% DIEA in methylene chloride (v/v).
5. Single Coupling repeated : same as Step 3.
6. Go to next amino acid residue (go back to Step 1).
7. Upon attachment of the final amino acid to the growing peptide chain, the protecting group (t-Boc) is removed as in Step 1.

EXAMPLE 2

H-Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH The protected peptide resin of Example 1 (0.6 g) was treated with 1.0 mL anisole and 10 mL hydrogen fluoride (HF) for 60 minutes at 0° C. The HF and anisole were removed in vacuo at 0° C., and the mixture of the peptide and resin was washed with diethyl ether (2×25 mL). The crude peptide was extracted from the mixture by treatment with portions of 20% aqueous acetic acid (4×25 mL), lyophilized to a dry amorphous powder, and purified by high performance liquid chromatography (HPLC) {column: 21.4 mm ID×25 cm or 41.4 mm ID×25 cm, Dynamax (Rainin), 8 um silica, C18 reverse-phase column}. The sample was purified by gradient elution (from 20 to 60% (80% acetonitrile in water with 0.1% trifluoroacetic acid)} at a flow rate of 15–45 mL/min. FAB+ MS: $(M+H)^+ = 1011$; Amino Acid Anal.: Phe (0.91), Lys (1.01), Ala (2.06), Cha (1.96), Leu (0.91), Arg (1.04)

EXAMPLE 3

Ac-Histidyl-Lysyl-Asparaginyl-Methionyl-Glutaminyl-Leucyl-Glycyl-Arginyl-OH

FAB+ MS: $(M+H)^+ = 1025$; Amino Acid Anal.: Asx (0.98), Glx (1.07), Gly (0.97), Met (0.96), Leu (1.05), His (0.97), Lys (0.98), Arg (1.04)

EXAMPLE 4

Ac-Histidyl-Lysyl-Aspartyl-Methionyl-Phenylalanyl-Leucyl-Glycyl-Arginyl-OH

FAB+ MS: $(M+H)^+ = 1045$

EXAMPLE 5

(N-Methyl)Phenylalanyl-Lysyl-(N-Methyl)Alanyl-(Fragment-1)-Leucyl-(N-Methyl)DAlanyl-Arginyl-OH

EXAMPLE 6

Ac-Histidyl-Lysyl-Aspartyl-{(2S)-2-Aminohexanoyl}-{(2S)-2-Aminohexanoyl}-{(2S)-2-Aminohexanoyl}-Glycyl-Arginyl-OH FAB+ MS: $(M+H)^+ = 993$; Amino Acid Anal.: Asx (0.96), Gly (0.98), His (0.84), Lys (1.01), Arg(1.05), Nle (3.07)

EXAMPLE 7

H-Histidyl-Lysyl-Aspartyl-Methionyl-{(2'S,3S)-3-Amino-2-oxo-1-pyrrolidine-{2'-(4'-methyl))-pentanoyl}-Glycyl-Arginyl-OH FAB+ MS: $(M+H)^+ = 939$

EXAMPLE 8

Ac-Histidyl-Lysyl-Aspartyl-{(2S)-2-Amino-3-Cyclohexylpropanoyl]-{(2S)-2-Amino-3-cyclohexylpropanoyl}-Leucyl-3-Aminopropanoyl-Arginyl-OH FAB+ MS: $(M+H)^+ = 1087$; Amino Acid Anal.: Asx (1.01), Leu (0.99), Cha (1.98), His (0.93), Lys (1.01), Arg(1.03)

EXAMPLE 9

(N-Methyl)Phenylalanyl-Lysyl-(N-Methyl)Alanyl-{(2S)-2-Amino-3-cyclohexylpropanoyl}-Glycyl-(Fragment-2)-Arginyl-OH

EXAMPLE 10

Ac-Histidyl-Lysyl-Aspartyl-Methionyl-Threonyl-Leucyl-Glycyl-Arginyl-OH

FAB+ MS: $(M+H)^+ = 999$; Amino Acid Anal.: Asx (0.96), Thr (0.78), Gly (1.02), Met (0.84), Leu (1.05), His (0.95), Lys (0.84), Arg (1.03)

EXAMPLE 11

AC-Histidyl-Lysyl-Aspartyl-{(2S)-2-Amino-3-cyclohexylpropanoyl}-{(2S)-2-Amino-3-cyclohexylpropanoyl}-Isoleucyl-DAlanyl-Arginyl-OH

FAB+ MS: $(M+H)^+ = 1087$

EXAMPLE 12

Ac-Histidyl-Lysyl-Aspartyl-{(2S)-2-Amino-3-cyclohexylpropanoyl}-{(2S)-2-Amino-3-cyclohexyl-propanoyl}-Leucyl-DMethionyl-Arginyl-OH FAB+ MS: (M+H)+ =1147; Amino Acid Anal.: His (1.10), Lys (0.94), Asp (0.96), Cha (1.84), Leu (1.01), Met (0.96), Arg (1.03)

EXAMPLE 13

Ac-Histidyl-Lysyl-Aspartyl-{(2S)-2-Amino-3-cyclohexylpropanoyl}-{(2S)-2-Amino-3-cyclohexyl-propanoyl}-Leucyl-Pipecolyl(±)-Arginyl-OH FAB+ MS: (M+H)+ =1127; Amino Acid Anal.: His (1.19), Lys (1.04), Asp (1.09), Cha (1.71), Leu (1.04), Arg (0.92)

EXAMPLE 14

(N-Methyl)Phenylalanyl-Lysyl-(N-Methyl)Alanyl-(Fragment-3)-Leucyl-(N-Methyl)DAlanyl-Arginyl-OH

EXAMPLE 15

Ac-Histidyl-Lysyl-Aspartyl-{(2S)-2-Amino-4-cyclohexylbutanoyl}-{(2S)-2-Amino-4-cyclohexyl-butanoyl}-Leucyl-DAlanyl-Arginyl-OH

FAB+ MS: (M+H)+ =1115

EXAMPLE 16

H-6-Aminohexanoyl-Aspartyl-{(2S)-2-Amino-3-cyclohexylpropanoyl}-{(2S)-2-Amino-3-cyclohexyl-propanoyl}-Leucyl-DAlanyl-Arginyl-OH

FAB+ MS: (M+H)+ =1893

EXAMPLE 17

Ac-Histidyl-Lysyl-Alanyl-{(2S)-2-Amino-3-cyclohexylpropanoyl}-{(2S)-2-Amino-3-cyclohexyl-propanoyl}-Leucyl-DAlanyl-Arginyl-OH

FAB+ MS: (M+H)+ =1043

EXAMPLE 18

(N-Methyl)Phenylalanyl-Lysyl-(N-Methyl)Alanyl-{(2S)-2-Amino-3-cyclohexylpropanoyl}-(Fragment-4)-(N-Methyl)DAlanyl-Arginyl-OH

EXAMPLE 19

Ac-Histidyl-Lysyl-Aspartyl-Cysteinyl(Acm)-Cysteinyl(Acm)-Leucyl-DAlanyl-Arginyl-OH

FAB+ MS: (M+H)+ =1129

EXAMPLE 20

Ac-Histidyl-Lysyl-Aspartyl-DTryptophyl-{(2S)-2-Amino-3-cyclohexylpropanoyl}-Leucyl-DAlanyl-Arginyl-OH

FAB+ MS: (M+H)+ =1120

EXAMPLE 21

Ac-Histidyl-Lysyl-Aspartyl-Methionyl-Histidyl-Leucyl-DAlanyl-Arginyl-OH

FAB+ MS: (M+H)+ =1049

EXAMPLE 22

Ac-Histidyl-Lysyl-Aspartyl-{(2S)-2-Amino-3-cyclohexylpropanoyl}-DTryptophyl-Leucyl-DAlanyl-Arginyl-OH

FAB+ MS: (M+H)+ =1120

EXAMPLE 23

Ac-Histidyl-Lysyl-Aspartyl-{(2S)-2-Amino-3-cyclohexylpropanoyl}-Histidyl-Leucyl-DAlanyl-Arginyl-OH

FAB+ MS: (M+H)+ =1071

EXAMPLE 24

(N-Methyl)Phenylalanyl-Lysyl-(N-Methyl)Alanyl-{(2S)-2-Amino-3-cyclohexylpropanoyl}-(Fragment-5)-(N-Methyl)DAlanyl-Arginyl-OH

EXAMPLE 25

Ac-Histidyl-Lysyl-Aspartyl-Cysteinyl*-Cysteinyl*-Leucyl-Alanyl-Arginyl-OH

FAB+ MS: (M+H)+ =985

EXAMPLE 26

Ac-Histidyl-Lysyl-Aspartyl-{(2S)-2-Amino-3-cyclohexylpropanoyl}-{(2S)-2-Amino-3-cyclohexyl-propanoyl}-Valyl-DAlanyl-Arginyl-OH FAB+ MS: (M+H)+ =1073; Amino Acid Anal.: His (1.17), Lys (1.00), Asp (0.93), Cha (1.71), Val (1.00), Ala (0.90), Arg (0.97)

EXAMPLE 27

Ac-Histidyl-Lysyl-Aspartyl-{(2S)-2-Amino-3-cyclohexylpropanoyl}-{(2S)-2-Amino-3-cyclohexyl-propanoyl}-Leucyl-DSeryl-Arginyl-OH FAB+ MS: (M+H)+ =1103; Amino Acid Anal.: His (1.06), Lys (1.19), Asp (0.83), Cha (1.93), Leu (1.04), Ser (0.50), Arg (0.91)

EXAMPLE 28

(N-Methyl)Phenylalanyl-Lysyl-(N-Methyl)Alanyl-{(2S)-2-Amino-3-cyclohexylpropanoyl}-(Fragment-6)-(N-Methyl)DAlanyl-Arginyl-OH

EXAMPLE 29

Ac-Histidyl-Lysyl-Aspartyl-{(2S)-2-Amino-3-cyclohexylpropanoyl}-{(2S)-2-Amino-3-cyclohexyl-propanoyl}-Leucyl-DArginyl-Arginyl-OH FAB+ MS: (M+H)+ =1172; Amino Acid Anal. His (1.09), Lys (0.97), Asp (0.93), Cha (1.74), Leu (0.95), Arg (1.96)

EXAMPLE 30

Ac-Histidyl-Lysyl-Aspartyl-{(2S)-2-Amino-3-cyclohexylpropanoyl}-{(2'S,3S)-3-Amino-2-oxo-1-pyrrolidine-{2'-(4'-methyl)}-pentanoyl}-DAlanyl-Arginyl-OH

FAB+ MS: (M+H)+ =1017

EXAMPLE 31

Ac-(4-NO$_2$)Phenylalanyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1142

EXAMPLE 32

H-Phenylalanyl-{(2S)-2Amino-6-trifluoroacetamidohexanoyl}-Alanyl-{(2S)-2-Amino-3-cyclohexylpropanoyl}-{(2S)-2-Amino-3-cyclohexyl-propanoyl}-Leucyl-DAlanyl-Arginyl-OH

EXAMPLE 33

Ac-Histidyl-Lysyl-Glutaminyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1100

EXAMPLE 34

Ac-Histidyl-Lysyl-Cysteinyl(Acm)-{(2S)-2-Amino-3-cyclohexylpropanoyl}-{(2S)-2-Amino-3-cyclohexylpropanoyl}-Leucyl-DCysteinyl(Acm)-Arginyl-OH
FAB+ MS: (M+H)+ =1249

EXAMPLE 35

H-Phenylalanyl-{(2S)-2-Amino-6-formamidohexanoyl}-Alanyl-{(2S)-2-Amino-3-cyclohexylpropanoyl}-{(2S)-2-Amino-3-cyclohexylpropanoyl}-Leucyl-DAlanyl-Arginyl-OH

EXAMPLE 36

Ac-Histidyl-Lysyl-Aspartyl-Alanyl-{(2S)-2-Amino-3-cyclohexylpropanoyl}-Leucyl-DAlanyl-Arginyl-OH
FAB+ MS: (M+H)+ =1005

EXAMPLE 37

Ac-Histidyl-(N-delta-iPr)Ornithyl-Asparaginyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1114; Amino Acid Anal.: Ala (1.00), Leu (1.01), His (1.11), Cha (1.79), Arg (1.01)

EXAMPLE 38

Ac-Histidyl-Lysyl-Asparaginyl-{(2S)-2-Amino-3-cyclohexylpropanoyl}-{(2S)-2-Amino-3-cyclohexylpropanoyl}-Leucyl-DAlanyl-Arginyl-NHNH$_2$ N-Acetyl-Histidyl-Lysyl(N-epsilon-Cbz)-Asparaginyl{(2S)-2-Amino-3-cyclohexylpropanoyl}-{(2S)-2-Amino-3-cyclohexylpropanoyl}-Leucyl-D-Alanyl-Arginyl(N-guanidino-Tos)-OResin (0.62g) was suspended in 10 mL of N,N-dimethylformamide (DMF), and 1 mL of anhydrous hydrazine was added. The mixture was stirred at room temperature for 4 days and filtered. The resin was washed with an additional 10 mL of DMF, and the combined DMF solution was poured into 100 mL of diethylether. Upon cooling the mixture, it gradually solidified. The solid was collected by filtration, washed with 50 mL of water and dried. The dry solid obtained (approximately 160 mg) was treated with HF and anisole, as described in Example 2. After lyophilization, 153 mg of crude peptide was obtained which was purified by HPLC (Example 2) to yield 35.6 mg of pure peptide that gave NMR and mass spectra consistent with the desired product.
FAB+ MS: (M+H)+ =1099

EXAMPLE 39

Ac-Histidyl-Lysyl-Aspartyl-{(2S)-2-Amino-3-cyclohexylpropanoyl}-{(2S)-2-Amino-3-cyclohexylpropanoyl}-{(2S)-2-Aminopentanoyl}-DAlanyl-Arginyl-OH
FAB+ MS: (M+H)+ =1189; Amino Acid Anal.: Ala (1.00), His (1.11), Cha (1.89), Lys (0.98), Arg (1.01)

EXAMPLE 40

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-Glycyl-Glycyl-OH

EXAMPLE 41

Ac-Histidyl-Lysyl-Asparaginyl-{(2S)-2-Amino-3-cyclohexylpropanoyl}-{(2S)-2-Amino-3-cyclohexylpropanoyl}-Leucyl-DAlanyl-Arginyl-OCH$_3$
FAB+ MS: (M+H)+ =1100; Amino Acid Anal.: Asx (0.91), Ala (0.90), Leu (0.96), His (1.08), Cha (1.65), Lys (0.97), Arg (0.95)

EXAMPLE 42

Ac-Histidyl-Lysyl-Aspartyl-{(2R)-2-Amino-3-cyclohexylpropanoyl}-{(2R)-2-Amino-3-cyclohexylpropanoyl}-Leucyl-DAlanyl-Arginyl-OH
FAB+ MS: (M+H)+ =1087; Amino Acid Anal.: Asx (0.99), Ala (0.95), Leu (1.02), His (1.07), Cha (1.80), Lys (1.03), Arg (1.02)

EXAMPLE 43

Ac-Alanyl-Arginyl-Asparaginyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1048; Amino Acid Anal.: Asx (1.01), Ala (1.94), Leu (1.02), Cha (1.88), Arg (2.08)

EXAMPLE 44

Ac-Lysyl-Lysyl-Asparaginyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1077; Amino Acid Anal.: Asx (0.98), Ala (0.93), Leu (1.01), Cha (1.87), Lys (2.01), Arg (1.01)

EXAMPLE 45

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-{(4R)-(4-Ethyl)Agmatine}

N-alpha-Boc-N-guanidino-Tosyl-Arginine is converted to its aldehyde which is reacted with methylenetriphenylphosphorane using a modified literature procedure (Luly, J. R.; Dellaria, J. F.; Plattner, J. J.; Soderquist, J. L.; Yi, N. *J. Org. Chem.* 1987, 52, 1487) followed by hydrogenation on Pd/C to yield (4R)-N-alpha-Boc-N-guanidino-Tosyl-(4-Ethyl)Agmatine. The protected peptide: N-Boc-(N-Methyl)Phenylalanyl-N-epsilon-Cbz-Lysyl-(N-Methyl)Alanyl-{(2S)-2-Amino-3-cyclohexylpropanoyl}-Gylcyl-Leucyl-(N-Methyl)-DAlanine is synthesized according to the procedure of Example No. 309. The above agmatine derivative is treated with 4N-HCl/Dioxane, and the resulting salt is coupled with the protected peptide using a DCC/HOBT mediated coupling procedure. The protecting groups are removed by treatment with liquid HF/anisole according to the procedure of Example 2.

EXAMPLE 46

H-Lysyl-Phenylalanyl-Aspartyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1055

EXAMPLE 47

H-Phenylalanyl-Lysyl-4-Aminobutanoyl-{(2S)-2-Amino-3-cyclohexylpropanoyl}-Leucyl-DAlanyl-Arginyl-OH FAB+ MS: (M+H)+ =872; Amino Acid Anal.: Phe (0.99), Lys (1.01), Gaba (0.97), Cha (0.94), Leu (1.06), Ala (1.00), Arg (1.00)

EXAMPLE 48

H-DPhenylalanyl-DLysyl-DAspartyl-DMethionyl-DGlutaminyl-DLeucyl-Arginyl-DArginyl-OH FAB+ MS: (M+H)+ =1093; Amino Acid Anal.: Asp (0.97), Glx (1.05), Met (0.61), Leu (1.03), Phe (0.97), Lys (0.94), Arg (2.04)

EXAMPLE 49

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-{NH(alpha)Phenethyl(R/S)}

The protected peptide: N-Boc-(N-Methyl)Phenylalanyl-N-epsilon-Boc-Lysyl-(N-Methyl)Alanyl-{(2S)-2-Amino-3-cyclohexylpropanoyl}-Gylcyl-Leucyl-(N-Methyl)DAlanine is prepared by the method described below. The peptide chain is elongated by the same method described in Example 1, except that after N-alpha-Fmoc-N-epsilon-Boc-Lysine is coupled, the sequence is stopped at agenda A-step 5. The obtained N-alpha-Fmoc-N-epsilon-Boc-Lysyl-peptide resin is treated with DMF:piperidine (1:1) for 30 minutes at room temperature. After the peptide resin is washed with DMF and methylene chloride, the next synthetic protocol (Example 1, agenda A-step 3) is initiated with the exception that the N-terminal protecting group is not removed at the end of the synthesis. The fully protected peptide is obtained by the procedure of Example 309. The protected peptide is coupled with alphaphenethylamine using DCC/HOBT. The protecting groups are removed by treatment with 4N-HCl/dioxane to give the desired compound.

EXAMPLE 50

H-Phenylalanyl-Lysyl-Prolyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =1037; Amino Acid Anal.: Phe (1.01), Lys (1.01), Pro (1.02), Cha (1.96), Leu (1.09), Ala (0.88), Arg (1.04)

EXAMPLE 51

H-Phenylalanyl-Histidyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS (M+H)+ =1148; Amino Acid Anal.: Phe (0.95), His (1.07), Lys (0.98), Ala (1.64), Cha (1.76), Leu (1.02), Arg (0.98)

EXAMPLE 52

Hydrocinnamoyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =1040; Amino Acid Anal.: Lys (0.64), Asp (0.73), Cha (1.93), Leu (1.04), Ala (0.82), Arg (1.04)

EXAMPLE 53

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-{(4R)-(4-(beta-Phenethyl))Agmatine}

(4R)-N-alpha-Boc-N-guanidino-Tosyl-(4-(beta-Phenethyl))Agmatine is synthesized by the method described in Example 45 with the exception that benzyltriphenylphosphorane is used instead of methylenetriphenylphosphorane. The Boc group is removed by treatment with 4N-HCl/dioxane, and the resulting amine salt is coupled with the protected heptapeptide (cited in Example 45) using DCC/HOBT. The protecting groups are removed by treatment with liquid HF/anisole to give the desired compound.

EXAMPLE 54

H-Phenylalanyl-Lysyl-DProlyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =1037; Amino Acid Anal.: (Phe (1.00), Lys (1.01), Pro (1.06), Cha (1.94), Leu (1.09), Ala (0.86), Arg (1.04)

EXAMPLE 55

H-Phenylalanyl-Lysyl-Aspartyl-{(2S)-2-Amino-3-cyclohexylpropanoyl}-{(2'S,3S)-3-Amino-2-oxo-1-pyrrolidine-{2'-(4'-methyl)}-pentanoyl}-DAlanyl-Arginyl-OH FAB+ MS: (M+H)+ =985; Amino Acid Anal.: Phe (0.98), Lys (0.94), Asp (1.01), Cha (0.95), Ala (1.06), Arg (1.07)

EXAMPLE 56

H-Phenylalanyl-Lysyl-Alanyl-{(2S)-2-Amino-3-cyclohexylpropanoyl}-{(2S)-2-Amino-3-cyclohexylpropanoyl}-Leucyl-DProlyl-Arginyl-OH FAB+ MS: (M+H)+ =1037; Amino Acid Anal.: Phe (0.99), Lys (0.99), Ala (0.93), Cha (1.94), Leu (1.09), Pro (0.83), Arg (1.07)

EXAMPLE 57

H-Phenylalanyl-Histidyl-Lysyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1077

EXAMPLE 58

Ac-(4-NH2)Phenylalanyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =1112; Amino Acid Anal.: (4-NH2)Phe (0.75), Lys (1.02), Asp (0.98), Cha (1.90), Leu (1.09), Ala (0.99, Arg (1.03)

EXAMPLE 59

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-SCH2CH3

N-alpha-Boc-Arginine is reacted with ethylmercaptan, according to the procedure described by Yamada, S.; Yokoyama, Y.; Shioiri, T. *J. Org. Chem.* 1974, 39, 3302. The ester obtained is treated with 4N-HCl/dioxane and coupled with the protected heptapeptide (cited in Example 49). Final deprotection is carried out by treatment with 4N-HCl/dioxane to give the desired product.

EXAMPLE 60

Ac-Phenylalanyl-Lysyl-Asparaginyl-Histidyl-{(2S)-2-Amino-3-cyclohexylpropanoyl}-Leucyl-DAlanyl-Tryptophyl-OH

FAB+ MS: (M+H)+ = 1110

EXAMPLE 61

H-Phenylalanyl-Lysyl-6-Aminohexanoyl-{(2S)-2-Amino-3-cyclohexylpropanoyl}-Leucyl-DAlanyl-Arginyl-OH FAB+ MS: (M+H)+ = 900; Amino Acid Anal.: Phe (0.98), Lys (0.99), Cha (0.94), Leu (1.07), Ala (1.01), Arg (1.02)

EXAMPLE 62

H-(4-I)Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ = 1137

EXAMPLE 63

H-Tyrosyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1027; Amino Acid Anal.: Tyr (0.32), Lys (1.00), Ala (1.89), Cha (1.45), Leu (1.19), Arg (1.12)

EXAMPLE 64

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-NHCH$_2$CH$_3$ N-alpha-Boc-Arginine is coupled with ethylamine using mixed anhydride method conditions. Deprotection of the product with 4N-HCl/dioxane yields arginine ethylamide dihydrochloride which is coupled with the protected heptapeptide (cited in Example 49) using DCC/HOBT. The protecting groups are removed by treatment with 4N-HCl/dioxane to give the desired product.

EXAMPLE 65

H-Phenylalanyl-Arginyl-Aspartyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1083; Amino Acid Anal.: Phe (0.94), Arg (1.98), Asp (1.07), Cha (2.01), Leu (1.14), Ala (0.82)

EXAMPLE 66

H-Phenylalanyl-Lysyl-Aspartyl-{(2S)-2-Amino-3-cyclohexylpropanoyl}-Alanyl-Leucyl-DAlanyl-Arginyl-OH

FAB+ MS: (M+H)+ = 973

EXAMPLE 67

H-(4-CH$_3$)Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1025; Amino Acid Anal.: (4-Me)Phe (0.76), Lys (0.99), Ala (1.71), Cha (1.92), Leu (1.07), Arg (1.02)

EXAMPLE 68

H-(4-F)Phenylalanyl(R/S)-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ = 1029

EXAMPLE 69

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-NHCH$_2$C$_6$H$_5$ This compound is prepared by the same method described in Example 64 with the exception that benzylamine is used instead of ethylamine.

EXAMPLE 70

H-(4-F)Phenylalanyl(R/S)-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1029; Amino Acid Anal.: (4-F)Phe (0.96), Lys (1.03), Ala (1.94), Cha (1.96), Leu (1.07), Arg (1.00)

EXAMPLE 71

H-(3-F)Phenylalanyl(R/S)-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1029; Amino Acid Anal.: (3-F)Phe (0.84), Lys (1.00), Ala (1.84), Cha (1.98), Leu (1.03), Arg (0.99)

EXAMPLE 72

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-NH(2-Pyridyl)methyl This compound is synthesized by the same method described in Example 64 with the exception that (2-pyridyl)methylamine is used instead of ethylamine.

EXAMPLE 73

H-(3-F)Phenylalanyl(R/S)-Lysyl-Alanyl-{(2S)-2-Amino-3-cyclohexylpropanoyl{-}(2S)-2-Amino-3-cyclohexylpropanoyl}-Leucyl-DAlanyl-Arginyl-OH FAB+ MS: (M+H)+ = 1029; Amino Acid Anal.: (3-F)Phe (0.85), Lys (0.99), Ala (0.84), Cha (1.98), Leu (1.03), Arg (1.00)

EXAMPLE 74

H-(2-F)Phenylalanyl(R/S)-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1029; Amino Acid Anal.: (2-F)Phe (1.01), Lys (1.00), Ala (1.95), Cha (2.02), Leu (1.08), Arg (1.04)

EXAMPLE 75

H-(2-F)Phenylalanyl(R/S)-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1029; Amino Acid Anal.: (2-F)Phe (0.99), Lys (0.99), Ala (1.84), Cha (1.98), Leu (1.03), Arg (1.00)

EXAMPLE 76

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-NHNHC$_6$H$_5$ The compound is prepared in analogy to Example 38.

EXAMPLE 77

H-Phenylalanyl-Lysyl-Alanyl-Leucyl-Leucyl-Leucyl-DAlanyl-Histidyl-OH
FAB+ MS: (M+H)+ = 912

EXAMPLE 78

H-(4-NO$_2$)Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ = 1056 Amino Acid Anal.: (4-NO$_2$)Phe (0.69), Lys (0.99), Ala (1.83), Cha (1.94), Leu (1.07), Arg (1.00)

EXAMPLE 79

H-Phenylalanyl-Lysyl-Phenylalanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ = 1087

EXAMPLE 80

Phenoxyacetyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ = 998

EXAMPLE 81

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-N(—CH$_2$C$_6$H$_5$)NH$_2$
The compound is prepared in analogy to Example 38.

EXAMPLE 82

H-Tryptophyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ = 1050

EXAMPLE 83

H-Phenylalanyl-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH
FAB+ MS (M+H)+ = 1077

EXAMPLE 84

H-{3-(2'-Naphthyl)alanyl}-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ = 1061

EXAMPLE 85

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-OCH$_2$C$_6$H$_5$ N-alpha-Boc-Arginine is converted to its benzyl ester, according to the procedure described by Wang, S.-S.; Gisin, B. F.; Winter, D. P.; Makofske, R.; Kulesha, I. D.; Tzougraki, C. and Meienhofer, J. *J. Org. Chem.* 1977, 42, 1286. The compound obtained is treated with 4N-HCl/dioxane and coupled with the protected heptapeptide (cited in Example 45) using DCC/HOBT. The protecting groups are removed by treatment with 4N-HCl/dioxane to give the desired product.

EXAMPLE 86

H-{3-(1'-Naphthyl)alanyl}-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ = 1061

EXAMPLE 87

H-(3-F)Phenylalanyl(R/S)-Lysyl-DAlanyl-{(2S)-2-Amino-3-cyclohexylpropanoyl}-DAlanyl-Leucyl-DAlanyl-Arginyl-OH
FAB+ MS: (M+H)+ = 947

EXAMPLE 88

H-Phenylalanyl-Lysyl-{(2S)-2-Amino-3-cyclohexylpropanoyl}-3-(Aminomethyl)benzoyl-Leucyl-DAlanyl-Arginyl-OH
FAB+ MS: (M+H)+ = 920

EXAMPLE 89

H-Phenylalanyl-Lysyl-Alanyl-{(2S)-2-Amino-3-cyclohexylpropanoyl}-{(2S)-2-Amino-3-cyclohexylpropanoyl}-Leucyl-Dpipecolyl-Arginyl-OH
FAB+ MS: (M+H)+ = 1051

EXAMPLE 90

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-NHOCH$_3$
The compound is prepared in analogy to Example 38.

EXAMPLE 91

H-Phenylalanyl-Lysyl-Asparaginyl-Phenylalanyl-Phenylalanyl-Leucyl-DAlanyl-Arginyl-OH
FAB+ MS: (M+H)+ = 1042

EXAMPLE 92

H-Phenylalanyl-Lysyl-Alanyl-Phenylalanyl-Phenylalanyl-Leucyl-DAlanyl-Arginyl-OH
FAB+ MS: (M+H)+ = 999

EXAMPLE 93

H-Phenylalanyl-Lysyl-Phenylalanyl-{(2S)-2-Amino-3-cyclohexylpropanoyl}-{(2S)-2-Amino-3-cyclohexylpropanoyl}-Leucyl-DAlanyl-Histidyl-OH
FAB+ MS (M+H)+ = 1068

EXAMPLE 94

H-Phenylalanyl-Lysyl-Alanyl-{(2S)-2-Amino-3-cyclohexylpropanoyl}-{(2S)-2-Amino-4-pentenoyl}-Leucyl-Glycyl-Arginyl-OH

EXAMPLE 95

Ac-Histidyl-Lysyl-Asparaginyl-(2-CH$_3$)Phenylalanyl(R/S)-(2-CH$_3$)Phenylalanyl(R/S)-Leucyl-DAlanyl-Arginyl-OH
FAB+ MS: (M+H)+ = 1102; Amino Acid Anal.: Asx (1.01), Leu (0.97), His (0.89), Ala (1.00), Lys (1.01), Arg (1.04)

EXAMPLE 96

Ac-Histidyl-Lysyl-Asparaginyl-(4-CH$_3$)Phenylalanyl(R/S)-(4-CH$_3$)Phenylalanyl(R/S)-Leucyl-DAlanyl-Arginyl-OH
FAB+ MS: (M+H)+ = 1102

EXAMPLE 97

H-Phenylalanyl-Lysyl-Alanyl-{(2S)-2-Amino-3-cyclohexylpropanoyl}-{2-Amino-2-methyl-propanoyl}-Leucyl-DAlanyl-Arginyl-OH

EXAMPLE 98

Ac-Arginyl-Lysyl-Asparaginyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1105; Amino Acid Anal.: Asx (0.97), Ala (0.98), Leu (1.02), Cha (1.88), Lys (1.01), Arg (2.02)

EXAMPLE 99

Ac-Aspartyl-Lysyl-Asparaginyl-{(2S)-2-Amino-3-cyclohexylpropanoyl}-{(2S)-2-Amino-3-cyclohexylpropanoyl}-{(2S)-2-Amino-3-cyclohexylpropanoyl}-Leucyl-DAlanyl-Arginyl-OH The trifluoroacetic acid salt of Aspartyl(beta-Benzyl)-Lysyl(N-epsilon-Cbz)-{(2S)-2-Amino-3-cyclohexylpropanoyl}-{(2S)-2-Amino-cyclohexylpropanoyl}-Leucyl-D-Alanyl-Arginine(N-guanidino-Tos)-OResin (0.56 g) was prepared according to the procedure described in Example 1. The peptide-resin obtained was washed with 10%-diisopropylethylamine (DIEA) in methylene chloride (3×15 mL, 45 seconds each) and methylene chloride (4×15 mL). 10%-DIEA in methylene chloride (15 mL) was introduced into the reaction vessel and acetic anhydride (0.47 mL, 5 mmole) was added. It was reacted at room temperature for 1 hour and repeated if neccesary (until Kaiser test was negative). The N-acetyl-peptide-resin was treated with HF and anisole to yield 127.3 mg of dried powder A portion of the powder (75 mg) was purified by HPLC, according to the procedure mentioned in Example 2 to yield 40.4 mg of pure product consistent with proposed structure.

FAB+ MS: (M+H)+ = 1064 Amino Acid Anal.: Asx (1.85), Ala (1.04), Leu (1.08), Cha (1.89), Lys (0.96), Arg (1.07)

EXAMPLE 100

H-{(2R)-2-Amino-3-cyclohexylpropanoyl}-DLysyl-DAspartyl-{(2R)-2-Amino-3-cyclohexylpropanoyl}-{(2R)-2-Amino-3-cyclohexylpropanoyl}-DLeucyl-Alanyl-DArginyl-OH

FAB+ MS: (M+H)+ = 1061

EXAMPLE 101

H-Phenylalanyl-Lysyl-Alanyl-{(2S)-2-Amino-3-cyclohexylpropanoyl}-{Aminocyclopropyl-1-carbonyl}-Leucyl-DAlanyl-Arginyl-OH

EXAMPLE 102

H-Phenylalanyl-Lysyl-Lysyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ = 1068

EXAMPLE 103

H-{3-(2'-Thienyl)alanyl(±)}-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ = 1084

EXAMPLE 104

H-Phenylalanyl-Lysyl-Alanyl-(4-I)Phenylalanyl-Alanyl-Leucyl-DAlanyl-Arginyl-OH

FAB+ MS: (M+H)+ = 1049

EXAMPLE 105

H-Phenylalanyl-Lysyl-Alanyl-{(2S)-2-Amino-3-cyclohexylpropanoyl}-{Aminocyclohexyl-1-carbonyl}-Leucyl-DAlanyl-Arginyl-OH

EXAMPLE 106

H-Phenylalanyl-Lysyl-Alanyl-{(2S)-2-Amino-4-cyclohexylbutanoyl}-Alanyl-Leucyl-DAlanyl-Arginyl-OH

FAB+ MS: (M+H)+ = 943

EXAMPLE 107

H-Phenylalanyl-Lysyl-Alanyl-(3-F)Phenylalanyl(R/S)-Alanyl-LeuCyl-DAlanyl-Arginyl-OH

FAB− MS: (M−H)− = 939

EXAMPLE 108

H-Phenylalanyl-Lysyl-Alanyl-(3-F)Phenylalanyl(R/S)-Alanyl-Leucyl-DAlanyl-Arginyl-OH

FAB+ MS: (M+H)+ = 941

EXAMPLE 109

H-Phenylalanyl-Lysyl-Alanyl-{(2S)-2-Amino-4-phenylbutanoyl}-Alanyl-Leucyl-DAlanyl-Arginyl-OH

FAB+ MS: (M+H)+ = 937

EXAMPLE 110

Ac-{(1R/S)(2R/S)((Z)-1-Amino-2-phenylcyclopropyl)-1-carbonyl}-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH The C-terminal heptapeptide is prepared under standard solid phase peptide synthesis conditions. The epsilon nitrogen of lysine is protected as its Fmoc derivative which remains intact through the acidic cleavage of the heptapeptide from the resin. Racemic ((Z)-1-Acetamido-2-phenylcyclopropane)-1-carboxylic acid is prepared from Z-acetamidocinnamic acid according to the methodology given in, Schmidt, U.; Lieberknecht, A.; Wild, J. *Synthesis* 1988, 159–172, and the references cited therein. This amino acid is then coupled in solution phase to the heptapeptide by the mixed acid anhydride method, and the Fmoc group is removed with piperidine. Separation of the diastereomeric products by HPLC furnishes the final product.

EXAMPLE 111

H-Isoleucyl-Seryl-Phenylalanyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ = 1255

EXAMPLE 112

H-Phenylalanyl-Lysyl-Alanyl-{(2R/S)-2-Aminooctanoyl}-Alanyl-Leucyl-DAlanyl-Arginyl-OH

FAB+ MS: (M+H)+ = 917

EXAMPLE 113

H-Phenylalanyl-Lysyl-Alanyl-{(2R/S)-2-Aminooctanoyl}-Alanyl-Leucyl-DAlanyl-Arginyl-OH
FAB+ MS: (M+H)+ =917

EXAMPLE 114

H-Phenylalanyl-Lysyl-Alanyl-{3-(2'-Thienyl-)alanyl(R/S)}-Alanyl-Leucyl-DAlanyl-Arginyl-OH
FAB+ MS: (M+H)+ =929

EXAMPLE 115

Ac-{(Z)-2-Amino-3-phenyl-2-propenoyl}-Lysyl-Alanyl-{(2S)-2-Amino-3-cyclohexylpropanoyl}-Alanyl-Leucyl-Glycyl-Arginyl-OH The C-terminal heptapeptide is prepared using standard solid phase peptide synthesis techniques. The lysine is incorporated with the epsilon nitrogen protected with Fmoc which survives HF cleavage of the peptide from the resin and removal of the other protecting groups. Z-Acetamidocinnamic acid is coupled to the heptapeptide in solution phase employing the mixed acid anhydride method. The Fmoc group is subsequently removed with piperidine, and the crude peptide is purified by HPLC.

EXAMPLE 116

H-Alanyl-Asparaginyl-Isoleucyl-Seryl-Phenylalanyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1440

EXAMPLE 117

H-Phenylalanyl-Lysyl-Alanyl-Phenylseryl-Alanyl-Leucyl-DAlanyl-Arginyl-OH
FAB+ MS: (M+H)+ =939

EXAMPLE 118

H-Phenylalanyl-Lysyl-Leucyl-{(2S)-2-Amino-3-cyclohexylpropanoyl}-{(2S)-2-Amino-3-cyclohexylpropanoyl}-Leu-DAlanyl-Arginyl-OH
FAB+ MS: (M+H)+ =1053

EXAMPLE 119

(N,N-Dimethyl)Alanyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 120

H-Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-(omega-N, omega'-N-diethyl)Arginyl-OH FAB+ MS: (M+H)+ = 1081; Amino Acid Anal.: Ala (1.91), Leu (1.09), Phe (0.96), Cha (1.98), Lys (0.96)

EXAMPLE 121

H-Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-(omega-N-phenyl)Arginyl-OH FAB+MS: (M+H)+ = 1087; Amino Acid Anal.: Ala (1.86), Leu (0.98), Phe (1.07), Cha (1.98), Lys (1.11)

EXAMPLE 122

H-Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-(omega-N-methyl)Arginyl-OH FAB+ MS: (M+H)+ = 1025; Amino Acid Anal.: Ala (1.90), Leu (1.25), Phe (0.95), Cha (2.25), Lys (1.08), Arg (1.08)

EXAMPLE 123

(N-Methyl)Phenylalanyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 124

Ac-Histidyl-Lysyl-Asparaginyl-{(2S)-2-Amino-3-cyclohexylpropanoyl}-{(2S)-2-Amino-3-cyclohexylpropanoyl}-Leucyl-DAlanyl-Arginyl-NHOH The compound was prepared in analogy to Example 38.
FAB+ MS: (M+H)+ = 1101

EXAMPLE 125

Ac-Phenylalanyl-Lysyl-Glutamyl-{(2S)-2-Amino-3-cyclohexylpropanoyl}-{(2S)-2-Amino-3-cyclohexylpropanoyl}-Leucyl-DAlanyl-Arginyl-OH The synthesis, deprotection and cleavage of the resin-bound peptide was carried out as outlined in Examples 1 and 2 except for the acetylation of the N-terminus which occurred between the synthesis and deprotection/cleavage steps. The acetylation was carried out as described in "Solid Phase Peptide Synthesis" by John M. Stewart and Janis D. Young, Second Edition (1984), p. 73.
FAB+ MS: (M+H)+ = 1111

EXAMPLE 126

H-phenylalanyl-Lysyl-Glutamyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ = 1069

EXAMPLE 127

(N-Benzyl)Glycyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 128

H-Phenylalanyl-Ornithyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =997

EXAMPLE 129

H-Phenylalanyl-Lysyl-Alanyl-{(2S)-2-Amino-3-cyclohexylpropanoyl}-{(2S)-2-Amino-3-cyclohexylpropanoyl}-Lysyl-DAlanyl-Arginyl-OH
FAB+ MS: (M+H)+ = 1026

EXAMPLE 130

H-Phenylalanyl-Lysyl-Alanyl-{(2S)-2-Amino-3-cyclohexylpropanoyl}-{(2S)-2-Amino-3-cyclohexylpropanoyl}-Glutamyl-DAlanyl-Arginyl-OH
FAB+ MS: (M+H)+ = 1027

EXAMPLE 131

H-Phenylalanyl-Lysyl-Alanyl-{(2S)-2-Amino-3-cyclohexylpropanoyl}-{(2S)-2-Amino-3-cyclohexylpropanoyl}-Threonyl-DAlanyl-Arginyl-OH
FAB+ MS: (M+H)+ =999

EXAMPLE 132

(N-Phenyl)Glycyl-Lysyl-Alanyl-{(2S)-2-Amino-3-cyclohexylpropanoyl}-Alanyl-Leucyl-(N-Methyl)-DAlanyl-Arginyl-OH

EXAMPLE 133

H-Leucyl-Arginyl-Alanyl-Asparaginyl-Isoleucyl-Seryl-Phenylalanyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1709

EXAMPLE 134

H-Phenylalanyl-Glutaminyl-Aspartyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1055

EXAMPLE 135

H-Phenylalanyl-Alanyl-Aspartyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =998

EXAMPLE 136

Alpha-Hydrazinohistidyl-Lysyl-Alanyl-{(2S)-2-Amino-3-cyclohexylpropanoyl}-Alanyl-Leucyl-(N-Methyl)DAlanyl-Arginyl-OH

EXAMPLE 137

2-Pyridylacetyl-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1049

EXAMPLE 138

H-{(2S)-2-Amino-4-phenylbutanoyl}-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1091

EXAMPLE 139

(5-Dimethylamino-1-naphthalenesulfonyl)-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1163

EXAMPLE 140

Methoxyacetyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 141

(1,2,3,4-Tetrahydroisoquinolin-3-carbonyl(±)}-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1089

EXAMPLE 142

H-Phenylalanyl-Lysyl-Alanyl-{(2S)-2-Amino-3-cyclohexylpropanoyl}-{(2S)-2-Amino-3-CyClohexylpropanoyl}-Leucyl-DPhenylalanyl-Arginyl-OH

FAB+ MS: (M+H)+ =1087

EXAMPLE 143

H-phenylalanyl-Lysyl-Alanyl-{(2S)-2-Amino-3-cyclohexylpropanoyl}-{(2S)-2-Amino-3-cyclohexylpropanoyl}-Glycyl-DAlanyl-Arginyl-OH FAB+ MS (M+H)+ =955; Amino Acid Anal.: Phe (1.01), Lys (1.07), Ala (1.90), Cha (2.10), Arg (1.06), Gly (0.97)

EXAMPLE 144

H-Phenylalanyl-Lysyl-Alanyl-{(2S)-2-Amino-3-cyclohexylpropanoyl}-{(2S)-2-Amino-3-cyclohexylpropanoyl}-Alanyl-DAlanyl-Arginyl-OH FAB+ MS: (M+H)+ =969; Amino Acid Anal.: Phe (1.03), Lys (1.01), Ala (2.86), Cha (2.11), Arg (1.10)

EXAMPLE 145

H-Phenylalanyl-{(2S)-2-Amino-5-ureidopentanoyl}-Alanyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1040

EXAMPLE 146

Hydroxyacetyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 147

H-Phenylalanyl-Lysyl-Alanyl-{(2S)-2-Amino-2-cyclohexylpropanoyl}-Lysyl-Leucyl-DAlanyl-Arginyl-OH

FAB+ MS: (M+H)+ =986

EXAMPLE 148

H-Phenylalanyl-Lysyl-Alanyl-{(2S)-2-Amino-3-cyclohexylpropanoyl}-Glutamyl-Leucyl-DAlanyl-Arginyl-OH

FAB+ MS: (M+H)+ =987

EXAMPLE 149

H-Phenylalanyl-Lysyl-Histidyl-{(2S)-2-Amino-3-cyclohexylpropanoyl}-{(2'R/S,3S)-3-Amino-2-oxo-1-azepine-2'-pentanoyl}-DAlanyl-Arginyl-OH

FAB+ MS: (M+H)+ =1021

EXAMPLE 150

H-Phenylalanyl-Lysyl-Histidyl-{(2S)-2-Amino-3-cyclohexylpropanoyl}-{(2'R/S,3S)-3-Amino-2-oxo-1-azepine-2'-pentanoyl}-DAlanyl-Arginyl-OH

FAB+ MS: (M+H)+ =1021

EXAMPLE 151 beta-Phenylethyl-oxy-acetyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 152

H-Phenylalanyl-Lysyl-Alanyl-{(2S)-2-Amino-3-cyclohexylpropanoyl}-{(2S)-2-Amino-3-cyclohexylpropanoyl}-Leucyl-{(2R/S)-2-Amino-4,4,4-trifluorobutanoyl}-Arginyl-OH

FAB+ MS: (M+H)+ =1079

EXAMPLE 153

H-Phenylalanyl-Lysyl-Alanyl-(3-{2'-Perhydronaphthyl)alanyl}-Alanyl-Leucyl-DAlanyl-Arginyl-OH

FAB+ MS: (M+H)+ =983

EXAMPLE 154

H-Phenylalanyl-Lysyl-Alanyl-{3-(2'-Naphthyl)alanyl}-Alanyl-Leucyl-DAlanyl-Arginyl-OH
FAB+ MS: (M+H)+ =973

EXAMPLE 155

H-Phenylalanyl-Lysyl-Alanyl-{(2S)-2-Amino-3-cyclohexylpropanoyl}-{(2S)-2-Amino-3-cyclohexylpropanoyl}-Leucyl-{(2R/S)-2-Amino-4,4,4-trifluorobutanoyl}-Arginyl-OH
FAB+ MS: (M+H)+ =1079

EXAMPLE 156

2-Methylthioacetyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 157

H-Phenylalanyl-Lysyl-Alanyl-{3-(1'-Naphthyl)alanyl}-Alanyl-Leucyl-DAlanyl-Arginyl-OH
FAB+ MS: (M+H)+ =973

EXAMPLE 158

H-Phenylalanyl-Lysyl-Alanyl-{3-(2'-(5'-tert-Butylthienyl))alanyl(R/S)}-Alanyl-Leucyl-DAlanyl-Arginyl-OH
FAB+ MS: (M+H)+ =985

EXAMPLE 159

H-Phenylalanyl-Lysyl-Alanyl-{3-(2'-(5'-tert-Butylthienyl))alanyl(R/S)}-Alanyl-Leucyl-DAlanyl-Arginyl-OH
FAB+ MS: (M+H)+ =985

EXAMPLE 160

H-Phenylalanyl-Lysyl-Alanyl-{3-(2'-Thienyl)alanyl(R/S)}-Alanyl-Leucyl-DAlanyl-Arginyl-OH
FAB+ MS: (M+H)+ =929

EXAMPLE 161

H-Phenylalanyl-Lysyl-Alanyl-{(2S)-2-Amino-3-cyclohexylpropanoyl}-{(2'RS,3S)-3-Amino-2-oxo-1-pyrrolidine-{2'-(4'-methyl)}-pentanoyl}-DProlyl-Arginyl-OH
FAB+ MS: (M+H)+ =967

EXAMPLE 162

4-Phenylbutyryl-Lysyl-Alanyl-{(2S)-2-Amino-3-cyclohexylpropanoyl}-Alanyl-Leucyl-(N-Methyl)-DAlanyl-Arginyl-OH

EXAMPLE 163

H-Phenylalanyl-Lysyl-Alanyl-{3-(1'-Perhydronaphthyl)alanyl}-Alanyl-Leucyl-DAlanyl-Arginyl-OH
FAB+ MS: (M+H)+ =983

EXAMPLE 164

H-Phenylalanyl-Lysyl-Alanyl-{(2S)-2-Amino-3-cyclohexylpropanoyl}-Threonyl-Leucyl-DAlanyl-Arginyl-OH
FAB+ MS: (M+H)+ =959

EXAMPLE 165

H-Phenylalanyl-Lysyl-Alanyl-{(2S)-2-Amino-3-cyclohexylpropanoyl}-Glycyl-Leucyl-DAlanyl-Arginyl-OH
FAB+ MS: (M+H)+ =915; Amino Acid Anal.: Phe (0.99), Lys (1.04), Ala (1.92), Cha (1.00), Leu (1.07), Arg (1.02), Gly (0.97)

EXAMPLE 166

H-Penylalanyl-Lysyl-Alanyl-Lysyl-{(2S)-2-Amino-3-cyclohexylpropanoyl}-Leucyl-DAlanyl-Arginyl-OH
FAB+ MS: (M+H)+ =986

EXAMPLE 167

Phenylacetyl-Lysyl-Alanyl-{(2S)-2-Amino-3-cyclohexylpropanoyl}-Alanyl-Leucyl-(N-Methyl)-DAlanyl-Arginyl-OH

EXAMPLE 168

H-Phenylalanyl-Lysyl-Alanyl-Glutamyl-{(2S)-2-Amino-3-cyclohexylpropanoyl}-Leucyl-DAlanyl-Arginyl-OH
FAB+ MS: (M+H)+ =987

EXAMPLE 169

H-{(2S)-2-Amino-4-phenylbutanoyl}-Lysyl-Alanyl-{(2S)-2-Amino-4-phenylbutanoyl}-Alanyl-Leucyl-DAlanyl-Arginyl-OH
FAB+ MS: (M+H)+ =951

EXAMPLE 170

H-Phenylalanyl-Lysyl-Alanyl-{(2S)-2-Amino-4-phenylbutanoyl}-Alanyl-Alanyl-DAlanyl-Arginyl-OH
FAB+ MS: (M+H)+ =985

EXAMPLE 171

Pyrazylcarbonyl-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1036

EXAMPLE 172

(N-Methyl)Phenylalanyl-Lysyl-Alanyl-{(2S)-2-Amino-3-cyclohexylpropanoyl}-(N-Hydroxy)Asparaginyl-Leucyl-(N-Methyl)DAlanyl-Arginyl-OH

EXAMPLE 173

3-Cyclopentylpropanoyl-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1054

EXAMPLE 174

(3-Benzoyl)benzoyl-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1138

EXAMPLE 175

{1,2,3,4-Tetrahydronaphthyl-carbonyl($\pm$)}-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+Na)+ =1110

EXAMPLE 176

(N-Methyl)phenylalanyl-Lysyl-Glycyl-$\psi${CH$_2$CO—NH}-{(2S)-2-Amino-3-cyclohexylpropanoyl}-Alanyl-Leucyl-(N-Methyl)DAlanyl-Arginyl-OH

EXAMPLE 177

H-Phenylalanyl-Lysyl-Nipecotyl(±)-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1051

EXAMPLE 178

4-Phenylbutanoyl-Lysyl-Histidyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1076

EXAMPLE 179

H-Phenylalanyl-Lysyl-Alanyl-{(2S)-2-Amino-4-phenylbutanoyl}-{Aminocyclohexyl-3-carbonyl(R/S)}-DAlanyl-Arginyl-OH

FAB+ MS: (M+H)+ =878

EXAMPLE 180

H-Phenylalanyl-Lysyl-Alanyl-{(2S)-2-Amino-4-phenylbutanoyl}-{Aminocyclohexyl-3-carbonyl(R/S)}-DAlanyl-Arginyl-OH

FAB+ MS: (M+H)+ =878

EXAMPLE 181

(N-Methyl)Phenylalanyl-Lysyl-Glycyl-ψ{S(O)$_2$—NH}-{(2S)-2-Amino-3-cyclohexylpropanoyl}-Alanyl-Leucyl-(N-Methyl)DAlanyl-Arginyl-OH

EXAMPLE 182

H-Phenylalanyl-Lysysl-Alanyl-Threonyl-{(2S)-2-Amino-3-cyclohexylpropanoyl}-Leucyl-DAlanyl-Arginyl-OH

FAB+ MS: (M+H)+ =959

EXAMPLE 183

H-Phenylalanyl-Lysyl-Alanyl-Alanyl-{(2S)-2-Amino-3-cyclohexylpropanoyl}-Leucyl-DAlanyl-Arginyl-OH FAB+ MS: (M+H)+ =929; Amino Acid Anal.: Phe (1.05), Lys (0.97), Ala (2.69), Cha (0.93), Leu (1.20), Arg (1.03)

EXAMPLE 184

H-Phenylalanyl-Lysyl-Glycyl-{(2S)-2-Amino-3-cyclohexylpropanoyl}-Leucyl-DAlanyl-Arginyl-OH FAB+ MS: (M+H)+ =915; Amino Acid Anal.: Phe (1.10), Lys (1.04), Ala (1.93), Cha (1.01), Leu (1.23), Arg (1.08), Gly (0.95)

EXAMPLE 185

H-Phenylalanyl-Lysyl-DAlanyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1011

EXAMPLE 186

(N-Methyl)Phenylalany-1-Lysyl-Alanyl-{(2S)-2-Amino-3-cyclohexylpropanoyl}-Alanyl-Leucyl-ψ{C∫C}-Glycyl-Arginyl-OH The Boc-Leu-Gly-OH alkyne isotere is prepared in analogy to the procedure described in the literature ('van Marsenille, M.; Gysen, C.; Tourwe, D.; van Vinst, G. Bull. Soc. Chim. Belg. 1986, 108, 825.) and incorporated into the peptide by classical solution methods as exemplified by the methods described in "Peptide Synthesis", Second Edition, M. Bodanszky, Y. S. Klausner, and M. A. Ondetti (1976).

EXAMPLE 187

H-Alanyl-Lysyl-Alanyl-{(2S)-2-Amino-3-cyclohexylpropanoyl}-{(2S)-2-Amino-3-cyclohexylpropanoyl}-leucyl-DAlanyl-Arginyl-OH FAB+ MS: (M+H)+ =935; Amino Acid Anal.: Lys (0.99), Ala (2.48), Cha (1.74), Leu (1.03), Arg (0.98)

EXAMPLE 188

H-Phenylalanyl-Lysyl-Alanyl-{(2S)-2-Amino-3-cyclohexylpropanoyl}-{(2S)-2-Amino-3-cyclohexylpropanoyl}-Leucyl-Alanyl-Arginyl-OH

FAB+ MS: (M+H)+ =1011

EXAMPLE 189

H-Phenylalanyl-Lysyl-Glycyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =997; Amino Acid Anal.: Phe (0.99), Lys (1.01), Ala (0.73), Cha (1.80), Leu (1.06), Arg (0.99), Gly (0.95).

EXAMPLE 190

H-Glycyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =921; Amino Acid Anal.: Phe (0.97), Lys (1.03), Ala (1.70), Cha (1.85), Leu (1.09), Arg (1.00)

EXAMPLE 191

(N-Methyl)Phenylalanyl-Lysyl-Glycyl-ψ{C(=S)—NH}-{(2S)-2-Amino-3-cyclohexylpropanoyl}-Alanyl-Leucyl-(N-Methyl)DAlanyl-Arginyl-OH The Boc-Glycyl-ψ{C(=S)—NH}-{(2S)-2-Amino-3-cyclohexylpropanoyl}-OH dipeptide is prepared in analogy to the procedure described in the literature (Maziak, L.; Lajoie, G.; Belleau, B. J. Am. Chem. Soc. 1986, 108, 182.) and incorporated into the peptide by classical solution methods as exemplified by the methods described in "Peptide Synthesis", Second Edition, M. Bodanszky, Y. S. Kalusner, and M. A. Ondetti (1976).

EXAMPLE 192

H-Phenylalanyl-Lysyl-Alanyl-{(2S)-2-Amino-3-cyclohexylpropanoyl}-{(2S)-2-Amino-3-cyclohexylpropanoyl}-Leucyl-Glycyl-Arginyl-OH FAB+ MS: (M+H)+ =997; Amino Acid Anal.: Phe (0.97), Lys (1.00), Ala (0.98), Cha (1.82), Leu (1.07), Arg (0.98), Gly (0.80)

EXAMPLE 193

H-Penicillaminyl*-Lysyl-Alanyl-{(2S)-2-Amino-3-cyclohexylpropanoyl}-Cysteinyl*-Leucyl-DAlanyl-Arginyl-OH The compound was prepared in analogy to Example 334.

FAB+ MS: (M+H)+ =943

EXAMPLE 194

H-DPenicillaminyl*-Lysyl-Alanyl-{(2S)-2-Amino-3-cyclohexylpropanoyl}-Cysteinyl*-Leucyl-DAlanyl-Arginyl-OH The compound was prepared in analogy to Example 334.
FAB+ MS: (M+H)+ =943

EXAMPLE 195

Benzoyl-Penicillaminyl*-Lysyl-Alanyl-{(2S)-2-Amino-3-cyclohexylpropanoyl}-Cysteinyl*-Leucyl-DAlanyl-Arginyl-OH The compound was prepared in analogy to Example 334.
FAB+ MS: (M+H)+ =1047

EXAMPLE 196

Benzoyl-Penicillaminyl*-Lysyl-Alanyl-{(2S)-2-Amino-3-cyclohexylpropanoyl}-Cysteinyl*-Leucyl-DAlanyl-Arginyl-OH The compound was prepared in analogy to Example 334.
FAB+ MS: (M+H)+ =1047

EXAMPLE 197

H-Phenylalnyl-Lysyl-Alanyl-{(2S)-2-Amino-3-cyclohexylpropanoyl}-DLysyl-Leucyl-DAlanyl-Arginyl-OH
FAB+ MS: (M+H)+ =986

EXAMPLE 198

(N-Methyl)phenylalanyl-Lysyl-Alanyl-{(2S)-2-Amino-3-cyclohexylpropanoyl}-Alanyl-Leucyl-ψ{CH$_2$—O}-Glycyl-Arginyl-OH The Boc-Leucyl-ψ{CH$_2$—O}-Glycyl-OH dipeptide is prepared in analogy to the procedure described in the literature (Rubini, E.; Gilson, C.; Selinger, Z.; Chorev, M. *Tetrahedron* 1986, 42, 6039.) and incorporated into the peptide by classical solution methods as exemplified by the methods described in "Peptide Synthesis", Second Edition, M. Bodanszky, Y. S. Klausner, and M. A. Ondetti (1976).

EXAMPLE 199

H-Phenylalanyl-Lysyl-Alanyl-{(2S)-2-Amino-3-cyclohexylpropanoyl}-DAlanyl-Leucyl-DAlanyl-Arginyl-OH
FAB+ MS: (M+H)+ =929

EXAMPLE 200

H-Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-(4-NH$_2$)Phenylalanyl-OH
FAB+ MS: (M+H)+ =1011

EXAMPLE 201

H-Phenylalanyl-Lysyl-Alanyl-{(2S)-2-Amino-3-cyclohexylpropanoyl}-{(2R)-2-Amino-3-cyclohexylpropanoyl}-Leucyl-DAlanyl-Arginyl-OH
FAB+ MS: (M+H)+ =1011

EXAMPLE 202

H-Phenylalanyl-Lysyl-Alanyl-{(2S)-2-Amino-3-cyclohexylpropanoyl}-{(2S)-2-Amino-3-cyclohexylpropanoyl}-DAlanyl-DAlanyl-Arginyl-OH
FAB+ MS: (M+H)+ =969

EXAMPLE 203

H-Phenylalanyl-Lysyl-Alanyl-Phenylalanyl-Alanyl-Leucyl-DAlanyl-Arginyl-OH
FAB+ MS: (M+H)+ =923

EXAMPLE 204

H-{2-Aminooctanoyl(±)}-Phenylalanyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1196

EXAMPLE 205

H-Phenylalanyl-Lysyl-Alanyl-{(R/S)-Perhydroindole-2-carbonyl}-Alanyl-Leucyl-DAlanyl-Arginyl-OH
FAB+ MS: (M+H)+ =927

EXAMPLE 206

(N-Methyl)Phenylalanyl-Lysyl-Alanyl-{(2S)-2-Amino-3-cyclohexylpropanoyl}-Alanyl-Leucyl-ψ{CH$_2$—S}-Glycyl-Arginyl-OH The Boc-Leucyl-ψ{CH$_2$—S}-Glycyl-OH dipeptide is prepared in analogy to the procedure described in the literature (Spatola, A.; Anwer, M.; Rockwell, A.; Gierasch, L. *J. Am. Chem. Soc.* 1986, 108, 825.) and incorporated into the peptide by classical solution methods as exemplified by the methods described in "Peptide Synthesis", Second Edition, M. Bodanszky, Y. S. Klausner, and M. A. Ondetti (1976).

EXAMPLE 207

H-Phenylalanyl-Lysyl-Alanyl-{(R/S)-Perhydroindole-2-carbonyl}-Alanyl-Leucyl-DAlanyl-Arginyl-OH
FAB+ MS: (M+H)+ =927

EXAMPLE 208

H-Phenylalanyl-Lysyl-Alanyl-{(2S)-2-Amino-3-cyclohexylpropanoyl}-Alanyl-Leucyl-DAlanyl-Arginyl-OH
FAB+ MS: (M+H)+ =929

EXAMPLE 209

H-Phenylalanyl-Lysyl-Alanyl-{(2R/S)-2-Amino-5-phenylpentanoyl}-Alanyl-Leucyl-DAlanyl-Arginyl-OH
FAB+ MS: (M+H)+ =951

EXAMPLE 210

H-Phenylalanyl-Lysyl-Alanyl-{(2R/S)-2-Amino-5-phenylpentanoyl}-Alanyl-Leucyl-DAlanyl-Arginyl-OH
FAB+ MS: (M+H)+ =951

EXAMPLE 211

H-Phenylalanyl-Lysyl-Alanyl-{(2S)-2-Amino-3-cyclohexylpropanoyl}-{(2S)-2-Amino-3-cyclohexylpropanoyl)-Leucyl-DAlanyl-Arginyl-Glycyl-OH
FAB+ MS: (M+H)+ =1068

EXAMPLE 212

(N-Methyl)Phenylalanyl-Lysyl-Alanyl-{(2S)-2-Amino-3-cyclohexylpropanoyl}-Alanyl-Leucyl-ψ{C(=O)—O}-Glycyl-Arginyl-OH The Boc-Leucyl-ψ{C(=O)—O}-Glycyl-OH dipeptide is prepared in analogy to the procedure described in the literature (Roy, J.; Gazis, D.; Shakman, R.; Schwartz, I. L. *Int. J. Peptide Protein Res.* 1982, 20, 35.) and incorporated into the peptide by classical solution methods as exemplified by the methods described in "Peptide Synthesis", Second Edition, M. Bodanszky, Y. S. Klausner, and M. A. Ondetti (1976).

EXAMPLE 213

H-Phenylalanyl-Lysyl-Alanyl-{(2S)-2-Amino-3-cyclohexylpropanoyl}-{(2S)-2-Amino-3-cyclohexylpropanoyl)-Leucyl-DAlanyl-Glycyl-Arginyl-OH
FAB+ MS: (M+H)+ =1068

EXAMPLE 214

H-phenylalanyl-Lysyl-Alanyl-{(trans-3-propyl)-Prolyl(R/S)}-Alanyl-Leucyl-DAlanyl-Arginyl-OH
FAB+ MS: (M+H)+ =915

EXAMPLE 215

H-Phenylalanyl-Lysyl-Alanyl-{(trans-3-propyl)-Prolyl(R/S)}-Alanyl-Leucyl-DAlanyl-Arginyl-OH
FAB+ MS: (M+H)+ =915

EXAMPLE 216

H-Phenylalanyl-Lysyl-(3,5-di-I)Tyrosyl-{(2S)-2-Amino-3-cyclohexylpropanoyl}-Alanyl-Leucyl-DAlanyl-Arginyl-OH
FAB+ MS: (M+H)+ =1273

EXAMPLE 217

H-Phenylalanyl-Lysyl-Alanyl-{(2S)-2-Amino-3-cyclohexylpropanoyl}-DTryptophyl-Leucyl-DAlanyl-Arginyl-OH
FAB+ MS: (M+H)+ =1044

EXAMPLE 218

H-Phenylalanyl-Lysyl-Alanyl-{(2S)-2-Amino-3-cyclohexylpropanoyl}-Tryptophyl-Leucyl-DAlanyl-Arginyl-OH
FAB+ MS: (M+H)+ =1044

EXAMPLE 219

(N-Methyl)Phenylalanyl-Lysyl-Alanyl-{(2S)-2-Amino-3-cyclohexylpropanoyl}-Alanyl-Leucyl-ψ{C(=O)—S}-Glycyl-Arginyl-OH The Boc-Leucyl-ψ{C(=O)—S}-Glycyl-OH dipeptide is prepared by standard coupling of Boc-leucine mixed anhydride with thiolacetic acid and incorporated into the peptide by classical solution methods as exemplified by the methods described in "Peptide Synthesis", Second Edition, M. Bodanszky, Y. S. Klausner, and M. A. Ondetti (1976).

EXAMPLE 220

H-Phenylalanyl-Lysyl-Alanyl-{(2S)-2-Amino-3-cyclohexylpropanoyl}-DPhenylalanyl-Leucyl-DAlanyl-Arginyl-OH
FAB+ MS: (M+H)+ =1005; Amino Acid Anal.: Phe (2.00), Lys (1.04), Ala (1.86), Cha (1.26), Leu (1.07), Arg (1.04)

EXAMPLE 221

H-Phenylalanyl-Lysyl-Alanyl-DTryptophyl-{(2S)-2-Amino-3-cyclohexylpropanoyl}-Leucyl-DAlanyl-Arginyl-OH
FAB+ MS: (M+H)+ =1044

EXAMPLE 222

H-Phenylalanyl-Alanyl-DLysyl-{(2S)-2-Amino-3-cyclohexylpropanoyl}-Alanyl-Leucyl-DAlanyl-Arginyl-OH
FAB+ MS: (M+H)+ =929

EXAMPLE 223

H-Phenylalanyl-Lysyl-(3-I)Tyrosyl-{(2S)-2-Amino-3-cyclohexylpropanoyl}-Alanyl-Leucyl-DAlanyl-Arginyl-OH
FAB+ MS: (M−H)− =1145

EXAMPLE 224

H-Phenylalanyl-Lysyl-Alanyl-Alanyl-Alanyl-Leucyl-DAlanyl-Arginyl-OH
FAB+ MS: (M+H)+ =847

EXAMPLE 225

Iodoacetyl-Phenylalanyl-Lysyl-Lysyl-{(2S)-2-Amino-3-cyclohexylpropanoyl}-Alanyl-Leucyl-DAlanyl-Arginyl-OH
FAB+ MS: (M+H)+ =1154

EXAMPLE 226

H-Phenylalanyl-Lysyl-Alanyl-(4-NO₂)Phenylalanyl-Alanyl-Leucyl-DAlanyl-Argiyl-OH
FAB+ MS: (M+H)+ =968

EXAMPLE 227

(N-Methyl)Phenylalanyl-Lysyl-Alanyl-{(2S)-2-Amino-3-cyclohexylpropanoyl}-Alanyl-Leucyl-ψ{CH₂C(=O)—O}-Glycyl-Arginyl-OH The Boc-Leu-ψ{CH₂C(=O)}—OH is prepared by Arndt-Eistert synthesis as described in the literature (Wakamiya, T.; Uratani, H.; Teshima, T.; Shiba, T. *Bull. Chem. Soc. Jpn.* 1975, 48, 2401.) Boc-Leucyl-ψ{CH₂C(=O)—O}-Glycyl-OH is prepared in analogy to Example 212. The peptide is prepared by classical solution methods as exemplified by the methods described in "Peptide Synthesis", Second Edition, M. Bodanszky, Y. S. Klausner, and M. A. Ondetti (1976).

EXAMPLE 228

H-Phenylalanyl-Lysyl-Alanyl-(4-NH₂)Phenylalanyl-Alanyl-Leucyl-DAlanyl-Arginyl-OH
FAB+ MS: (M+H)+ =938

EXAMPLE 229

H-Phenylalanyl-Lysyl-Alanyl-{(2S)-2-Amino-3-cyclohexylpropanoyl}-{(2S)-2-Amino-3-cyclohexylpropanoyl}-Leucyl-(N-Methyl)DAlanyl-Arginyl-OH
FAB+ MS: (M+H)+ =1025; Amino Acid Anal.: Ala (1.01), Leu (0.99), Phe (0.96), Cha (197), Lys (1.04), Arg (1.02)

EXAMPLE 230

H-Phenylalanyl-Lysyl-Alanyl-{(2S)-2-Amino-3-cyclohexylpropanoyl}-{(2S)-2-Amino-3-cyclohexylpropanoyl}-(N-Methyl)Leucyl-DAlanyl-Arginyl-OH
FAB+ MS: (M+H)+ =1025; Amino Acid Anal.: Ala (1.94), Phe (1.00), Cha (2.00), Lys (1.03), Arg (1.04)

EXAMPLE 231

H-Phenylalanyl-Lysyl-Cysteinyl*-{(2S)-2-Amino-3-cyclohexylpropanoyl}-{(2S)-2-Amino-3-cyclohexylpropanoyl}-Penicillaminyl*-DAlanyl-Arginyl-OH
The compound was prepared in analogy to Example 334.
FAB+ MS: (M+H)+ =1059

EXAMPLE 232

H-Phenylalanyl-Lysyl-Cysteinyl*-{(2S)-2-Amino-3-cyclohexylpropanoyl}-{(2S)-2-Amino-3-cyclohexylpropanoyl}-DPenicillaminyl*-DAlanyl-Arginyl-OH The compound was prepared in analogy to Example 334.

FAB+ MS: (M+H)+ =1059; Amino Acid Anal.: Ala (0.85), Phe (1.00), Cha (1.98), Lys (0.99), Arg (1.03)

EXAMPLE 233

H-{(2S)-2-Amino-3-cyclohexylpropanoyl}-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =1017; Amino Acid Anal.: Ala (1.88), Leu (1.07), Cha (2.78), Lys (1.02), Arg (1.04)

EXAMPLE 234

(N-Methyl)Phenylalanyl-Lysyl-Alanyl-{(2S)-2-Amino-3-cyclohexylpropanoyl}-Alanyl-Leucyl-ψ{CH$_2$C(=O)—S}-Glycyl-Arginyl-OH The Boc-Leucyl-ψ{CH$_2$C(=O)—S}-Glycyl-OH dipeptide is prepared by standard coupling of Boc-Leu-ψ{CH$_2$C(=O))}—OH, which is prepared as described in Example 227, mixed anhydride with thiolacetic acid and incorporated into the peptide by classical solution methods as exemplified by the methods described in "Peptide Synthesis", Second Edition, M. Bodanszky, Y. S. Klausner, and M. A. Ondetti (1976).

EXAMPLE 235

H-Phenylalanyl-Lysyl-(N-Methyl)Alanyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1025

EXAMPLE 236

H-Phenylalanyl-Lysyl-Alanyl-{(2S)-2-Amino-3-cyclohexylpropanoyl}-{(2S)-2-Amino-3-cyclohexylpropanoyl}-Leucyl-DArginyl-Arginyl-OH

FAB+ (M+H)+ =1096

EXAMPLE 237

Phenoxyacetyl-Lysyl-Lysyl-{(2S)-2-Amino-3-cyclohexylpropanoyl}-{(2S)-2-Amino-3-cyclohexylpropanoyl}-Leucyl-DAlanyl-Arginyl

FAB+ MS: (M+H)+ =1037

EXAMPLE 238

H-Phenylalanyl-Lysyl-Alanyl-{(2S)-2-Amino-3-cyclohexylpropanoyl}-{(3,4-dehydro)Prolyl(R/S)}-Leucyl-DAlanyl-Arginyl-OH

FAB+ MS: (M+H)+ =953

EXAMPLE 239

H-Phenylalanyl-Lysyl-Alanyl-{(2S)-2-Amino-3-cyclohexylpropanoyl}-{(3,4-dehydro)Prolyl(R/S)}-Leucyl-DAlanyl-Arginyl-OH

FAB+ MS: (M+H)+ =953

EXAMPLE 240

(N-Methyl)Phenylalanyl-Lysyl-Alanyl-{(2S)-2-Amino-3-cyclohexylpropanoyl}-Alanyl-Leucyl-ψ{CH=CH}-Glycyl-Arginyl-OH The Boc-Leucyl-ψCH=CH}-Glycyl-OH ethylenic isostere is prepared in analogy to the procedure described in the literature (Spaltenstein, A.; Carpino, P.; Miyake, F.; Hopkins, P. *Tetrahedron Lett.* 986, 27, 2095.) and incorporated into the peptide by classical solution methods as exemplified by the methods described in "Peptide Synthesis", Second Edition, M. Bodanszky, Y. S. Klausner, and M. A. Ondetti (1976).

EXAMPLE 241

H-Phenylalanyl-Lysyl-{(3,4-dehydro)Prolyl(R/S)}-{(2S)-2-Amino-3-cyclohexylpropanoyl}-Alanyl-Leucyl-DAlanyl-Arginyl-OH

FAB+ MS: (M+H)+ =953

EXAMPLE 242

H-Phenylalanyl-Lysyl-{(3,4-dehydro)Prolyl(R/S)}-(2S)-2-Amino-3-cyclohexylpropanoyl}-Alanyl-Leucyl-DAlanyl-Arginyl-OH

FAB+ (M+H)+ =953

EXAMPLE 243

H-Phenylalanyl-Lysyl-Alanyl-{(2S)-2-Amino-3-cyclohexylpropanoyl}-Alanyl-Leucyl-DArginyl-Glycyl-OH

FAB+ MS: (M+H)+ =915

EXAMPLE 244

H-Phenylalanyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1140

EXAMPLE 245

H-Phenylalanyl-Lysyl-Alanyl-Tryptophyl-{(2S)-2-Amino-3-cyclohexylpropanoyl}-Leucyl-DAlanyl-Arginyl-OH

FAB+ MS: (M+H)+ =1044

EXAMPLE 246

H-Phenylalanyl-Lysyl-Alanyl-{(2R)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =1011

EXAMPLE 247

H-Phenylalanyl-Lysyl-Alanyl-DAlanyl-{(2S)-2-Amino-3-cyclohexylpropanoyl}-Leucyl-DAlanyl-Arginyl-OH

FAB+ MS: (M+H)+ =929

EXAMPLE 248

(N-Methyl)Phenylalanyl-Lysyl-Alanyl-{(2S)-2-Amino-3-cyclohexylpropanoyl}-Alanyl-Leucyl-ψ{CH$_2$—CH$_2$}-Glycyl-Arginyl-OH The Boc-Leucyl-ψ{CH$_2$—CH$_2$}-Glycyl-OH isostere is prepared by hydrogenating Boc-Leucyl-ψ{CH=CH}-Glycyl-OH, which is prepared as described in Example 240, with palladium-carbon and incorporated into the peptide in analogy to the synthesis of Example 2.

EXAMPLE 249

H-Phenylalanyl-Lysyl-Alanyl-{(2S)-2-Amino-3-cyclohexylpropanoyl}-Glycyl-DTryptophyl-DAlanyl-Arginyl-OH

FAB+ MS: (M+H)+ =988

EXAMPLE 250

H-Histidyl-Lysyl-Phenylalanyl-Tyrosyl-{(2S)-2-Amino-3-cyclohexylpropanoyl}-Leucyl-DAlanyl-Arginyl-OH

FAB+ MS: (M+H)+ =1087

EXAMPLE 251

H-Phenylalanyl-Lysyl-Glycyl-{(2S)-2-Amino-3-cyclohexylpropanoyl}-Glycyl-Leucyl-DAlanyl-Arginyl-OH FAB+ MS: (M+H)+ =901; Amino Acid Anal.: Phe (1.00), Lys (1.17), Cha (1.07), Leu (1.08), Ala (0.94), Arg (1.07), Gly (1.91)

EXAMPLE 252

H-(4-NO$_2$)Phenylalanyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1185

EXAMPLE 253

H-{(2S)-2-Amino-3-cyclohexylpropanoyl}-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1146

EXAMPLE 254

(N-Methyl)Phenylalanyl-Lysyl-Alanyl-{(2S)-2-Amino-3-cyclohexylpropanoyl}-Alanyl-Leucyl-ψ{C(=O)—CH$_2$}-Glycyl-Arginyl-OH The Boc-Leucyl-ψ{C(=O)—CH$_2$}-Glycyl-OH isostere is prepared in analogy to the procedure described in the literature (McMurray, J.; Dyckes, D. *J. Org. Chem.* 1985, 50, 1112.) and incorporated into the peptide by classical solution methods as exemplified by the methods described in "Peptide Synthesis", Second Edition, M. Bodanszky, Y. S. Klausner, and M. A. Ondetti (1976).

EXAMPLE 255

H-(3-NO$_2$)Tyrosyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1201

EXAMPLE 256

H-Tryptophyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1179

EXAMPLE 257

H-{3-(2'-Thienyl)alanyl(R/S)}-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1146

EXAMPLE 258

H-{3-(2'-Thienyl)alanyl(R/S)}-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1146

EXAMPLE 259

H-(4-CH$_3$)Phenylalanyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1154

EXAMPLE 260

(N-Methyl)Phenylalanyl-Lysyl-Alanyl-{(2S)-2-Amino-3-cyclohexylpropanoyl}-Alanyl-Leucyl-ψ{CH(—OH)—CH$_2$})-Glycyl-Arginyl-OH The Boc-Leucyl-ψ{C(=O)—CH$_2$}-Glycyl-OH isostere is prepared in analogy to the procedure described in the literature (McMurray, J.; Dyckes, D. *J. Org. Chem.* 1985, 50, 1112.), reduced to Boc-Leucyl-ψ{CH(—OH)—CH$_2$}-Glycyl-OH with sodium borohydride in methanol and incorporated into the peptide by classical solution methods as exemplified by the methods described in "Peptide Synthesis", Second Edition, M. Bodanszky, Y. S. Klausner, and M. A. Ondetti (1976).

EXAMPLE 261

H-{3-(2'-(5'-tert-Butylthienyl))alanyl(±)}-Lysyl-Aspartyl-{(2S)-2-Amino-3-cyclohexylpropanoyl)}-{(2S)-2-Amino-3-cyclohexylpropanoyl}-Leucyl-DArginyl-Arginyl-OH

FAB+ MS: (M+H)+ =1202

EXAMPLE 262

H-Phenylalanyl-Lysyl-Alanyl-{(2S)-2-Amino-3-cyclohexylpropanoyl}-Glycyl-Leucyl-Glycyl-Arginyl-OH FAB+ MS: (M+H)+ =901; Amino Acid Anal.: Phe (1.07), Lys (0.97), Ala (1.10), Cha (1.05), Gly (1.64), Leu (1.06), Arg (1.15)

EXAMPLE 263

H-Histidyl-Lysyl-Alanyl-{(2S)-2-Amino-3-cyclohexylpropanoyl}-(4-NH$_2$)Phenylalanyl-Leucyl-DAlanyl-(4-NH$_2$)Phenylalanyl-OH

FAB+ MS: (M+H)+ =1016

EXAMPLE 264

H-(4-NH$_2$)Phenylalanyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1155

EXAMPLE 265

H-(3-NH$_2$)Tyrosyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1171

EXAMPLE 266

H-Phenylalanyl-Lysyl-Alanyl-{(2S)-2-Amino-3-cyclohexylpropanoyl}-Phenylalanyl-Leucyl-DAlanyl-Arginyl-OH FAB+ MS: (M+H)+ =1005; Amino Acid Anal.: Phe (1.98), Lys (1.00), Ala (1.90), Cha (1.07), Leu (1.07), Arg (1.04)

EXAMPLE 267

(N-Methyl)Phenylalanyl-Lysyl-Alanyl-{(2S)-2-Amino-3-cyclohexylpropanoyl}-Alanyl-Leucyl-ψ{C(=CH$_2$)—CH$_2$}-Glycyl-Arginyl-OH The Boc-Leucyl-ψ{C(=CH$_2$)—CH$_2$}-Glycyl-OH isostere is prepared by condensing methylenetriphenylphosphorane and Boc-Leucyl-ψ{CO—CH$_2$}-Glycyl-OH which is prepared as described in the literature (McMurray, J.; Dyckes, D. *J. Org. Chem.* 1985, 50, 1112.), and incorporated into the peptide by classical solution methods as exemplified by the methods described in "Peptide Synthesis", Second Edition, M. Bodanszky, Y. S. Klausner, and M. A. Ondetti (1976).

EXAMPLE 268

H-Phenylalanyl-Lysyl-Alanyl-Phenylalanyl-{(2S)-2-Amino-3-cyclohexylpropanoyl}-Leucyl-DAlanyl-Arginyl-OH FAB+ MS: (M+H)+ =1005; Amino Acid Anal.: Phe (1.98), Lys (1.00), Ala (1.89), Cha (1.10), Leu (1.08), Arg (1.05)

EXAMPLE 269

H-(1-CH$_3$)Histidyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H)+ =1144

EXAMPLE 270

H-(3-CH$_3$)Histidyl-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH

FAB+ MS: (M+H) + =1144

EXAMPLE 271

H-Phenylalanyl-Lysyl-Aspartyl-{(2S)-2-Amino-3-cyclohexylpropanoyl}-Glutaminyl-Leucyl-Glycyl-Arginyl-OH

FAB+ MS: (M+H) + =1016

EXAMPLE 272

Ac-Histidyl-Lysyl-Aspartyl-{(2S)-2-Amino-3-cyclohexylpropanoyl}-Glutaminyl-Leucyl-DAlanyl-Arginyl-OH FAB+ MS: (M+H)+ =1062 ; Amino Acid Anal.: His (0.95), Lys (1.00), Asp (0.97), Cha (0.9), Gln (1.03), Leu (1.05), Ala (0.97), Arg (1.03)

EXAMPLE 273

H-Phenylalanyl-Lysyl-}(2S)-2-Amino-3-cyclohexylpropanoyl}-Alanyl-Alanyl-Leucyl-DAlanyl-Arginyl-OH FAB+ MS: (M+H)+ =929; Amino Acid Anal.: Phe (1.00), Lys (1.01), Cha (0.96), Ala (2.92), Leu (1.05), Arg (1.02)

EXAMPLE 274

H-Phenylalanyl-Lysyl-Alanyl-{(2S)-2-Methylamino-3-cyclohexylpropanoyl}-{(2S)-2-Amino-3-cyclohexylpropanoyl}-Leucyl-DAlanyl-Arginyl-OH FAB+ MS: (M+H)+ = 1025; Amino Acid Anal.: Ala (1.63), Leu (1.04), Phe (0.96), Cha (0.95), Lys (0.97), Arg (1.03)

EXAMPLE 275

(N-Methyl)Phenylalanyl-Lysyl-Alanyl-{(2S)-2-Amino-3-Cyclohexylpropanoyl}-Alanyl-Leucyl-ψ{C(=O)—N(OMe)}-Glycyl-Arginyl-OH The Boc-N(OMe)-Glycyl-OH is prepared as described in the literature (Ottenheijm, H.; Herscheid, *J. Chem. Rev.* 1986, 86, 697.), and incorporated into the peptide by classical solution methods as exemplified by the methods described in "Peptide Synthesis", Second Edition, M. Bodanszky, Y. S. Klausner, and M. A. Ondetti (1976).

EXAMPLE 276

Benzoyl-Penicillaminyl*-Lysyl-Alanyl-}(2S)-2-Amino-3-cyclohexylpropanoyl}-{(2S)-2-Amino-3-cyclohexylpropanoyl}-Leucyl-DCysteinyl*-Arginyl-OH The compound was prepared in analogy to Example 334.

FAB+ MS: (M+H)+ =1129; Amino Acid Anal.: Ala (0.98), Leu (1.01), Cha (1.90), Lys (0.99), Arg (1.03)

EXAMPLE 277

H-DPenicillaminyl*-Lysyl-Alanyl-{(2S)-2-Amino-3-cyclohexylpropanoyl}-{(2S)-2-Amino-3-cyclohexylpropanoyl}-Leucyl-DCysteinyl*-Arginyl-OH

FAB+ MS: (M+H)+ = 1025

EXAMPLE 278

H-Phenylalanyl-Lysyl-Alanyl-{(2S)-2-Amino-3-cyclohexylpropanoyl}-{(2S)-2-Methylamino-3-cyclohexylpropanoyl}-Leucyl-DAlanyl-Arginyl-OH FAB+ MS: (M+H)+ = 1025; Amino Acid Anal.: Ala (1.89), Leu (1.04), Phe (0.96), Cha (0.99), Lys (1.00), Arg (1.08)

EXAMPLE 279

Benzoyl-DPenicillaminyl*-Lysyl-Alanyl-{(2S)-2-Amino-3-cyclohexylpropanoyl)-{(2S)-2-Amino-3-cyclohexylpropanoyl}-Leucyl-DCysteinyl*-Arginyl-OH FAB+ MS: (M+H)+ =1129; Amino Acid Anal.: Ala (0.84), Leu (0.88), Cha (2.01), Lys (1.01), Arg (1.04)

EXAMPLE 280

H-Phenylalanyl-Lysyl-Glycyl-{(2S)-2-Amino-3-cyclohexylpropanoyl}-Glycyl-Leucyl-Glycyl-Arginyl-OH FAB+ MS: (M+H)+ = 887 Amino Acid Anal Phe (1.02), Lys (1.02), Cha (1.03), Leu (1.09), Arg (1.05), Gly (2.82)

EXAMPLE 281

(N-Methyl)Phenylalanyl-Lysyl-Alanyl-{(2S)-2-Amino-3-cyclohexylpropanoyl}-Gly-ψ{PO(OH)—NH}-Leucyl-Gly-Arginyl-OH The Cbz-Gly-ψ{PO(OH)-NH}-Leucyl-Gly-OH is prepared as described in the literature (Bartlett, P.; Marlowe, C. *Biochemistry* 1987, 26, 8554.), and incorporated into the peptide by classical solution methods as exemplified by the methods described in "Peptide Synthesis", Second Edition, M. Bodanszky, Y. S. Klausner, and M. A. Ondetti (1976).

EXAMPLE 282

H-Phenylalanyl-Lysyl-Alanyl-DPhenylalanyl-Glycyl-Leucyl-DAlanyl-Arginyl-OH

FAB+ MS: (M+H)+ =909; Amino Acid Anal.: Phe (1.93), Lys (0.99), Ala (2.00), Gly (0.98), Leu (1.08), Arg (1.03)

EXAMPLE 283

H-Phenylalanyl-Lysyl-Alanyl-{(2S)-2-Amino-3-cyclohexylpropanoyl}-Glycyl-Phenylalanyl-DAlanyl-Arginyl-OH FAB+ MS: (M+H)+ =949; Amino Acid Anal.: Phe (2.14), Lys (.97), Ala (1.77), Cha (1.04), Gly (0.99), Arg (1.13)

EXAMPLE 284

H-Phenylalanyl-Lysyl-Alanyl-{(2S)-2-Amino-3-cyclohexylpropanoyl}-Glycyl-DPhenylalanyl-DAlanyl-Arginyl-OH FAB+ MS: (M+H)+ =949; Amino Acid Anal.: Phe (1.96), Lys (1.00), Ala (2.01), Cha (1.02), Gly (1.00), Arg (1.03)

EXAMPLE 285

H-Phenylalanyl-Lysyl-Alanyl-{(2S)-2-Amino-3-cyclohexylpropanoyl}-Glycyl-Tryptophyl-DAlanyl-Arginyl-OH FAB+ MS: (M+H)+ =988; Amino Acid Anal.: Phe (1.02), Lys (1.04), Ala (1.84), Cha (1.04), Arg (1.11), Gly (0.82), Trp (0.75)

EXAMPLE 286

H-Phenylalanyl-Lysyl-Alanyl-{(2S)-2-Amino-3-cyclohexylpropanoyl}-{(2S)-2-Amino-3-cyclohexylpropanoyl}-Leucyl-Alanyl-DArginyl-OH

FAB+ MS: (M+H)+ =1011

EXAMPLE 287

(N-Methyl)Phenylalanyl-Lysyl-Alanyl-{(2S)-2-Amino-3cyclohexylpropanoyl}-Gly-$\psi${PO(OMe)—NH}-Leucyl-Gly-Arginyl-OH The Cbz-Gly-$\psi${PO(OMe)—NH}-Leucyl-Gly-OH is prepared in analogy to the procedure described in the literature (Bartlett, P.; Marlowe, C. Biochemistry 1987, 26, 8554.), and incorporated into the peptide by classical solution methods as exemplified by the methods described in "Peptide Synthesis", Second Edition, M. Bodanszky, Y. S. Klausner, and M. A. Ondetti (1976).

EXAMPLE 288

H-Phenylalanyl-Lysyl-{(2R)-2-Amino-3-cyclohexylpropanoyl)-Alanyl-Alanyl-Leucyl-DAlanyl-Arginyl-OH

FAB+ MS: (M+H)+ =929

EXAMPLE 289

H-Phenylalanyl-Lysyl-Aspartyl-Methionyl-Glutaminyl-Leucyl-Glycyl-Arginyl-OH

FAB+ MS: (M+H)+ =994; Amino Acid Anal.: Phe (0.91), Lys (1.06), Asp (0.94), Met (0.85), Gln (1.02), Leu (1.07), Gly (0.99), Arg (1.02)

EXAMPLE 290

Ac-Histidyl-Lysyl-Aspartyl-{(2S)-2-Amino-3-cyclohexylpropanoyl}-Glutaminyl-Leucyl-Glycyl-Arginyl-OH

FAB+ MS: (M+H)+ =1048

EXAMPLE 291

H-Phenylalanyl-Lysyl-Alanyl-{(2S)-2-Amino-3-cyclohexylpropanoyl}-Alanyl-Leucyl-D(4-NO$_2$)-Phenylalanyl-Arginyl-OH FAB+ MS: (M+H)+ =1050; Acid Anal.: Phe (0.67), Lys (0.66), Ala (1.59), Cha (0.93), Leu (1.00), D(4-NO$_2$)-Phe (0.92), Arg (1.00)

EXAMPLE 292

H-Phenylalanyl-Lysyl-{(2R/S)-2-Amino-5-phenylpentanoyl}-{(2S)-2-Amino-3-cyclohexylpropanoyl}-Alanyl-Leucyl-DAlanyl-Arginyl-OH FAB+ MS: (M+H)+ =1033; Amino Acid Anal Phe (0.94), Lys (1.00), hhPhe (0.82), Cha (0.93), Ala (2.00), Leu (1.04), Arg (1.01)

EXAMPLE 293

H-Phenylalanyl-Lysyl-{(2R/S)-2-Amino-5-phenylpentanoyl}-{(2S)-2-Amino-3-cyclohexylpropanoyl}-Alanyl-Leucyl-DAlanyl-Arginyl-OH

FAB+ MS: (M+H)+ =1033

EXAMPLE 294

H-Phenylalanyl-Alanyl-Lysyl-{(2S)-2-Amino-3-cyclohexylpropanoyl}-Alanyl-Leucyl-DAlanyl-Arginyl-OH

FAB+ MS: (M+H)+ =929

EXAMPLE 295

H-Phenylalanyl-Lysyl-Alanyl-Alanyl-Leucyl-Alanyl-DAlanyl-Arginyl-OH

FAB+ MS: (M+H)+ =847

EXAMPLE 296

H-Phenylalanyl-Lysyl-Alanyl-{(2S)-2-Amino-3-cyclohexylpropanoyl}-Alanyl-Leucyl-(N-Methyl)-DAlanyl-Arginyl-OH FAB+ MS: (M+H)+ =943; Amino Acid Anal.: Ala (1.94), Leu (1.06), Phe (0.96), Cha (0.94), Lys (0.96), Arg (1.02)

EXAMPLE 297

Formyl-$\psi${NH—CO}-DPhenylalanyl-$\psi${NH—CO}-DLysyl-$\psi${NH—NMeDAla-Arginyl-OH The Formyl-$\psi${NH—CO}-DPhenylalanyl-$\psi${NH—CO}-DLysyl-$\psi${NH—CO}Glycyl-OH fragment is prepared by classical solution methods (exemplified by the methods described in "Peptide Synthesis", Second Edition, M. Bodanszky, Y.S. Klausner, and M. A. Ondetti 1976. ) and is incorporated into the peptide in analogy to Example 2.

EXAMPLE 298

H-Phenylalanyl-Lysyl-Penicillaminyl*-{(2S)-2-Amino-3-cyclohexylpropanoyl}-{(2S)-2-Amino-3-cyclohexylpropanyl}-Leucyl-DCysteinyl*-Arginyl-OH The compound was prepared in analogy to Example 334.

FAB+ MS: (M+H)+ =1101

EXAMPLE 299

H-Phenylalanyl-Lysyl-Asparaginyl-{(2S)-2-Amino-3-cyclohexylpropanoyl}-{(2S)-2-Amino-3-cyclohexylpropanoyl}-Leucyl-DAlanyl-Arginyl-NCH$_3$NH$_2$ The compound was prepared in analogy to Example 38.

FAB+ MS: (M+H)+ =1082; Amino Acid Anal.: Asx (1.02), Ala (0.94), Leu (1.05), Phe (0.98), Cha (1.96), Lys (0.97), Arg (1.06)

EXAMPLE 300

H-Phenylalanyl-Lysyl-Asparaginyl-{(2S)-2-Amino-3-cyclohexylpropanoyl}-{(2S)-2-Amino-3-cyclohexylpropanoyl}-Leucyl-DAlanyl-Arginyl-NHNH$_2$ The compound was prepared in analogy to Example 38.

FAB+ MS: (M+H)+ = 1068; Amino Acid Anal. Asx (0.98), Ala (0.99), Leu (1.08), Phe (100), Cha (1.97), Lys (1.03), Arg (1.04)

EXAMPLE 301

(N-Methyl){(2S)-2-Amino-3-cyclohexylpropanoyl)-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1031; Amino Acid Anal.: Ala (1.87), Leu (1.06), Cha (1.96), Lys (1.01), Arg (1.06)

EXAMPLE 302

(N-Methyl)Phenylalanyl-Lysyl-Alanyl-{(2S)-2-Amino-3-cyclohexylpropanoyl}-(2S)-2-Amino-3-cyclohexylpropanoyl}-Leucyl-DAlanyl-Arginyl-OH FAB+ MS: (M+H)+ = 1025; Amino Acid Anal.: Ala (1.87), MePhe (0.87), Leu (1.06), Cha (1.92), Lys (0.98), Arg (1.04)

EXAMPLE 303

H-Phenylalanyl-Lysyl-Alanyl-{(2S)-2-Amino-3-cyclohexylpropanoyl}-{(2S)-2-Amino-3-cyclohexylpropanoyl}-Alanyl-Glycyl-Arginyl-OH FAB+ MS: (M+H)+ = 955; Amino Acid Anal.: Phe (0.99), Lys (1.03), Ala (1.98), Cha (2.14), Gly (0.91), Arg (1.09)

EXAMPLE 304

H-Phenylalanyl-Lysyl-Glycyl-{(2S)-2-Amino-3-cyclohexylpropanoyl}-{(2S)-2-Amino-3-cyclohexylpropanoyl}-Leucyl-Glycyl-Arginyl-OH FAB+ MS: (M+H)− = 983; Amino Acid Anal.: Phe (1.00), Lys (1.06), Cha (2.18), Gly (1.79), Leu (1.07), Arg (1.08)

EXAMPLE 305

Ac-Phenylalanyl-Lysyl-Alanyl-{(2S)-2-Amino-3-cyclohexylpropanoyl}-Alanyl-Leucyl-DAlanyl-Tyrosyl-OH

FAB+ MS: (M+H)+ = 978

EXAMPLE 306

H-Phenylalanyl-Lysyl-Tyrosyl-{(2S)-2-Amino-3-cyclohexylpropanoyl}-Alanyl-Leucyl-DAlanyl-Arginyl-OH

FAB+ MS: (M+H)+ = 1021

EXAMPLE 307

(N-Methyl)Phenylalanyl-Lysyl-Alanyl-{(2S)-2-Amino-3-cyclohexylpropanoyl}-Gly-ψ{PO(NHMe)—NH}-Leucyl-Gly-Arginyl-OH The Cbz-Gly-ψ{PO(OH)—NH}-Leucyl-Gly-OtBu is prepared in analogy to the procedure described in the literature (Bartlett, P.; Marlowe, C. Biochemistry 1987, 26, 8554.), coupled with methyl amine and deprotected to give Cbz-Gly-ψ{PO(NHMe)—NH}-Leucyl-Gly-OH. Cbz-Gly-ψ}PO(NHMe)—NH}-Leucyl-Gly-OH is incorporated into the peptide by classical solution methods as exemplified by the methods described in "Peptide Synthesis", Second Edition, M. Bodanszky, Y. S. Klausner, and M. A. Ondetti (1976).

EXAMPLE 308

H-Phenylalanyl-Lysyl-Alanyl-{(2S)-2-Amino-3-cyclohexylpropanoyl}-{(2S)-2-Amino-3-cyclohexylpropanoyl}-DLeucyl-DAlanyl-Arginyl-OH

FAB+ MS: (M+H)+ = 1011

EXAMPLE 309

H-Phenylalanyl-Lysyl-Alanyl-{(2S)-2-Amino-3-cyclohexylpropanoyl}-{(2S)-2-Amino-3-cyclohexylpropanoyl}-Leucyl-DAlanyl-Agmatine The peptide was synthesized following the procedure described in Example 1 with the exception that the N-terminal protecting group was not removed at the end of the synthesis. Cleavage of the peptide from the resin was accomplished by transesterification with methanol as described in "Solid Phase Peptide Synthesis" by John M. Stewart and Janis D. Young, Second Edition (1984), p. 91. The methyl ester was hydrolyzed with sodium hydroxide and the peptide then coupled with agmatine sulfate using a DCC mediated coupling procedure. The protecting groups were removed by treatment with liquid HF/anisole.

FAB+ MS: (M+H)+ = 967

EXAMPLE 310

H-Phenylalanyl-Lysyl-Alanyl-{(2S)-2-Amino-3-cyclohexylpropanoyl}-{(2S)-2-Amino-3-cyclohexylpropanoyl}-Sarcosyl-DAlanyl-Arginyl-OH FAB+ MS: (M+H)+ = 969; Amino Acid Anal.: Phe (1.01), Lys (1.04), Ala (1.87), Cha (1.94), Arg (1.08), Sar (1.10)

EXAMPLE 311

H-Phenylalanyl-Lysyl-Alanyl-{(2S)-2-Amino-3-cyclohexylpropanoyl}-Sarcosyl-Leucyl-DAlanyl-Arginyl-OH FAB+ MS: (M+H)+ = 929; Amino Acid Anal: Phe (0.97), Lys (1.00), Ala (1.98), Cha (1.02), Leu (1.04), Arg (1.01), Sar (1.13)

EXAMPLE 312

H-Phenylalanyl-Lysyl-Alanyl-{(2S)-2-Amino-3-cyclohexylpropanoyl}-{(2S)-2-Amino-3-cyclohexylpropanoyl}-Leucyl-Sarcosyl-Arginyl-OH FAB+ MS: (M+H)+ = 1011; Amino Acid Anal.: Phe (0.97), Lys (1.00), Ala (0.96), Cha (1.93), Leu (1.04), Arg (1.03), Sar (0.93)

EXAMPLE 313

(N-Methyl)Phenylalanyl-Lysyl-Alanyl-{(2S)-2-Amino-3-cyclohexylpropanoyl}-Gly-ψ{PO(NMe$_2$)—NH}-Leucyl-Gly-Arginyl-OH The Cbz-Gly-ψ{PO(OH)—NH}-Leucyl-Gly-OtBu is prepared in analogy to the procedure described in the literature (Bartlett, P.; Marlowe, C. Biochemistry 1987, 26, 8554.), coupled with dimethyl amine and deprotected to give Cbz-Gly-ψ{PO(NMe$_2$)—NH}-Leucyl-Gly-OH. Cbz-Gly-ψ{PO(NMe$_2$)-NH)-Leucyl-Gly-OH is incorporated into the peptide by classical solution methods as exemplified by the methods described in "Peptide Synthesis", Second Edition, M. Bodanszky, Y. S. Klausner, and M. A. Ondetti (1976).

EXAMPLE 314

H-Phenylalanyl-Lysyl-Sarcosyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 1011; Amino Acid Anal.: Phe (0.99), Lys (1.02), Leu (1.07), Ala (0.86), Cha (2.12), Arg (1.05), Sar (1.13)

EXAMPLE 315

H-Phenylalanyl-Lysyl-Alanyl-Sarcosyl-{(2S)-2-Amino-3-cyclohexylpropanoyl}-Leucyl-DAlanyl-Arginyl-OH FAB+ MS: (M+H)+ = 929; Amino Acid Anal.: Phe (0.99), Lys (1.04), Ala (1.83), Cha (1.06), Leu (1.08), Arg (1.06), Sar (1.11)

EXAMPLE 316

H-Phenylalanyl-Lysyl-DPhenylalanyl-{(2S)-2-Amino-3-cyclohexylpropanoyl}-Glycyl-Leucyl-DAlanyl-Arginyl-OH FAB+ MS: (M+H)+ = 991; Amino Acid Anal.: Phe (2.00), Lys (1.03), Cha (1.08), Gly (0.95), Leu (1.10), Ala (0.86), Arg (1.07)

EXAMPLE 317

H-phenylalanyl-Lysyl-Alanyl-{(2S)-2-Amino-3-cyclohexylpropanoyl}-Glycyl-Leucyl-DPhenylalanyl-Arginyl-OH FAB+ MS: (M+H)+ = 991; Amino Acid Anal.: Phe (1.95), Lys (0.99), Ala (1.02), Cha (1.04), Gly (0.92), Leu (1.07), Arg (1.05)

EXAMPLE 318

(N-Methyl)Phenylalanyl-Lysyl-Alanyl-{(2S)-2-Amino-3-cyclohexylpropanoyl}-Gly-ψ{PO(NH$_2$)—NH}-Leucyl-Gly-Arginyl-OH The Cbz-Gly-ψ{PO(OH)—NH}-Leucyl-Gly-OtBu is prepared in analogy to the procedure described in the literature (Bartlett, P.; Marlowe, C. *Biochemistry* 1987, 26, 8554.), coupled with ammonia and deprotected to give Cbz-Gly-ψ}PO(NH$_2$)—NH}-Leucyl-Gly-OH. Cbz-Gly-ψ{PO(NH$_2$)—NH}-Leucyl-Gly-OH is incorporated into the peptide by classical solution methods as exemplified by the methods described in "Peptide Synthesis", Second Edition, M. Bodanszky, Y. S. Klausner, and M. A. Ondetti (1976).

EXAMPLE 319

H-Phenylalanyl-Lysyl-Phenylalanyl-{(2S)-2-Amino-3-cyclohexylpropanoyl}-Glycyl-Leucyl-DAlanyl-Arginyl-OH FAB+ MS: (M+H)+ = 991; Amino Acid Anal.: Phe (1.95), Lys (0.97), Gly (0.92), Leu (1.07), Ala (0.93), Arg (1.00)

EXAMPLE 320

H-Phenylalanyl-Lysyl-Alanyl-{(2S)-2-Amino-3-cyclohexylpropanoyl}-Glycyl-Leucyl-Tryptophyl-Arginyl-OH

FAB+ MS: (M+H)+ = 1030

EXAMPLE 321

H-Phenylalanyl-Lysyl-Alanyl-{(2S)-2-Amino-3-cyclohexylpropanoyl}-Glycyl-Leucyl-Phenylalanyl-Arginyl-OH FAB+ MS: (M+H)+ = 991; Amino Acid Anal.: Phe (1.94), Lys (0.99), Ala (1.02), Gly (0.96), Leu (1.07), Arg (1.03)

EXAMPLE 322

Ac-Phenylalanyl-Lysyl-{(2R/S)-2-Amino-5-phenylpentanoyl}-{(2S)-2-Amino-3-cyclohexylpropanoyl}-Alanyl-Leucyl-DAlanyl-Arginyl-OH

FAB+ MS: (M+H)+ = 1075

EXAMPLE 323

Ac-Phenylalanyl-Lysyl-{(2R/S)-2-Amino-5-phenylpentanoyl}-{(2S)-2-Amino-3-cyclohexylpropanoyl}-Alanyl-Leucyl-DAlanyl-Arginyl-OH

FAB+ MS: (M+H)+ = 1075

EXAMPLE 324

Formyl-ψ{NH—CO}-DPhenylalanyl-ψ}NH—CO}-DLysyl-ψ{NH—CO—NH}Glycyl-{(2S)-2-Amino-3-cyclohexylpropanoyl}-Alanyl-Leucyl-NMeDAla-Arginyl-OH The H-DLysyl-DPhenalanyl-NH$_2$ fragment is prepared by classical solution methods (exemplified by the methods described in "Peptide Synthesis", Second Edition, M. Bodanszky, Y. S. Klausner, and M. A. Ondetti 1976.) and is coupled with methyl isocyanoacetate to give Formyl-ψ{NH—CO}-DPhenylalanyl-ψ{NH—CO}-DLysyl-ψ{NH—CO—NH}Glycyl-OMe. It is then hydrolyzed to the corresponding carboxylic acid and incorporated into the peptide by classical solution methods as exemplified by the methods described in "Peptide Synthesis", Second Edition, M. Bodanszky, Y. S. Klausner, and M. A. Ondetti (1976).

EXAMPLE 325

H-Valyl-Lysyl-Alanyl-{(2S)-2-Amino-3-cyclohexylpropanoyl}-Alanyl-Leucyl-DAlanyl-Arginyl-OH FAB+ MS: (M+H)+ = 881; Amino Acid Anal.: Ala (2.93), Val (1.03), Leu (1.02), Cha (0.97), Lys (1.01), Arg (1.01)

EXAMPLE 326

H-Phenylalanyl-Sarcosyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 954; Amino Acid Anal : Phe (1.00), Ala (1.91), Cha (1.98), Leu (1.07), Arg (1.05), Sar (0.63)

EXAMPLE 327

H-Sarcosyl-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ = 935; Amino Acid Anal.: Lys (1.12), Ala (1.48), Cha (2.16), Leu (1.17), Arg (1.23), Sar (0.63)

EXAMPLE 328

H-Phenylalanyl-Lysyl-{(2R/S)-2-Amino-5-phenylpentanoyl}-{(2S)-2-Amino-3-cyclohexylpropanoyl}-Alanyl-Leucyl-Glycyl-Arginyl-OH

FAB+ MS: (M+H)+ = 1019

EXAMPLE 329

H-Phenylalanyl-Lysyl-{(2R/S)-2-Amino-5-phenylpentanoyl}-{(2S)-2-Amino-3-cyclohexylpropanoyl}-Alanyl-Leucyl-Glycyl-Arginyl-OH

FAB+ MS: (M+H)+ = 1019

EXAMPLE 330

H-Phenylalanyl-Lysyl-{(2R/S)-2-Amino-5-phenylpentanoyl}-{(2S)-2-Amino-3-cyclohexylpropanoyl}-Glycyl-Leucyl-Glycyl-Arginyl-OH
FAB+ MS: (M+H)+ =1005

EXAMPLE 331

Hydrocinnamoyl-(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH

EXAMPLE 332

H-Phenylalanyl-Lysyl-{(2R/S)-2-Amino-5-phenylpentanoyl}-{(2S)-2-Amino-3-cyclohexylpropanoyl}-Glycyl-Leucyl-Glycyl-Arginyl-OH
FAB+ MS: (M+H)+ =1005

EXAMPLE 333

(N-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-OH
FAB+ MS: (M+H)+ =957

EXAMPLE 334

N-Benzoyl-DPenicillaminyl-Lysyl-Alanyl-{(2S)-2-Amino-3-cyclohexylpropanoyl}-{(2S)-2-Amino-3-cyclohexylpropanoyl}-Leucyl-DCysteinyl-Arginine Cyclic disulfide N-Benzoyl-DPenicillaminyl(S-4-methylbenzyl)-Lysyl(N-epsilon-Cbz)-Alanyl-{(2S)-2-Amino-3-cyclohexylpropanoyl}{-(2S)-2-Amino-3-cyclohexylpropanoly}-Leucyl-DCycteinyl(S-4-methylbenzyl)-Arginyl(N-guanidino-Tos)-OResin (0.6 g) was prepared by the method of Example 1 and was treated with HF and anisole as illustrated in Example 2. After extraction of the crude peptide by treatment with 2×25 mL of degassed 20% aqueous acetic acid, it was then diluted to 1,500 mL with degassed, distilled water. The pH of the solution was adjusted to 8.0 by the addition of concentrated ammonium hydroxide. Potassium ferricyanide aqueous solution (0.01N) was added dropwise to the stirred solution until a yellow color appeared. The resultant solution was stirred for an additional 30 minutes at room temperature, and the pH was adjusted to 5.0 with glacial acetic acid. Packed Bio-Rad anion exchange resin AGX-4 (10 mL, Cl form) was added, stirred for 30 minutes and filtered. The filtrate was applied to a column containing 150 g XAD-16 molecular adsorbent resin. The sample was desalted by first washing the column with 1 L of distilled water and then eluting from the column with 1 L of 50% aqueous ethanol. The combined ethanol fractions were concentrated to approximately 100 mL in vacuo and lyophilized to a dried powder. The crude peptide was then purified by HPLC as described in Example 2. The compound obtained (12 mg) gave NMR and mass spectra consistent with the proposed structure.
FAB+ MS: (M+H)+ =1129

EXAMPLE 335

H-Phenylalanyl-Lysyl-Alanyl-{(2S)-2-Amino-3-cyclohexylpropanoyl}-Glycyl-DPhenylalanyl-DPhenylalanyl-Arginyl-OH
FAB+ MS: (M+H)+ =1025; Amino Acid Anal.: Phe (2.92), Lys (1.01), Ala (1.01), Gly (1.00), Arg (1.06), Cha (1.04)

EXAMPLE 336

H-Phenylalanyl-Lysyl-Aspartyl-{(2S)-2-Amino-3-cyclohexylpropanoyl}-Alanyl-Leucyl-DArginyl-Arginyl-OH
FAB+ MS: (M+H)+ =1058

EXAMPLE 337

H-Phenylalanyl-Lysyl-{(2R/S)-2-Amino-5-phenylpentanoyl}-{(2S)-2-Amino-3-cyclohexylpropanoyl}-Glycyl-Leucyl-DAlanyl-Arginyl-OH
FAB+ MS: (M+H)+ =1019

EXAMPLE 338

H-Tryptophyl(N-formyl)-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =1078

EXAMPLE 339

H-Phenylalanyl-Lysyl-{(2R/S)-2-Amino-5-phenylpentanoyl}{(2S)-2-Amino-3-cyclohexylpropanoyl}-Glycyl-Leucyl-DAlanyl-Arginyl-OH
FAB+ MS: (M+H)+ =1019

EXAMPLE 340

H-Phenylalanyl-Lysyl-{(2R/S)-2-Amino-5-phenylpentanoyl}-{(2S)-2-Amino-3-cyclohexylpropanoyl}-Alanyl-Leucyl-DArginyl-Arginyl-OH
FAB+ MS: (M+H)+ =1118

EXAMPLE 341

H-Phenylalanyl-Lysyl-{(2R/S)-2-Amino-5-phenylpentanoyl}-{(2S)-2-Amino-3-cyclohexylpropanoyl}-Alanyl-Leucyl-DArginyl-Arginyl-OH
FAB+ MS: (M+H)+ =1118

EXAMPLE 342

H-Phenylalanyl-Lysyl-Aspartyl-{(2S)-2-Amino-3-cyclohexylpropanoyl}-{(2S)-2-Amino-3-cyclohexylpropanoyl}-Leucyl-Arginyl-Arginyl-OH
FAB+ MS: (M+H)+ =1140

EXAMPLE 343

H-phenylalanyl-Lysyl-Aspartyl-Alanyl-{(2S)-2-Amino-3-cyclohexylpropanoyl}-Leucyl-DArginyl-Arginyl-OH
FAB+ MS: (M+H)+ =1058

EXAMPLE 344

H-Phenylalanyl-Lysyl-Aspartyl-Alanyl-Alanyl-Leucyl-DArginyl-Arginyl-OH
FAB+ MS: (M+H)+ =976

EXAMPLE 345

H-{(2S)-2-Amino-3-cyclohexylpropanoyl}-Lysyl-Aspartyl-Methionyl-Glutaminyl-Leucyl-Glycyl-Arginyl-OH
FAB+ MS: (M+H)+ =1000

EXAMPLE 346

H-Phenylalanyl-Lysyl-Alanyl-Methionyl-Glutaminyl-Leucyl-Glycyl-Arginyl-OH
FAB+ MS: (M+H)+ =950

EXAMPLE 347

H-Phenylalanyl-Lysyl-Alanyl-{(2S)-2-Amino-3-cyclohexylpropanoyl}-Glycyl-Leucyl-DTryptophyl-Arginyl-OH
FAB+ MS: (M+H)+ =1030

EXAMPLE 348

H-Phenylalanyl-(S-2-Aminoethyl)Cysteinyl-Alanyl-{(2S)-2-Amino-3-cyclohexylpropanoyl}-{(2S)-2-Amino-3-cyclohexylpropanoyl}-Leucyl-DAlanyl-Arginyl-OH The synthesis, deprotection and cleavage of the resin-bound peptide was carried out as oulined in Examples 1 and 2. The S-(2-aminoethyl)-L-cysteine residue was protected as the N-alpha Boc, N-epsilon Cbz derivative prior to incorporation into the peptide.
FAB+ MS: (M+H)+ =1029

EXAMPLE 349

H-Phenylalanyl-Lysyl-Alanyl-Alanyl-{(2S)-2-Amino-3-cyclohexylpropanoyl}-Leucyl-DArginyl-Arginyl-OH
FAB+ MS: (M+H)+ =1014

EXAMPLE 350

H-Phenylalanyl-Lysyl-Aspartyl-{(2S)-2-Amino-3-cyclohexylpropanoyl}(2S)-2-Amino-3-cyclohexylpropanoyl}-Leucyl-DHistidyl-Arginyl-OH
FAB+ MS: (M+H)+ =1121

EXAMPLE 351

H-Phenylalanyl-Lysyl-Aspartyl-{(2S)-2-Amino-3-cyclohexylpropanoyl}-{(2S)-2-Amino-3-cyclohexylpropanoyl}-Leucyl-DAspartyl-Arginyl-OH
FAB+ MS: (M+H)+ =1099

EXAMPLE 352

H-Phenylalanyl-Lysyl-Alanyl-{(2S)-2-Amino-3-cyclohexylpropanoyl}-Alanyl-Leucyl-DArginyl-Arginyl-OH
FAB+ MS: (M+H)+ =1014

EXAMPLE 353

H-Phenylalanyl-Lysyl-{(2S)-2-Amino-3-cyclohexylpropanoyl}-Alanyl-Alanyl-Leucyl-DArginyl-Arginyl-OH
FAB+ MS: (M+H)+ =1014

EXAMPLE 354

H-Phenylalanyl-Lysyl-Aspartyl-Methionyl-Glutaminyl-Leucyl-DAlanyl-Arginyl-OH
FAB+ MS: (M+H)+ =1008

EXAMPLE 355

H-Phenylalanyl-Lysyl-Alanyl-(N-Methyl)Alanyl-Sarcosyl-Leucyl-DAlanyl-Arginyl-OH
FAB+ MS: (M+H)+ =861

EXAMPLE 356

H-Phenylalanyl-Lysyl-Alanyl-{(2S)-2-Amino-3-cyclohexylpropanoyl}-(N-Methyl)Alanyl-Sarcosyl-DAlanyl-Arginyl-OH
FAB+ MS: (M+H)+ =901

EXAMPLE 357

H-Phenylalanyl-Lysyl-Alanyl-{(2S)-2-Amino-3-cyclohexylpropanoyl}-{(2S)-2-Amino-3-cyclohexylpropanoyl}-(N-Methyl)Alanyl-Sarcosyl-Arginyl-OH
FAB+ MS: (M+H)+ =983

EXAMPLE 358

(N-(2-phenyl)ethyl)Phenylalanyl-Lysyl-Alanyl-{(2S)-2-Amino-3-cyclohexylpropanoyl}-Alanyl-Leucyl-DAlanyl-Arginyl-OH
FAB+ MS: (M+H)+ =1033

EXAMPLE 359

H-Phenylalanyl-Lysyl-Alanyl-Alanyl-Alanyl-Leucyl-DArginyl-Arginyl-OH
FAB+ MS: (M+H)+ =932

EXAMPLE 360

H-Phenylalanyl-Lysyl-Aspartyl-{(2S)-2-Amino-3-cyclohexylpropanoyl}-Glutaminyl-Leucyl-DAlanyl-Arginyl-OH
FAB+ MS: (M+H)+ =1030

EXAMPLE 361

Ac-Phenylalanyl-Lysyl-Aspartyl-Leucyl-Glutaminyl-Leucyl-Glycyl-Arginyl-OH
FAB+ MS: (M+H)+ =1018

EXAMPLE 362

Ac-Phenylalanyl-Lysyl-Aspartyl-Methionyl-Glutaminyl-Leucyl-DAlanyl-Arginyl-OH
FAB+ MS: (M+H)+ =1050

EXAMPLE 363

Ac-Phenylalanyl-Lysyl-Aspartyl-Leucyl-Glutaminyl-Leucyl-DAlanyl-Arginyl-OH
FAB+ MS: (M+H)+ =1032

EXAMPLE 364

H-Phenylalanyl-Lysyl-Aspartyl-{(2S)-2-Amino-3-cyclohexylpropanoyl}-Prolyl-Leucyl-DArginyl-Arginyl-OH
FAB+ MS: (M+H)+ =1084

EXAMPLE 365

H-Phenylalanyl-Lysyl-Aspartyl-{(2S)-2-Amino-3-cyclohexylpropanoyl}-Arginyl-Leucyl-DArginyl-Arginyl-OH
FAB+ MS: (M+H)+ =1143

EXAMPLE 366

H-Phenylalanyl-Lysyl-Aspartyl-[(2S)-2-Amino-3-cyclohexylpropanoyl}-{(2S)-2-Amino-3-cyclohexylpropanoyl}-Leucyl-Arginyl-DArginyl-OH
FAB+ MS: (M+H)+ =1140

EXAMPLE 367

H-Phenylalanyl-Lysyl-Aspartyl-{(2S)-2-Amino-3-cyclohexylpropanoyl}-{(2S)-2-Amino-3-cyclohexylpropanoyl}-Leucyl-DArginyl-DArginyl-OH
FAB+ MS: (M+H)+ =1140

EXAMPLE 368

H-(1-CH$_3$)Histidyl-Lysyl-Aspartyl-Methionyl-Glutaminyl-Leucyl-Glycyl-Arginyl-OH
FAB+ MS: (M+H)+ =998

EXAMPLE 369

H-(3-CH$_3$)Histidyl-Lysyl-Aspartyl-Methionyl-Glutaminyl-Leucyl-Glycyl-Arginyl-OH
FAB+ MS: (M+H)+ =998

EXAMPLE 370

H-Phenylalanyl-Lysyl-Aspartyl-{(2S)-2-Amino-3-cyclohexylpropanoyl}-Glutaminyl-Leucyl-DArginyl-Arginyl-OH
FAB+ MS: (M+H)+ =1115

EXAMPLE 371

H-Phenylalanyl-Lysyl-Alanyl-{(2S)-2-Amino-3-Cyclohexylpropanoyl}-Glycyl-Leucyl-DArginyl-Arginyl-OH
FAB+ MS: (M+H)+ =1000

EXAMPLE 372

H-Phenylalanyl-Lysyl-Aspartyl-Methionyl-Glutaminyl-Leucyl-DArginyl-Arginyl-OH
FAB+ MS: (M+H)+ =1093

EXAMPLE 373

H-Phenylalanyl-Lysyl-Aspartyl-[(2S)-2-Amino-3-cyclohexylpropanoyl]-{(2'R/S,3S)-3-Amino-2-oxo-1-pyrrolidine-}2'-(4'-methyl)}-pentanoyl}-DArginyl-Arginyl-OH
FAB+ MS: (M+H)+ =1070

EXAMPLE 374

H-Phenylalanyl-Lysyl-Aspartyl-{(2S)-2-Amino-3-cyclohexylpropanoyl}-{(2'R/S,3S)-3-Amino-2-oxo-1-pyrrolidine-}2'-(4'-methyl)}-pentanoyl}-DArginyl-Arginyl-OH
FAB+ MS: (M+H)+ =1070

EXAMPLE 375

H-Phenylalanyl-Phenylalanyl-Lysyl-Alanyl-{(2S)-2-Amino-3-cyclohexylpropanoyl}-{(2S)-2-Amino-3-cyclohexylpropanoyl}-DLeucyl-DArginyl-OH
FAB+ MS: (M+H)+ =1087

EXAMPLE 376

H-{3-(1'-Naphthyl)alanyl}-Lysyl-Aspartyl-Methionyl-Glutaminyl-Leucyl-Glycyl-Arginyl-OH
FAB+ MS: (M+H)+ =1043

EXAMPLE 377

H-{3-(2'-Naphthyl)alanyl}-Lysyl-Aspartyl-Methionyl-Glutaminyl-Leucyl-Glycyl-Arginyl-OH
FAB+ MS (M+H)+ =1043

EXAMPLE 378

H-{3-(2'-Thienyl)alanyl(R/S)}-Lysyl-Aspartyl-Methionyl-Glutaminyl-Leucyl-Glycyl-Arginyl-OH
FAB+ MS: (M+H)+ =1000

EXAMPLE 379

H-{3-(2'-Thienyl)alanyl(R/S)}-Lysyl-Aspartyl-Methionyl-Glutaminyl-Leucyl-Glycyl-Arginyl-OH
FAB+ MS: (M+H)+ =1000

EXAMPLE 380

H-{(2S)-2-Amino-4-phenylbutanoyl)-Lysyl-Alanyl-{(2S)-2-Amino-3-cyclohexylpropanoyl}-Alanyl-Leucyl-DArginyl-Arginyl-OH
FAB+ MS: (M+H)+ =1028

EXAMPLE 381

H-{(2R/S)-2-Amino-5-phenylpentanoyl}-Lysyl-Alanyl-{(2S)-2-Amino-3-cyclohexylpropanoyl}-Alanyl-Leucyl-DArginyl-Arginyl-OH
FAB+ MS: (M+H)+ =1042

EXAMPLE 382

H-{(2R/S)-2-Amino-5-phenylpentanoyl}-Lysyl-Alanyl-{(2S)-2-Amino-3-cyclohexylpropanoyl}-Alanyl-Leucyl-DArginyl-Arginyl-OH
FAB+ MS: (M+H)+ =1042

EXAMPLE 383

4-Phenylbutanoyl-Lysyl-Alanyl-{(2S)-2-Amino-3-cyclohexylpropanoyl}-Alanyl-Leucyl-DArginyl-Arginyl-OH
FAB+ MS: (M+H)+ =1013

EXAMPLE 384

H-Phenylalanyl-$\psi${CH$_2$—NH}-Lysyl-Alanyl-{(2S)-2-Amino-3-cyclohexylpropanoyl}-Alanyl-Leucyl-DAlanyl-Arginyl-OH The compound was prepared in analogy to Example 413.
FAB+ MS: (M+H)+ =915; Amino Acid Anal.: Ala (2.97), Leu (1.02), Cha (0.89), Arg (1.01)

EXAMPLE 385

(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH
FAB+ MS: (M+H)+ =957; Amino Acid Anal.: Ala (2.04), Leu (1.05), MePhe (0.87), Cha (0.98), Lys (1.03), Arg (1.01)

EXAMPLE 386

(N-alpha-(2-phenyl)ethyl)Lysyl-Alanyl-{(2S)-2-Amino-3-cyclohexylpropanoyl}-Alanyl-Leucyl-(N-Methyl)DAlanyl-Arginyl-OH
FAB+ MS: (M+H)+ =900

EXAMPLE 387

H-Phenylalanyl-Lysyl-Aspartyl-DMethionyl-Glutaminyl-Leucyl-DArginyl-Arginyl-OH
FAB+ MS: (M+H)+ =1093; Amino Acid Anal.: Asp (0.93), Glx (1.06), Met (0.68), Leu (1.07), Phe (0.97), Lys (0.92), Arg (2.06)

EXAMPLE 388

H-Phenylalanyl-Lysyl-Aspartyl-Methionyl-DGlutaminyl-Leucyl-DArginyl-Arginyl-OH
FAB+ MS: (M+H)+ =1093; Amino Acid Anal. : Asp (0.95), Glx (1.07), Met (0.61), Leu (1.05), Phe (0.98), Lys (0.91), Arg (2.04)

EXAMPLE 389

H-Phenylalanyl-Lysyl-Aspartyl-Methionyl-Glutaminyl-Leucyl-DArginyl-DArginyl-OH
FAB+ MS: (M+H)+ =1093; Amino Acid Anal. Asp (0.97), Glx (1.06), Met (0.68), Leu (1.05), Phe (0.97), Lys (0.92), Arg (2.03)

EXAMPLE 390

H-Phenylalanyl-Lysyl-Aspartyl-Methionyl-Glutaminyl-DLeucyl-DArginyl-Arginyl-OH

FAB+ MS: (M+H)+ =1093; Amino Acid Anal.: Asp (0.98), Glx (1.05), Met (0.57), Leu (1.06), Phe (0.97), Lys (0.92), Arg (2.02) EXAMPLE 391

Phenoxyacetyl-Lysyl-Alanyl-{(2S)-2-Amino-3-cyclohexylpropanoyl}-Alanyl-Leucyl-DArginyl-Arginyl-OH
FAB+ MS: (M+H)+ =1001

EXAMPLE 392

Phenoxypropanoyl-Lysyl-Alanyl-{(2S)-2-Amino-3-cyclohexylpropanoyl}-Alanyl-Leucyl-DArginyl-Arginyl-OH
FAB+ MS: (M+H)+ =1015

EXAMPLE 393

H-Phenylalanyl-Lysyl-Glycyl-Aspartyl-{(2S)-2-Amino-3-cyclohexylpropanoyl}-{(2S)-2-Amino-3-cyclohexylpropanoyl}-Leucyl-DArginyl-Arginyl-OH
FAB+ MS: (M+H)+ =1197

EXAMPLE 394

3-phenylpropanoyl-Lysyl-Alanyl-{(2S)-2-Amino-3-cyclohexylpropanoyl}-Alanyl-Leucyl-DArginyl-Arginyl-OH
FAB+ MS: (M+H)+ =999

EXAMPLE 395

H-Phenylalanyl-Lysyl-3-Aminopropanoyl-{(2S)-2-Amino-3-cyclohexylpropanoyl}-{(2S)-2-Amino-3-cyclohexylpropanoyl}-Leucyl-DArginyl-Arginyl-OH
FAB+ MS: (M+H)+ =1096

EXAMPLE 396

H-Phenylalanyl-(N-Methyl)Alanyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =968

EXAMPLE 397

H-Phenylalanyl-Lysyl-Aspartyl-{(2S)-2-Amino-3-cyclohexylpropanoyl}-{(2S)-2-Amino-3-cyclohexylpropanoyl}-Leucyl-DLysyl-Arginyl-OH
FAB+ MS: (M+H)+ =1112

EXAMPLE 398

H-phenylalanyl-Lysyl-Aspartyl-{(2S)-2-Amino-3-cyclohexylpropanoyl}-{(2S)-2-Amino-3-cyclohexylpropanoyl}-Isoleucyl-DAlanyl-Arginyl-OH
FAB+ MS: (M+H)+ =1055

EXAMPLE 399

H-Phenylalanyl-Lysyl-Aspartyl-Alanyl-Alanyl-Isoleucyl-DAlanyl-Arginyl-OH
FAB+ MS: (M+H)+ =891

EXAMPLE 400

H-Phenylalanyl-Lysyl-DAspartyl-Methionyl-Glutaminyl-Leucyl-DArginyl-Arginyl-OH
FAB+ MS: (M+H)+ =1093; Amino Acid Anal.: Asp (0.97), Glx (1.04), Met (0.59), Leu (1.06), Phe (0.94), Lys (0.89), Arg (2.09)

EXAMPLE 401

H-DPhenylalanyl-Lysyl-Aspartyl-Methionyl-Glutaminyl-Leucyl-DArginyl-Arginyl-OH
FAB+ MS: (M+H)+ =1093; Amino Acid Anal.: Asp (0.95), Glx (1.05), Met (0.59), Leu (1.05), Phe (0.97), Lys (0.93), Arg (2.07)

EXAMPLE 402

(N-Ethyl)Phenylalanyl-Lysyl-Alanyl-{(2S)-2-Amino-3-cyclohexylpropanoyl}-Alanyl-Leucyl-(N-Methyl)DAlanyl-Arginyl-OH
FAB+ MS: (M+H)+ =971; Amino Acid Anal.: Ala (2.02), Leu (1.03), Cha (0.97), Lys (1.01), Arg (0.99)

EXAMPLE 403

(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-NHNH₂
The compound was prepared in analogy to Example 38.
FAB+ MS: (M+H)+ =971; Amino Acid Anal.: Ala (2.01), MePhe (0.85), Leu (1.02), Cha (0.93), Lys (0.98), Arg (0.99)

EXAMPLE 404 tert-Butyloxycarbonyl-Phenylalanyl-Lysyl-Alanyl-{(2S)-2-Amino-3-cyclohexylpropanoyl}-Alanyl-Leucyl-DAlanyl-Arginyl-OH
FAB+ MS: (M+H)+ =1029

EXAMPLE 405

(N-iPr)Phenylalanyl-Lysyl-Alanyl-{(2S)-2-Amino-3-cyclohexylpropanoyl}-Alanyl-Leucyl-(N-Methyl)-DAlanyl-Arginyl-OH
FAB+ MS: (M+H)+ =985; Amino Acid Anal.: Ala (2.07), Leu (0.96), Cha (0.97), Lys (0.99), Arg (0.98)

EXAMPLE 406

H-D(N-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH
FAB+ MS: (M+H)+ =957; Amino Acid Anal.: Ala (1.97), Leu (1.04), Cha (0.93), Lys (0.97), Arg (1.02)

EXAMPLE 407

H-Phenylalanyl-Lysyl-Aspartyl(NHNH₂)-{(2S)-2-Amino-3-cyclohexylpropanoyl}-{(2S)-2-Amino-3-cyclohexylpropanoyl}-Leucyl-(N-Methyl)DAlanyl-Arginyl-NHNH₂
The compound was prepared in analogy to Example 38.
FAB+ MS: (M+H)+ =1083

EXAMPLE 408

H-Phenylalanyl-Lysyl-Aspartyl(NCH₃NH₂)-{(2S)-2-Amino-3-cyclohexylpropanoyl}-{(2S)-2-Amino-3-cyclohexylpropanoyl}-Leucyl-(N-Methyl)DAlanyl-Arginyl-NCH₃NH₂
The compound was prepared in analogy to Example 38.
FAB+ MS: (M+H)+ =1111

EXAMPLE 409

H-phenylalanyl-Lysyl-Alanyl-{(2S)-2-Amino-3-Cyclohexylpropanoyl}-Alanyl-ψ{CH₂—NH}-Leucyl-DAlanyl-Arginyl-OH
The compound was prepared in analogy to Example 413.
FAB+ MS: (M+H)+ =915; Amino Acid Anal.: Ala (1.97), Phe (0.99), Cha (1.79), Lys (1.02), Arg (1.01)

EXAMPLE 410

H-Phenylalanyl-Lysyl-Alanyl-{(2S)-2-Amino-3-cyclohexylpropanoyl}-Alanyl-Leucyl-ψ{CH$_2$—NH}-DAlanyl-Arginyl-OH The compound was prepared in analogy to Example 413.

FAB$^+$ MS: (M+H)$^+$ =915; Amino Acid Anal.: Ala (2.02), Phe (0.97), Cha (0.94), Lys (1.01), Arg (0.82)

EXAMPLE 411

H-Phenylalanyl-Lysyl-Alanyl-ψ{CH$_2$—NH}-{(2S)-2-Amino-3-cyclohexylpropanoyl}-Alanyl-Leucyl-DAlanyl-Arginyl-OH The compound was prepared in analogy to Example 413.

FAB$^+$ MS: (M+H)$^+$ =915; Amino Acid Anal.: Ala (2.06), Leu (1.05), Phe (0.94), Lys (0.99), Arg (0.95)

EXAMPLE 412

H-Phenylalanyl-Lysyl-Alanyl-{(2S)-2-Amino-3-cyclohexylpropanoyl}-ψ{CH$_2$—NH}-Alanyl-Leucyl-DAlanyl-Arginyl-OH The compound was prepared in analogy to Example 413.

FAB$^+$ MS: (M+H)$^+$ =915;Amino Acid Anal.: Ala (2.00), Leu (1.02), Phe (0.97), Lys (1.02), Arg (1.02)

EXAMPLE 413

H-Phenylalanyl-Lysyl-ψ{CH$_2$—NH}-Alanyl-{(2S)-2-Amino-3-cyclohexylpropanoyl}-Alanyl-Leucyl-DAlanyl-Arginyl-OH Commercially available N-alpha-Boc-Lysine(N-epsilon-Cbz) was converted to its N,O-dimethylhydroxamate, which was reduced with lithium aluminum hydride to yield N-alpha-Boc-N-epsilon-Cbz-Lysinal, according to the literature: Nahm, S.; Weinreb, S. M. *Tetrahedron Lett.* 1981, 22, 3815. The peptide chain was then elongated by the method described in Example 1, except that after Boc-Alanine was coupled, the sequence was stopped at agenda A-step 2. N-alpha-Boc-N-epsilon-Cbz-Lysinal (235 mg, 3.5 equivalent mole) in 10 mL of DMF containing 0.1% glacial acetic acid was added, followed by sodium cyanoborohydride (404 mg, 10 equivalent mole). The reaction was allowed to proceed at room temperature for 1 hour. After the peptide resin obtained was washed with DMF (3×10 mL) and methylene chloride (3×10 mL), the next synthetic protocol (Example 1, Agenda A step 2) was initiated. The peptide-resin was then treated as described in Example 2 to yield 27.8 mg of pure product consistent with proposed structure.

FAB$^+$ MS: (M+H)$^+$ =915; Amino Acid Anal.: Ala (1.99), Leu (1.01), Phe (0.94), Cha (0.93), Arg (1.06)

Other amino aldehydes (Boc-Phenylalanal, Boc-(2S)-2-amino-3-cyclohexylpropanal, Boc-Alanal, Boc-Leucinal and Boc-D-Alanal were prepared by literature methods: Anhoury, M. L.; Arickx, M.; Crooy, P.; De Neys, R.; Eliaoiri, J. *J. Chem. Soc. Perkin* 1 1974, 191; Hamada, Y.; Shioiri, T. *Chem. Pharm. Bull.* 1982, 30, 1921.

EXAMPLE 414

H-Phenylalanyl-Lysyl-Aspartyl-Methionyl-Glutaminyl-Leucyl-Glycyl-DArginyl-OH

FAB$^+$ MS: (M+H)$^+$ =994; Amino Acid Anal.: Asp (0.95), Glx (1.08), Gly (0.77), Met (0.56), Leu (1.04), Phe (0.97), Lys (0.94), Arg (1.03)

EXAMPLE 415

H-Phenylalanyl-Lysyl-Aspartyl-Methionyl-Glutaminyl-DLeucyl-Glycyl-Arginyl-OH

FAB$^+$ MS: (M+H)$^+$ =994; Amino Acid Anal.: Asp (0.96), Glx (0.93), Gly (0.67), Met (0.54), Leu (1.06), Phe (0.97), Lys (0.88), Arg (1.05)

EXAMPLE 416

H-Phenylalanyl-Lysyl-Aspartyl-Methionyl-DGlutaminyl-Leucyl-Glycyl-Arginyl-OH

FAB$^+$ MS: (M+H)$^+$ =994; Amino Acid Anal.: Asp (0.97), Glx (1.08), Gly (0.67), Met (0.61), Leu (1.04), Phe (0.98), Lys (0.88), Arg (1.05)

EXAMPLE 417

H-Phenylalanyl-Lysyl-Aspartyl-DMethionyl-Glutaminyl-Leucyl-Glycyl-Arginyl-OH

FAB$^+$ MS: (M+H)$^+$ =994; Amino Acid Anal.: Asp (0.47), Glx (0.32), Gly (0.68), Met (0.64), Leu (1.00), Phe (0.27), Lys (0.30), Arg (1.00)

EXAMPLE 418

H-Phenylalanyl-Lysyl-DAspartyl-Methionyl-Glutaminyl-Leucyl-Glycyl-Arginyl-OH

FAB$^+$ MS: (M+H)$^+$ =994; Amino Acid Anal.: Asp (0.46), Glx (0.28), Gly (0.68), Met (0.59), Leu (1.00), Phe (0.24), Lys (0.29), Arg (1.00)

EXAMPLE 419

H-Phenylalanyl-DLysyl-Aspartyl-Methionyl-Glutaminyl-LeucylGlycyl-Arginyl-OH

FAB$^+$ MS: (M+H)$^+$ =994; Amino Acid Anal.: Asp (0.47), Glx (0.31), Gly (0.84), Met (0.53), Leu (1.04), Phe (0.22), Lys (0.26), Arg (0.96)

EXAMPLE 420

H-Phenylalanyl-Lysyl-Aspartyl-{(2S)-2-Amino-3-cyclohexylpropanoyl}-3-Aminopropanoyl-Leucyl-DArginyl-Arginyl-OH

FAB$^+$ MS: (M+H)$^+$ =1058

EXAMPLE 421

H-Phenylalanyl-Lysyl-Alanyl-{(2S)-2-Amino-3-cyclohexylpropanoyl}-Alanyl-Leucyl-DAlanyl-ψ{CH$_2$—NH}-Arginyl-OH The compound was prepared in analogy to Example 413.

FAB$^+$ MS: (M+H)$^+$ =915; Amino Acid Anal.: Ala (1.80), Leu (1.02), Phe (1.02), Cha (1.00), Lys (0.97)

EXAMPLE 422

(N-(3-Phenyl)propyl)Lysyl-Alanyl-{(2S)-2-Amino-3-cyclohexylpropanoyl}-Alanyl-Leucyl-(N-Methyl)-DAlanyl-Arginyl-OH

FAB$^+$ MS: (M+H)$^+$ =914

EXAMPLE 423

(N,N-di-(3-Phenyl)propyl)Lysyl-Alanyl-{(2S)-2-Amino-3-cyclohexylpropanoyl}-Alanyl-Leucyl-(N-Methyl)DAlanyl-Arginyl-OH FAB$^+$ MS: (M+H)$^+$ =1032;Amino Acid Anal.: Ala (2.10), Leu (1.06), Cha (0.97), Lys (0.93), Arg (1.04)

EXAMPLE 424

H-Phenylalanyl-Lysyl-Aspartyl-Methionyl-Arginyl-Leucyl-Glycyl-Arginyl-OH

FAB+ MS: (M+H)+ =1022; Amino Acid Anal.: Asp (0.62), Gly (0.99), Met (0.49), Leu (1.13), Phe (0.30), Lys (0.35), Arg (1.88)

EXAMPLE 425

H-Phenylalanyl-Lysyl-Arginyl-Methionyl-Glutaminyl-Leucyl-Glycyl-Arginyl-OH

FAB+ MS: (M+H)+ =1035; Amino Acid Anal.: Glx (0.38), Gly(0.83), Met (0.91), Leu (1.13), Phe (0.27), Lys (0.27), Arg (1.96)

EXAMPLE 426

H-Phenylalanyl-Lysyl-Aspartyl-Methionyl-Glutaminyl-Leucyl-Glycyl-Lysyl-OH

FAB+ MS: (M+H)+ =966- Amino Acid Anal.: Asp(0.70), Glx (0.32), Gly (0.94), Met (0.66), Leu (1.19), Phe (0.35), Lys (1.89)

EXAMPLE 427

H-Phenylalanyl-Ornithyl-Aspartyl-Methionyl-Glutaminyl-Leucyl-Glycyl-Arginyl-OH

FAB+ MS: (M+H)+ =980; Amino Acid Anal.: Asp (0.49), Glx (0.32), Gly (0.71), Met (0.65), Leu (1.00), Phe (0.33), Orn (0.25), Arg (1.00)

EXAMPLE 428

H-DPhenylalanyl-Lysyl-Aspartyl-Methionyl-Glutaminyl-Leucyl-Glycyl-Arginyl-OH

FAB+ MS: (M+H)+ =994; Amino Acid Anal.: Asp (0.45), Glx (0.30), Gly (0.70), Met (0.68), Leu (1.00), Phe (0.30), Lys (0.43), Arg (1.00)

EXAMPLE 429

H-Phenylalanyl-Lysyl-Aspartyl-{(2S)-2-Amino-3-cyclohexylpropanoyl}-{(2S)-2-Amino-3-cyclohexylpropanoyl}-Leucyl-Glycyl-Arginyl-Arginyl-OH

FAB+ MS: (M+H)+ =1197

EXAMPLE 430

H-Phenylalanyl-Lysyl-Aspartyl-{(2S)-2-Amino-3-cyclohexylpropanoyl}-{(2S)-2-Amino-3-cyclohexylpropanoyl}-Leucyl-Glycyl-Arginyl-DArginyl-OH

FAB+ MS: (M+H)+ =1197

EXAMPLE 431

3-Phenylpropanoyl-Lysyl-Aspartyl-Methionyl-Glutaminyl-Leucyl-Glycyl-Arginyl-OH

FAB+ MS: (M+H)+ =979

EXAMPLE 432

H-Phenylalanyl-Lysyl-Alanyl-{(2S)-2-Amino-3-cyclohexylpropanoyl}-Arginyl-Leucyl-DAlanyl-Arginyl-OH FAB+ MS: (M+H)+ =1014; Amino Acid Anal.: Ala (1.86), Leu (1.04), Phe (1.00), Cha (0.96), Lys (0.99), Arg (1.97)

EXAMPLE 433

(N-Allyl)Phenylalanyl-Lysyl-Alanyl-{(2S)-2-Amino-3-cyclohexylpropanoyl}-Alanyl-Leucyl-(N-Methyl)-DAlanyl-Arginyl-OH FAB+ MS: (M+H)+ =983; Amino Acid Anal.: Ala (1.98), Leu (1.04), Cha (0.94), Lys (0.96), Arg (1.02)

EXAMPLE 434

(N,N-di-Methyl)Phenylalanyl-Lysyl-Alanyl-{(2S)-2-Amino-3-cyclohexylpropanoyl}-Alanyl-Leucyl-(N-Methyl)DAlanyl-Arginyl-OH FAB+ MS: (M+H)+ =971; Amino Acid Anal.: Ala (2.01), Leu (1.06), Cha (0.88), Lys (0.91), Arg (1.03)

EXAMPLE 435

Pyrazylcarbonyl-Phenylalanyl-Lysyl-Alanyl-{(2S)-2-Amino-3-cyclohexylpropanoyl}-Alanyl-Leucyl-DAlanyl-Arginyl-OH

FAB+ MS: (M+H)+ =1035

EXAMPLE 436

Benzoyl-Phenylalanyl-Lysyl-Alanyl-{(2S)-2-Amino-3-cyclohexylpropanoyl}-Alanyl-Leucyl-DAlanyl-Arginyl-OH

FAB+ MS: (M+H)+ =1033

EXAMPLE 437

2-Pyridylacetyl-Phenylalanyl-Lysyl-Alanyl-{(2S)-2-Amino-3-cyclohexylpropanoyl}-Alanyl-Leucyl-DAlanyl-Arginyl-OH

FAB+ MS: (M+H)+ =1048

EXAMPLE 438

Ac-Phenylalanyl-Lysyl-Alanyl-{(2S)-2-Amino-3-cyclohexylpropanoyl}-Alanyl-Leucyl-DAlanyl-Arginyl-OH

FAB+ MS: (M+H)+ =971

EXAMPLE 439

H-Phenylalanyl-Lysyl-Alanyl-{(2S)-2-Amino-3-cyclohexylpropanoyl}-Alanyl-Leucyl-(N-Bn)Glycyl-Arginyl-OH

FAB+ MS: (M+H)+ =1005

EXAMPLE 440

{(3R/S)-1,2,3,4-Tetrahydroisoquinolin-3-carbonyl}-Lysyl-Alanyl-{(2S)-2-Amino-3-cyclohexylpropanoyl}-Glycyl-Leucyl-DAlanyl-Arginyl-OH FAB+ MS: (M+H)+ =927; Amino Acid Anal.: Gly (0.90), Lys (1.01), Ala (1.78), Cha (0.98), Leu (1.00), Arg (1.02)

EXAMPLE 441

{(3R/S)-1,2,3,4-Tetrahydroisoquinolin-3-carbonyl}-Lysyl-Alanyl-{(2S)-2-Amino-3-cyclohexylpropanoyl}-Glycyl-Leucyl-DAlanyl-Arginyl-OH FAB+ MS: (M+H)+ =927; Amino Acid Anal.: Gly (0.92), Lys (1.02), Ala (1.90), Cha (0.99), Leu (1.07), Arg (1.04)

EXAMPLE 442

H-Phenylalanyl-Lysyl-{(3R/S)-1,2,3,4-Tetrahydroisoquinolin-3-carbonyl}-{(2S)-2-Amino-3-cyclohexylpropanoyl}-Glycyl-Leucyl-(N-Methyl)DAlanyl-Arginyl-OH

FAB+ MS: (M+H)+ =1003

EXAMPLE 443

H-Phenylalanyl-Lysyl-{(3R/S)-1,2,3,4-Tetrahydroisoquinolin-3-carbonyl}-{(2S)-2-Amino-3-cyclohexylpropanoyl}-Glycyl-Leucyl-(N-Methyl)DAlanyl-Arginyl-OH FAB+ MS: (M+H)+ =1003; Amino Acid Anal.: Phe (0.97), Lys (0.94), Ala (0.80), Gly (1.00), Leu (1.06), Arg (1.04)

EXAMPLE 444

H-Phenylalanyl-Lysyl-Alanyl-{(3R/S)}-1,2,3,4-Tetrahydroisoquinolin-3-carbonyl}-Glycyl-Leucyl-DAlanyl-Arginyl-OH FAB+ MS: (M+H)+ =921; Amino Acid Anal.: Phe (0.96), Lys (0.97), Ala (1.82), Gly (0.96), Leu (1.05), Arg (1.03)

EXAMPLE 445

H-Phenylalanyl-Lysyl-Alanyl-{(3R/S)-1,2,3,4-Tetrahydroisoquinolin-3-carbonyl}-Glycyl-Leucyl-DAlanyl-Arginyl-OH FAB+ MS: (M+H)+ =921; Amino Acid Anal.: Phe (1.01), Lys (1.00), Ala (1.99), Gly (0.93), Leu (1.13), Arg (1.09)

EXAMPLE 446

H-Phenylalanyl-Lysyl-Alanyl-{(2S)-2-Amino-3-cyclohexylpropanoyl}-{(3R/S)-1,2,3,4-Tetrahydroisoquinolin-3-carbonyl}-Leucyl-DAlanyl-Arginyl-OH FAB+ MS: (M+H)+ = 1017; Amino Acid Anal.: Phe (0.99), Lys (0.96), Ala (1.69), Cha (0.99), Leu (1.06), Arg (1.00)

EXAMPLE 447

H-Phenylalanyl-Lysyl-Alanyl-{(2S)-2-Amino-3-cyclohexylpropanoyl}-{(3R/S)-1,2,3,4-Tetrahydroisoquinolin-3-carbonyl}-Leucyl-DAlanyl-Arginyl-OH FAB+ MS: (M+H)+ = 1017; Amino Acid Anal.: Phe (1.01), Lys (1.02), Ala (1.79), Cha (0.99), Leu (1.10), Arg (1.08)

EXAMPLE 448

H-Phenylalanyl-Lysyl-Alanyl-{(2S)-2-Amino-3-cyclohexylpropanoyl}-Glycyl-{(3R/S)-1,2,3,4-Tetrahydroisoquinolin-3-carbonyl}-DAlanyl-Arginyl-OH FAB+ MS: (M+H)+ =961; Amino Acid Anal.: Phe (0.99), Lys (1.04), Ala (1.94), Gly (1.03), Leu (1.07), Arg (1.08)

EXAMPLE 449

H-Phenylalanyl-Lysyl-Alanyl-{(2S)-2-Amino-3-cyclohexylpropanoyl}-Glycyl-{(3R/S)-1,2,3,4-Tetrahydroisoquinolin-3-carbonyl}-DAlanyl-Arginyl-OH FAB+ MS: (M+H)+ =961; Amino Acid Anal.: Phe (1.00), Lys (1.03), Ala (2.01), Gly (0.94), Leu (1.07), Arg (1.02)

EXAMPLE 450

H-Phenylalanyl-Lysyl-Alanyl-{(2S)-2-Amino-3-cyclohexylpropanoyl}-Glycyl-Leucyl-{(3R/S)-1,2,3,4-Tetrahydroisoquinolin-3-carbonyl}-Arginyl-OH FAB+ MS: (M+H)+ = 1003; Amino Acid Anal.: Phe (0.90), Lys (0.91), Ala (1.02), Gly (0.98), Leu (1.02), Arg (1.06)

EXAMPLE 451

H-Phenylalanyl-Lysyl-Alanyl-{(2S)-2-Amino-3-cyclohexylpropanoyl}-Glycyl-Leucyl-{(3R/S)-1,2,3,4-Tetrahydroisoquinolin-3-carbonyl}-Arginyl-OH

EXAMPLE 452

FAB+ MS: (M+H)+ = 1003

(N,N-di-Allyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-OH FAB+ MS: (M+H)+ = 1023; Amino Acid Anal.: Lys (0.91), Cha (0.98), Gly (0.99), Leu (1.05), Arg (0.99)

EXAMPLE 453

(N-Allyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-OH FAB+ MS: (M+H)+ =983; Amino Acid Anal.: Lys (0.93), Cha (0.90), Gly (0.91), Leu (1.05), Arg (1.02)

EXAMPLE 454

2-Indolylcarbonyl-Lysyl-(N-Methyl)Alanyl-{(2S)-2-Amino-3-cyclohexylpropanoyl}-Glycyl-Leucyl-(N-Methyl)DAlanyl-Arginyl-OH FAB+ MS: (M+H)+ =939; Amino Acid Anal.: Lys (0.86), Cha (0.97), Gly (1.01), Leu (1.03), Arg (0.96)

EXAMPLE 455

(N,N-di-Methyl)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-OH

FAB+ MS: (M+H)+ =971

EXAMPLE 456

Ac-(Z-dehydro)Phenylalanyl-Lysyl-(N-Methyl)Alanyl-{(2S)-2-Amino-3-cyclohexylpropanoyl}-Glycyl-Leucyl-(N-Methyl)DAlanyl-Arginyl-OH FAB+ MS: (M+H)+ =983; Amino Acid Anal.: Lys (1.02), Gly (1.01), Cha (0.94), Leu (1.01), Arg (0.97)

EXAMPLE 457

Pivaloyl-Phenylalanyl-Lysyl-Alanyl-{(2S)-2-Amino-3-cyclohexylpropanoyl}-Alanyl-Leucyl-DAlanyl-Arginyl-OH

FAB+ MS: (M+H)+ = 1013

EXAMPLE 458

H-Phenylalanyl-Arginyl-Arginyl-Methionyl-Glutaminyl-Leucyl-Glycyl-Arginyl-OH

FAB+ MS: (M+H)+ = 1063; Amino Acid Anal.: Glx (0.31), Gly (0.84), Met (0.82), Leu (1.11), Phe (0.33), Arg (2.23)

EXAMPLE 459

H-Phenylalanyl-Lysyl-Arginyl-Methionyl-Glutaminyl-Leucyl-Glycyl-Alanyl-OH

FAB+ MS: (M+H)+ =950; Amino Acid Anal.: Glx (0.35), Gly (1.02), Ala (1.45), Met (0.97), Leu (1.31), Phe (0.26), Lys (0.30), Arg (1.00)

EXAMPLE 460

(N-Methyl)Phenylalanyl-Lysyl-Arginyl-Methionyl-Glutaminyl-Leucyl-Glycyl-Arginyl-OH FAB+ MS: (M+H)+ = 1049; Amino Acid Anal.: Glx (0.38), Gly (0.79), Met (0.91), Leu (0.92), Lys (0.14), Arg (1.67)

EXAMPLE 461

H-Phenylalanyl-Lysyl-Alanyl-{(2S)-2-Amino-3-cyclohexylpropanoyl}-Alanyl-Leucyl-Azaglycyl-Arginyl-OH

FAB+ MS: (M+H)+ =917.

This peptide was prepared using methodology similar to that described in: Dutta, A. S.; Giles, M. B.; Williams, J C. *J. Chem. Soc., Perkin Trans.* 1 1986, 1655-64; Dutta, A. S.; Giles, M. B.; Gormley, J. J.; Williams, J. C.; Kusner, E. J. *J. Chem. Soc., Perkin Trans.* 1 1987, 111–120.

EXAMPLE 462

H-Phenylglycinyl-Lysyl-Alanyl-{(2S)-2-Amino-3-cyclohexylpropanoyl}-Glycinyl-Leucyl-DAlanyl-Arginyl-OH

EXAMPLE 463

H-Phenylalanyl-Lysyl-Cysteinyl-{(2S)-2-Amino-3-cyclohexylpropanoyl}-{(2S)-2-Amino-3-cyclohexylpropanoyl}-Leucyl-DAlanyl-Arginyl-OH The protected peptide resin: H-Phenylalanyl-Lysyl(N-epsilon-Cbz)-Cysteinyl(S-4-methylbenzyl)-{(2S)-2-Amino-3-cyclohexylpropanoyl}-{(2S)-2-Amino-3-cyclohexylpropanoyl}-Leucyl-DAlanyl-Arginyl(N-guanidino-Tos)-Merrifield resin is prepared as described in Example 1. The peptide is cleaved from the resin as described in Example 2 with the following precautions: the peptide is extracted with degassed 20% aqueous acetic acid following cleavage with HF; and HPLC purification is accomplished using helium saturated solvents.

EXAMPLE 464

H-Phenylalanyl-Lysyl-(S-Benzyl)Cysteinyl-{(2S)-2-Amino-3-cyclohexylpropanoyl}-{(2S)-2-Amino-3-cyclohexylpropanoyl}-Leucyl-DAlanyl-Arginyl-OH The octapeptide prepared in Example 463 is dissolved in methanol saturated with ammonia to make a 0.03M solution under a nitrogen atmosphere, and the resultant solution is chilled to 0° C. Benzyl bromide (1.3 equivalents) is introduced neat, and the reaction mixture is stirred for 1 hour at 0° C. The entire reaction mixture is poured into water followed by trifluoroacetic acid addition to obtain a pH of 2. The product is subsequently isolated by HPLC using solvents saturated with helium.

EXAMPLE 465

2-Acetamidoacryloyl-Phenylalanyl-Arginyl-Aspartyl-{(2S)-2-Amino-3-cyclohexylpropanoyl}-{(2S)-2-Amino-3-cyclohexylpropanoyl}-Leucyl-DAlanyl-Arginyl-OH Excess 2-acetamido acrylic acid isobutyl mixed anhydride in tetrahydrofuran, prepared from 2-acetamido acrylic acid and isobutyl chloroformate by the standard method, is added into a stirred 0° C. solution of the peptide prepared in Example 65 in 0.1N aqueous sodium bicarbonate containing sufficient acetonitrile to produce a homogenous solution. After stirring for 6 hours at 0° C., the reaction mixture is brought to pH 2, and the peptide is purified by reverse phase HPLC followed by lyophilization.

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:

1. A C5a anaphylotoxin activity modulating compound of the formula:

A-B-D-E-G-J-L-M-Q-T or a pharmaceutically acceptable salt thereof wherein the groups A through T have the values:

A is $R_1$-$R_2$-$R_3$;

B is selected from the group consisting of $R_4$-$R_5$-$R_6$, $R_{31}$, $R_{32}$, $R_{35}$ and $R_{37}$;

D is selected from the group consisting of $R_7$-$R_8$-$R_9$, $R_{31}$, $R_{32}$, $R_{35}$ and $R_{37}$;

E is selected from the group consisting of $R_{10}$-$R_{11}$-$R_{12}$, $R_{31}$, $R_{32}$, $R_{35}$ and $R_{37}$;

G is selected from the group consisting of $R_{13}$-$R_{14}$-$R_{15}$, $R_{31}$, $R_{32}$, $R_{35}$ and $R_{37}$;

J is selected from the group consisting of $R_{16}$-$R_{17}$-$R_{18}$, $R_{31}$, $R_{32}$, $R_{35}$ and $R_{37}$;

L is selected from the group consisting of $R_{19}$-$R_{20}$-$R_{21}$, $R_{31}$, $R_{32}$, $R_{35}$ and $R_{37}$;

M is selected from the group consisting of $R_{22}$-$R_{23}$-$R_{24}$, $R_{31}$, $R_{32}$, $R_{35}$ and $R_{37}$;

Q is selected from the group consisting of $R_{25}$-$R_{26}$-$R_{27}$, $R_{31}$, $R_{32}$, $R_{35}$ and $R_{37}$;

T is $R_{28}$-$R_{29}$-$R_{30}$; or

B and D, taken together, optionally represent a group selected from the group consisting of $R_{33}$, $R_{34}$, $R_{38}$, $R_{39}$, $R_{40}$, $R_{41}$, $R_{42}$, and $R_{43}$;

D and E, taken together, optionally represent a group selected from the group consisting of $R_{33}$, $R_{34}$, $R_{38}$, $R_{39}$, $R_{40}$, $R_{41}$, $R_{42}$, and $R_{43}$;

E and G, taken together, optionally represent a group selected from the group consisting of $R_{33}$, $R_{34}$, $R_{38}$, $R_{39}$, $R_{40}$, $R_{41}$, $R_{42}$, and $R_{43}$;

G and J, taken together, optionally represent a group selected from the group consisting of $R_{33}$, $R_{34}$, $R_{38}$, $R_{39}$, $R_{40}$, $R_{41}$, $R_{42}$, and $R_{43}$;

J and L, taken together, optionally represent a group selected from the group consisting of $R_{33}$, $R_{34}$, $R_{38}$, $R_{39}$, $R_{40}$, $R_{41}$, $R_{42}$, and $R_{43}$;

L and M, taken together, optionally represent a group selected from the group consisting of $R_{33}$, $R_{34}$, $R_{38}$, $R_{39}$, $R_{40}$, $R_{41}$, $R_{42}$, and $R_{43}$;

M and Q, taken together, optionally represent a group selected from the group consisting of $R_{33}$, $R_{34}$, $R_{38}$, $R_{39}$, $R_{40}$, $R_{41}$, $R_{42}$, and $R_{43}$, and one or more of the groups $R_5$-$R_6$-$R_7$, $R_8$-$R_9$-$R_{10}$, $R_{11}$-$R_{12}$-$R_{13}$, $R_{14}$-$R_{15}$-$R_{16}$, $R_{17}$-$R_{18}$-$R_{19}$, $R_{20}$-$R_{21}$-$R_{22}$, $R_{23}$-$R_{24}$-$R_{25}$, or $R_{26}$-$R_{27}$-$R_{28}$, independently may optionally represent $R_{36}$; wherein (a) $R_1$ is selected from the group consisting of amino,(lower alkyl)amino, dialkylamino, (arylalkyl)amino, hydroxy, alkoxy, arloxy, arylalkoxy, acetamido, thioalkoxy, halogen, aryl, lower alkyl, arylalkyl, (heterocyclic)alkyl, heterocyclic, arylamino, and hydrogen;

(b) $R_2$ is selected from the group consisting of $>CR_{99}R_{100}$, $>C=CR_{95}R_{96}$, existing in either the Z- or E-configuration, oxygen, amino, and alkylamino, with the proviso that when $R_2$ is oxygen, amino or alkylamino, $R_1$ is aryl, lower alkyl, arylalkyl or (heterocyclic)alkyl;

(c) $R_3$ is selected from the group consisting of $>C=O$, $>CH_2$, $>C=S$, $>SO_2$, with the proviso that when $R_3$ is $>CH_2$ or $>SO_2$ then $R_2$ cannot be oxygen, amino or alkylamino;

(d) $R_4$ is selected from the group consisting of $>CH_2$, $>O$, $>S$, and $>NR_{101}$ where $R_{101}$ is hydrogen, lower alkyl, arylalkyl, alkenyl, hydroxy or alkoxy, with the proviso that when $R_4$ is $>O$ or $>S$ then $R_1$, $R_2$ and $R_3$ taken together represent a group selected from the group consisting of lower alkyl, arylalkyl, aryl or hydrogen;

(e) $R_5$ is selected from the group consisting of $>CR_{201}R_{202}$, $>NR_{203}$, $>C=CR_{205}R_{206}$, existing in either the Z- or E-configuration, and substituted cyclopropyl of the formula

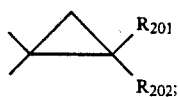

(f) $R_6$, $R_9$, $R_{12}$, $R_{15}$, $R_{18}$, $R_{21}$, and $R_{24}$ are independently selected from the group consisting of $>C=O$, $>CH_2$, $-CH_2C(O)-$, $-NHC(O)$, $>C=S$, $>SO_2$, and $>P(O)X$ where X is selected from the group consisting of hydroxy, alkoxy, amino, alkylamino and ialkylamino;

(g) $R_7$, $R_{10}$, $R_{13}$, $R_{16}$, $R_{19}$, $R_{22}$, $R_{25}$ are independently selected from the group consisting of $>CH_2$ and $>NR_{50}$ where $R_{50}$ is selected from the group consisting of hydrogen, lower alkyl, arylalkyl, aryl, hydroxy and alkoxy;

(h) $R_8$ is selected from the group consisting of $>CR_{210}R_{211}$, $>NR_{213}$, $>C=CR_{215}R_{216}$, existing in either the Z- or E-configuration, and substituted cyclopropyl of the formula

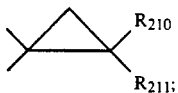

(i) $R_{11}$ is selected from the group consisting of $>CR_{220}R_{221}$, $>NR_{223}$, $>C=CR_{225}R_{226}$, existing in either the Z- or E-configuration, and substituted cyclopropyl of the formula

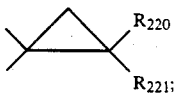

(j) $R_{14}$ is selected from the group consisting of $>CR_{230}R_{231}$, $>NR_{233}$, $>C=CR_{235}R_{236}$, existing in either the Z- or E-configuration, and substituted cyclopropyl of the formula

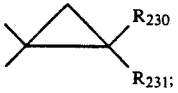

(k) $R_{17}$ is selected from the group consisting of $>CR_{301}R_{302}$, $>NR_{303}$, $>C=CR_{305}R_{306}$, existing in either the Z- or E-configuration, and substituted cyclopropyl of the formula

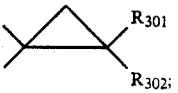

(l) $R_{20}$ is selected from the group consisting of $>CR_{310}R_{311}$, $>NR_{313}$, $>C=CR_{315}R_{316}$, existing in either the Z- or E-configuration, and substituted cyclopropyl of the formula

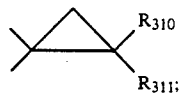

(m) $R_{23}$ is selected from the group consisting of $>CR_{320}R_{321}$, $>NR_{323}$, $>C=CR_{325}R_{326}$, existing in either the Z- or E-configuration, and substituted cyclopropyl of the formula

(n) $R_{26}$ is selected from the group consisting of $>CR_{330}R_{331}$, $>C=CR_{335}R_{336}$, existing in either the Z- or E-configuration, and substituted cyclopropyl of the formual

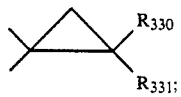

(o) $R_{27}$ is selected from the group consisting of $>C=O$, $>CH_2$, $-CH_2C(O)-$, $>C=S$, $>SO_2$, and $>P(O)X$ wherein X is selected from hydroxy, alkoxy, amino, alkylamino and dialkylamino;

(p) $R_{28}$ is selected from the group consisting of $>O$, $>S$, $>CH_2$, and $>NR_{109}$ where $R_{109}$ is selected from hydrogen, lower alkyl, (heterocyclic)alkyl, and arylalkyl, with the proviso that when $R_{27}$ is $>SO_2$ or $>P(O)X$, then $R_{28}$ is $>O$ or $>NR_{109}$;

(q) $R_{29}$ is selected from the group consisting of hydrogen, lower alkyl, arylalkyl, and $>NR_{110}$ where $R_{110}$ is selected from hydrogen, lower alkyl, aryl, and arylalkyl, with the provisos that
  (i) when $R_{28}$ is $>O$, or $>S$ then $R_{29}$ is lower alkyl or arylalkyl, and
  (ii) when $R_{29}$ is hydrogen, lower alkyl, or arylalkyl then $R_{30}$ is absent;

(r) $R_{30}$ is selected from the group consisting of hydrogen, aryl, lower alkyl, and arylalkyl;

(s) $R_{31}$ is

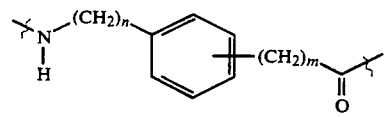

where m and n are integers independently selected from 0, 1 and 2;

(t) $R_{32}$ is

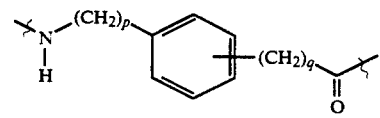

where p and q are integers independently selected from 0, 1 and 2;

(u) $R_{33}$ is

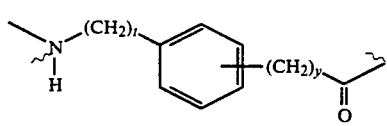

where t and v are integers independently selected from 0, 1, 2 and 3;

(v) $R_{34}$ is

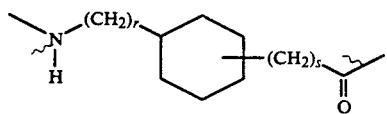

where r and s are integers independently selected from 0, 1, 2 and 3;

(w) $R_{35}$ is

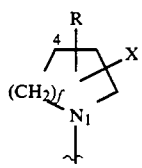

where f is and integer of 0 to 3, X is selected from the group consisting of >C=O and —CH$_2$— and R is selected from the group consisting of hydrogen and lower alkyl, with the provisos that
(i) when f is 0, X is at C-2 and R is at C-3 or C-4;
(ii) when f is 1, X is at C-2 and R is at C-3, C-4 or C-5 and C-3,4 are saturated or unsaturated;
(iii) when f is 2, X is at C-2, C-3 or C-4 and R is at C-2, C-3, C-4, C-5 or C-6 when the position is unoccupied by X and C-3,4 or C-4,5 are saturated or unsaturated; and
(iv) when f is 3, X is at C-2, C-3 or C-4 and R is at C-2, C-3, C-4, C-5, C-6 or C-7 when the position is unoccupied by X and C-3,4 or C-4,5 or C-5,6 are saturated or unsaturated;

(x) $R_{36}$ is

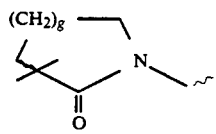

where g is an integer of from 0 to 3;

(y) $R_{37}$ is

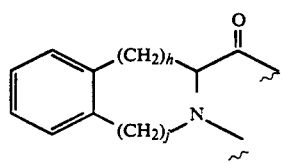

wherein h is 0 or 1 and j is 0 or 1 with the proviso that either h or j must be 1;

(z) $R_{38}$ is

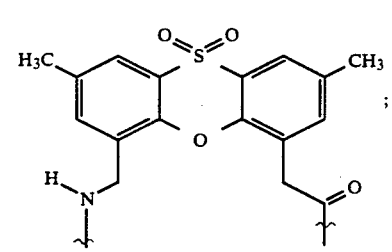

(aa) $R_{39}$ is

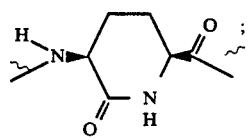

(ab) $R_{40}$ is

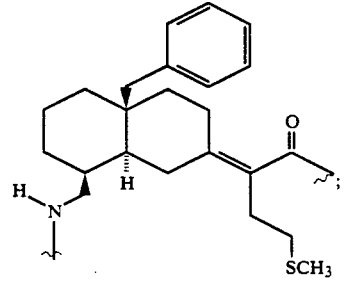

(ac) $R_{41}$ is

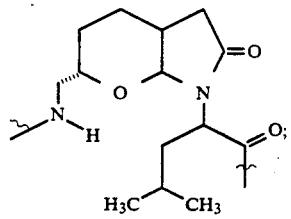

(ad) $R_{42}$ is

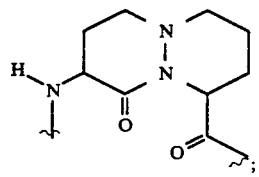

(ae) $R_{43}$ is

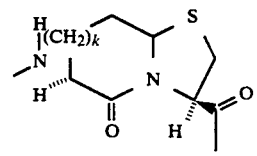

where k is an integer of from zero to two;

(af) $R_1$ is $R_2$, taken together, optionally represent a group selected from the group consisting of aryl, heterocyclic, and hydrogen;

(ag) $R_6$ and $R_7$; $R_9$ and $R_{10}$; $R_{12}$ and $R_{13}$; $R_{15}$ and $R_{16}$; $R_{18}$ and $R_{19}$; $R_{21}$ and $R_{22}$; and $R_{24}$ and $R_{25}$; each pair taken together, optionally and independently represent a group selected from the group consisting of $>CH_2$, $-(CH_2)_3-$, $-CH=CH-$, $-C\int C-$, $-C(=CH_2)CH_2-$, $-CH(OH)CH_2-$, $-C(O)O-$, $-C(O)S-$, $-CH_2C(O)O-$, $-CH_2C(O)S-$, $-CH_2O-$, $-CH_2S-$, and $-NHC(O)-$, with the provisos that (i) when $R_5$ is $>NR_{203}$ or $>C=CR_{205}R_{206}$, $R_6$ and $R_7$, taken together, represent $-C(O)NH-$ or $-C(O)NCH_3-$;

(ii) when $R_8$ is $>NR_{213}$ or $>C=CR_{215}R_{216}$, $R_9$ and $R_{10}$, taken together, represent $-C(O)NH-$ or $-C(O)NCH_3-$;

(iii) when $R_{11}$ is $>NR_{223}$ or $>C=CR_{225}R_{226}$, $R_{12}$ and $R_{13}$, taken together represent $-C(O)NH-$ or $-C(O)NCH_3{13}$ ;

(iv) when $R_{14}$ is $>NR_{233}$ or $>C=CR_{235}R_{236}$, $R_{15}$ and $R_{16}$, taken together, represent $-C(O)NH-$ or $-C(O)NCH_3-$;

(v) when $R_{17}$ is $>NR_{303}$ or $>C=CR_{305}R_{306}$, $R_{18}$ and $R_{19}$, taken together, represent $-C(O)NH-$ or $-C(O)NCH_3-$;

(vi) when $R_{20}$ is $>NR_{313}$ or $>C=CR_{315}R_{316}$, $R_{21}$ and $R_{22}$, taken together, represent $-C(O)NH-$ or $-C(O)NCH_3-$;

(vii) when $R_{23}$ is $>NR_{323}$ or $>C=CR_{325}R_{326}$, $R_{24}$ and $R_{25}$, taken together, represent $-C(O)NH-$ or $-C(O)NCH_3-$;

(ah) $R_{29}$ and $R_{30}$, taken together, optionally represent a group selected from the group consisting of hydrogen, hydroxy, and alkoxy, with the proviso that when $R_{28}$ is $>O$ or $>S$ then $R_{29}$ and $R_{30}$, taken together, represent hydrogen;

(ai) $R_1$, $R_2$ and $R_3$, taken together, optionally represent a group selected from the group consisting of lower alkyl, arylalkyl, alkenyl, aryl, hydroxy, alkoxy, hydrogen, an N-terminal protecting group or peptide fragment of 1–8 residues similarly protected wherein each of the amino acids comprising the peptide fragment is independently selected from the 20 naturally occuring amino acids;

(aj) $R_{28}$, $R_{29}$ and $R_{30}$, taken together, optionally represent a group selected from an amino acid of dipeptide selected from from the 20 naturally occuring amino acids;

(ak) $R_1$, $R_2$, $R_3$ and $R_4$, taken together, optionally represents a group selected from hydrogen, lower alkyl, arylalkyl, aryl, heterocyclic, or $H_2NC(O)-$, with the proviso that when $R_5$ is $>CH_2$ then $R_1$, $R_2$, and $R_3$ and $R_4$, taken together, may not be hydrogen;

(al) $R_{27}$, $R_{28}$, $R_{29}$ and $R_{30}$, taken together, optionally represent a group selected from the group consisting of hydrogen, lower alkyl, aryl, and arylalkyl;

(am) $R_1$, $R_2$, $R_3$, $R_4$ and $R_5$, taken together, optionally represent an aryl or heterocyclic group;

(an) $R_{95}$, $R_{96}$, $R_{205}$, $R_{206}$, $R_{215}$, $R_{216}$, $R_{225}$, $R_{226}$, $R_{235}$, $R_{236}$, $R_{305}$, $R_{306}$, $R_{315}$, $R_{316}$, $R_{335}$ and $R_{336}$ are independently selected from the group consisting of hydrogen, lower alkyl, aryl, arylalkyl, (cycloalkyl)alkyl, amidoalkyl, (carboxyamido)alkyl, ureidoalkyl, (heterocyclic)alkyl, and halosubstituted alkyl;

(ao) $R_{99}$, $R_{202}$, $R_{211}$, $R_{221}$, $R_{231}$, $R_{302}$, $R_{311}$, $R_{321}$ and $R_{331}$ are independently selected from the group consisting of hydrogen and lower alkyl;

(ap) $R_{100}$ is selected from the group consisting of hydrogen, lower alkyl, arylalkyl, (cycloalkyl)alkyl, aminoalkyl, (alkylamino)alkyl, hydroxyalkyl, guanidinoalkyl, carbosyalkyl, (heterocyclic)alkyl, (thioalkoxy)alkyl, arylalkoxy, and sulfhydrylalkyl;

(aq) $R_{201}$ is selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, sulfhydrylalkyl, (aminothioalkoxy)aklkyl, (thioarylalkoxy)alkyl, protected sulfhydrylalkyl, and halosubstituted alkyl;

(ar) $R_{203}$, $R_{213}$, $R_{223}$, $R_{233}$, $R_{303}$, and $R_{313}$ are independently selected from the group consisting of hydrogen, lower alkyl, alkenyl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, sulfhydrylalkyl, (aminothioalkoxy)alkyl, (thioarylalkoxy)alkyl, or protected sulfhydrylalkyl with the proviso that none of $R_{203}$, $R_{213}$, $R_{223}$, $R_{233}$, $R_{303}$, or $R_{313}$ may be a vinyl group or have a heteroatom directly attached to the nitrogen or separated from it by one methylene unit;

(as) $R_{210}$ is selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, ureidoalkyl, (carboxyhydrazino)alkyl, (heterocyclic)alkyl, (thioalkoxy)alkyl, sulfhydrylalkyl, (aminothioalkoxy)alkyl, (thioarylalkoxy)alkyl, protected sulfhydrylalkyl, and halosubstituted alkyl;

(at) $R_{220}$, $R_{230}$, $R_{301}$, $R_{310}$, and $R_{330}$ are independently selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, sulfhydrylalkyl, (aminothioalkoxy)alkyl, (thioarylalkoxy)alkyl, protected sulfhydrylalkyl, and halosubstituted alkyl;

(au) $R_{320}$ and $R_{323}$ are selected from the group consisting of hydrogen, lower alkyl, alkenyl, aryl, benzyl, (cycloalkyl)alkyl, -(alkylene)-C(O)NR_{340}R_{341}, -(alkylene)-NR_{342}R_{343}, -(alkylene)-NR_{344}C(O)R_{345}, hydroxyalkyl, guanidinoalkyl, carboxyalkyl, (carboxyhydrazino)alkyl, ureidoalkyl, heterocyclic substituted methyl, (thioalkoxy)alkyl, sulfhydraylalkyl, (aminothioalkoxy)alkyl, protected sulfhydrylalkyl, and halosubstituted alkyl, where $R_{340}$, $R_{341}$, $R_{342}$, and $R_{343}$ are independently selected from hydrogen and lower alkyl; and $R_{344}$ and $R_{345}$ are independently selected from the group consisting of hydrogen, lower alkyl, and halosubstituted lower alkyl, with the proviso that $R_{323}$ may not be a vinyl group or have a heteroatom directly attached to the nitrogen or separated from it by one methylene unit;

(av) $R_{325}$ and $R_{325}$ are independently selected from the group consisting of hydrogen, lower alkyl, aryl, (cycloalkyl)alkyl, -(alkylene)-$NR_{344}C(O)R_{345}$, (carboxyamido)alkyl, ureidoalkyl, (heterocyclic)alkyl, and halosubstituted alkyl, where $R_{344}$ and $R_{345}$ are as defined above;

(aw) $R_{201}$ and $R_{202}$, $R_{210}$ and $R_{211}$, $R_{220}$ and $R_{221}$, $R_{230}$ and $R_{231}$, $R_{301}$ and $R_{302}$, $R_{310}$ and $R_{311}$, $R_{320}$ and $R_{321}$, and $R_{330}$ and $R_{331}$, each pair taken together, independently may optionally represent $-(CH_2)_z-$ where z is an integer of from 2 to 6;

all of the foregoing with the provisos that (i) when more than one sulfhydrylalkyl is present in the compound, the compound exists in the oxidized disulfide form producing a cyclic molecule, or the two sulfhydryl moieties are connected by a $C_2$ to $C_8$ alkylene chain and (ii) when the compound contains a free amino group and carboxyl group, they can be cyclized to give the corresponding lactam.

2. A compound as defined by claim 1 wherein $R_4$, $R_7$, $R_{10}$, $R_{13}$, $R_{16}$, $R_{19}$, $R_{22}$, and $R_{25}$ are independently selected fromthe group consisting of >NH and >N-(lower alkyl).

3. A compound as defined by claim 1 wherein $R_6$, $R_9$, $R_{12}$, $R_{15}$, $R_{18}$, $R_{21}$, $R_{24}$, and $R_{27}$ are independently selected from the group consisting of >C=O and >CH$_2$.

4. A compound as defined by claim 1 wherein $R_5$ is selected from the group consisting of >CR$_{201}$R$_{202}$; >NR$_{203}$; >C=CR$_{205}$R$_{206}$, existing in the Z- or E-configuration; and substituted cyclopropyl of the formula

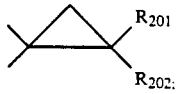

where
$R_{201}$ is selected from the group consisting of lower alkyl, alkenyl, aryl, arylalkyl, (cycloalkyl)alkyl, amidoalkyl, (carboxyamido)alkyl, (heterocyclic)alkyl, (thioalkoxy)alkyl, (thioarylalkoxy)alkyl, protected sulfhydrylalkyl, and halosubstituted alkyl;

$R_{202}$ and $R_{205}$ are selected from the group consisting of hydrogen and lower alkyl;

$R_{203}$ is selected from the group consisting of lower alkyl, alkenyl, arylalyl, (cycloalkyl)alkyl, amidoalkyl, (carboxyamido)alkyl, (heterocyclic)alkyl, (thioalkoxy)alkyl, (thioarylalkoxy)alkyl, protected sulfhydrylalkyl, with the proviso that $R_{203}$ may not be a vinyl group or have a heteroatom directly attached to the nitrogen or separated from it by one methylene group; and $R_{206}$ is selected fromt he group consisting of lower alkyl; aryl; arylalkyl; (cycloalkyl)alkyl; amidoalkyl; (carboxyamido)alkyl; (heterocyclic)alkyl; and halosubstituted alkyl.

5. A compound as defined in claim 1 wherein $R_8$ is selected from the group consisting of >CR$_{210}$R$_{211}$; >NR$_{213}$; >C=CR$_{215}$R$_{216}$, existing in either the Z- of E configuration; and substituted cyclopropyl of the formula

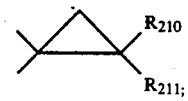

where
$R_{210}$ is selected from the group consisting of arylalkyl; aminoalkyl; guanidinoalkyl; (heterocyclic)alkyl; (aminothioalkoxy)alkyl;

$R_{211}$ and $R_{215}$ selected from hydrogen and lower alkyl;

$R_{213}$ is selected from the group consisting of arylalkyl; aminoalkyl; guanidinoalkyl; (heterocyclic)alkyl; and (aminothioalkoxy)alkyl; with the proviso that $R_{213}$ may not have a herteroatom directly attached to the nitrogen or separated from it by one methylene unit; and $R_{216}$ is selected from the group consisting of arylalkyl and (heterocyclic)alkyl.

6. A compound as defined by claim 1 wherein $R_{26}$ is selected from the group consisting of >CR$_{330}$R$_{331}$; >C=CR$_{335}$R$_{356}$, existing in either the Z- or E-configuration; and substituted cyclopropyl of the formula

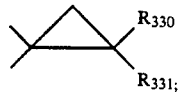

where
$R_{330}$ is selected from the group consisting of arylalkyl, aminoalkyl, guanidinoalkyl, (heterocyclic)alkyl and (aminothioalkoxy)alkyl;

$R_{331}$ and $R_{335}$ are independently selected from the group consisting of hydrogen and lower alkyl; and $R_{336}$ is selected from the group consisting of arylalkyl and (heterocyclic)alkyl.

* * * * *

UNITED STATES PATENT AND TRADEMARK OFFICE
CERTIFICATE OF CORRECTION

PATENT NO.: 5,223,485
DATED: June 29, 1993
INVENTOR(S): Megumi Kawai; Yat S. Or; Paul E. Wiedeman; Jay R. Luly and Mikel P. Moyer It is certified that error appears in the above-indentified patent and that said Letters Patent is hereby corrected as shown below:

COLUMN 5, LINE 20: Delete "$R_8$" and Insert --$R_{28}$--.

COLUMN 5, LINE 22: Delete "$R_3$" and Insert --$R_{30}$--.

COLUMN 8, LINE 32: After "$R_{211}$" insert --$R_{221}$--.

COLUMN 8, LINE 47: After "$R_{223}$" Insert --$R_{233}$--.

COLUMN 12, LINE 43: Delete "to". (2nd Occurrence)

COLUMN 14, LINE 64: Delete "Can" and Insert --can--.

COLUMN 15, LINE 47: Delete "preferebly" and Insert --preferably--.

COLUMN 15, LINE 63: Delete "herteroatom" and Insert --heteroatom--.

COLUMN 19, LINE 7: Delete "cf" and Insert --of--.

COLUMN 24, LINE 65: Delete "AC" and Insert --Ac--.

COLUMN 24, LINE 67: Delete "Isoleucyl" and Insert --Isoleucyl--.

COLUMN 29, LINE 37: Delete "alphaphene-" and Insert --alpha-phene- --.

COLUMN 32, LINE 32: Delete "Example $\eta$" and Insert --Example 72--.

UNITED STATES PATENT AND TRADEMARK OFFICE
CERTIFICATE OF CORRECTION

PATENT NO.: 5,223,485
DATED: June 29, 1993
INVENTOR(S): Megumi Kawai; Yat S. Or; Paul E. Wiedeman; Jay R. Luly and Mikel P. Moyer It is certified that error appears in the above-indentified patent and that said Letters Patent is hereby corrected as shown below:

COLUMN 32, LINE 42: Delete "{-}" and Insert --}-{--.

COLUMN 34, LINE 24: Delete "Dpipecolyl" and Insert --DPipecolyl--.

COLUMN 36, LINE 21: Delete "LeuCyl-" and Insert --Leucyl- --.

COLUMN 38, LINE 35: Delete "H-phenylalanyl-" and Insert --H-Phenylalanyl- --.

COLUMN 39, LINE 66: Delete "CyClohexyl-" and Insert --Cyclohexyl- --.

COLUMN 40, LINE 3: Delete "H-phenylalanyl-" and Insert --H-Phenylalanyl- --.

COLUMN 40, LINE 67: Delete "(3-{2'" and Insert --{3-(2'--.

COLUMN 42, LINE 7: Delete "H-Penylalanyl-" and Insert --H-Phenylalanyl- --.

COLUMN 43, LINE 28: Delete "$\Psi\{S(O)$-" and Insert --$\Psi\{S(O)_2$- --.

COLUMN 43, LINE 62: Delete "{C∫C}" and Insert --{C≡C}--.

COLUMN 44, LINE 7: Delete "leucyl-" and Insert --Leucyl- --.

COLUMN 47, LINE 10: Delete "H-phenylalanyl-" and Insert --H-Phenylalanyl- --.

COLUMN 48, LINE 23: Delete "Argiyl" and Insert --Arginyl--.

UNITED STATES PATENT AND TRADEMARK OFFICE
CERTIFICATE OF CORRECTION

PATENT NO.: 5,223,485
DATED: June 29, 1993
INVENTOR(S): Megumi Kawai; Yat S. Or; Paul E. Wiedeman; Jay R. Luly and Mikel P. Moyer It is certified that error appears in the above-indentified patent and that said Letters Patent is hereby corrected as shown below:

COLUMN 56, LINE 6:   Delete "Anal Phe" and Insert --Anal.: phe--.

COLUMN 57, LINE 66:  Delete "}PO(NHMe)" and Insert --{PO(NHMe)--.

COLUMN 59, LINE 28:  Delete "H-phenylalanyl-" and Insert --H-Phenylalanyl- --.

COLUMN 59, LINE 43:  Delete "}PO(NHMe)" and Insert --{PO(NHMe)--.

COLUMN 60, LINE 18:  Delete "Ψ}NH--CO}-" and Insert --Ψ{NH--CO}- --.

COLUMN 61, LINE 32:  Delete "cyclohexylpropanoyl){-" and Insert --cyclohexylpropanoyl)}-{--.

COLUMN 62, LINE 48:  Delete "H-phenylalanyl-" and Insert --H-Phenylalanyl- --.

COLUMN 64, LINE 54:  Delete "[" and Insert --{--.

COLUMN 65, LINE 25:  Delete "[" and Insert --{--.

COLUMN 65, LINE 34:  Delete "}2'-(4'"  and Insert --}-{2'-(4'--.

COLUMN 67, LINE 45,  Delete "H-phenylalanyl-" and Insert --H-Phenylalanyl- --.

UNITED STATES PATENT AND TRADEMARK OFFICE
CERTIFICATE OF CORRECTION

PATENT NO.: 5,223,485
DATED: June 29, 1993
INVENTOR(S): Megumi Kawai; Yat S. Or; Paul E. Wiedeman; Jay R. Luly and Mikel P. Moyer It is certified that error appears in the above-indentified patent and that said Letters Patent is hereby corrected as shown below:

COLUMN 68, LINE 62: Delete "H-phenylalanyl-" and Insert --H-Phenylalanyl- --.

COLUMN 71, LINE 15: Delete "966-" and Insert --966;--.

COLUMN 73, LINE 2: After "/S" delete --}--.

COLUMN 73, LINE 55: Delete "Glyeyl" and Insert --Glycyl--.

COLUMN 76, LINE 46: Delete "arloxy" and Insert --aryloxy--.

COLUMN 77, LINE 15: Delete "ialkylamino;" and Insert --dialkylamino;--.

COLUMN 79, LINE 2: Replace

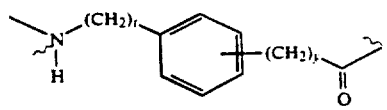

with 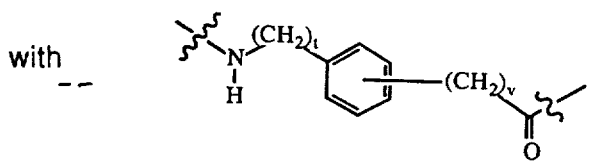

UNITED STATES PATENT AND TRADEMARK OFFICE
CERTIFICATE OF CORRECTION

PATENT NO.: 5,223,485
DATED: June 29, 1993
INVENTOR(S): Megumi Kawai; Yat S. Or; Paul E. Wiedeman; Jay R. Luly and Mikel P. Moyer It is certified that error appears in the above-indentified patent and that said Letters Patent is hereby corrected as shown below:

COLUMN 79, LINE 48:  Replace

" 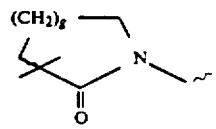 "

with

-- 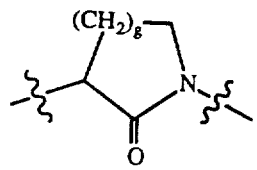 --

COLUMN 80, LINE 60:  Replace

" 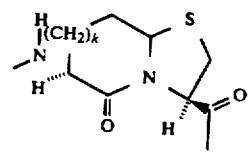 "

with

-- 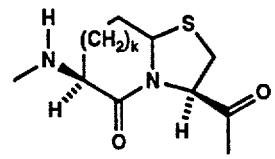 --

UNITED STATES PATENT AND TRADEMARK OFFICE
CERTIFICATE OF CORRECTION

PATENT NO.: 5,223,485
DATED: June 29, 1993
INVENTOR(S): Megumi Kawai; Yat S. Or; Paul E. Wiedeman; Jay R. Luly and Mikel P. Moyer It is certified that error appears in the above-indentified patent and that said Letters Patent is hereby corrected as shown below:

COLUMN 81, LINE 9: Delete "--C|C--" and Insert -- --C≡C-- --.

COLUMN 81, LINE 21: Delete "--C(O)NCH₃13;" and Insert -- --C(O)NCH₃--; --

COLUMN 81, LINE 50: After the word selected delete "from"

COLUMN 82, LINE 9: Delete "carbosyalkyl" and Insert --carboxyalkyl--.

COLUMN 82, LINE 18: Delete "(aminothioalkoxy)aklkyl," and Insert --(aminothioalkoxy)alkyl,--

COLUMN 83, LINE 26: Replace "fromthe" with --from the--

COLUMN 84, LINE 5: Replace "fromt he" with --from the--

Signed and Sealed this

Twenty-sixth Day of July, 1994

Attest:

*Attesting Officer*

BRUCE LEHMAN

*Commissioner of Patents and Trademarks*